United States Patent
Kline et al.

(10) Patent No.: US 11,452,460 B2
(45) Date of Patent: Sep. 27, 2022

(54) METHOD FOR DETECTING BLOCKAGE IN A FLUID FLOW VESSEL

(71) Applicant: CVR Global, Inc., Denver, NC (US)

(72) Inventors: Bret Kline, Columbus, OH (US); Peter Bakema, Denver, NC (US); Young Truong, Carrboro, NC (US); Richard Finlayson, Greenville, NC (US); Orville Day, Greenville, NC (US)

(73) Assignee: CVR Global, Inc., Denver, NC (US)

( * ) Notice: Subject to any disclaimer, the term of this patent is extended or adjusted under 35 U.S.C. 154(b) by 841 days.

(21) Appl. No.: 16/309,735

(22) PCT Filed: Jun. 15, 2017

(86) PCT No.: PCT/US2017/037805
§ 371 (c)(1),
(2) Date: Dec. 13, 2018

(87) PCT Pub. No.: WO2017/218857
PCT Pub. Date: Dec. 21, 2017

(65) Prior Publication Data
US 2019/0125196 A1    May 2, 2019

Related U.S. Application Data

(60) Provisional application No. 62/350,268, filed on Jun. 15, 2016, provisional application No. 62/350,614, (Continued)

(51) Int. Cl.
*A61B 5/0285* (2006.01)
*A61B 5/00* (2006.01)
(Continued)

(52) U.S. Cl.
CPC ........ *A61B 5/0285* (2013.01); *A61B 5/02007* (2013.01); *A61B 5/6822* (2013.01);
(Continued)

(58) Field of Classification Search
CPC .... A61B 2560/0276; A61B 2560/0425; A61B 2560/0431; A61B 2560/0462;
(Continued)

(56) References Cited

U.S. PATENT DOCUMENTS 5,494,043 A    2/1996  O'Sullivan et al.
7,621,875 B2   11/2009 Pravica et al.
(Continued)

FOREIGN PATENT DOCUMENTS

| JP | 2002-291709 A | 10/2002 |
|---|---|---|
| WO | WO/2016/205365 | 12/2016 |
| WO | WO/2016/205395 | 12/2016 |

OTHER PUBLICATIONS

Wikipedia, "Spectral density estimation" accessed with waybackmachine and archived Sep. 6, 2015 (Year: 2015).*

(Continued)

*Primary Examiner* — Sean P Dougherty
*Assistant Examiner* — Alexander H Connor
(74) *Attorney, Agent, or Firm* — Vos-IP, LLC

(57) ABSTRACT

A method for measuring sound from vortices in the carotid artery comprising: a first and second quality control provisions, wherein the quality control compares detected sounds to pre-determined sounds, and upon confirmation of the quality control procedures, detecting sounds generated by the heart and sounds from vortices in the carotid artery for at least 30 seconds. A method for determining stenosis of the carotid artery in a human patient consisting of a first step of placing a sensing device comprising an array and three sensing elements onto the patient, wherein a first sensing element is placed near the heart and the two remaining sensing elements are placed adjacent to the carotid arteries; the sensing elements then measure sounds from each of the three sensing elements, resulting in sound from three chan- (Continued)

nels. The sound is measured in analog and modified to digital format and then each of the three channels are analyzed before a power spectral density analysis is performed. The power spectral density graph reveals peaks that are not due to noise, that are then analyzed to provide for a calculation of percent stenosis or complete occlusion of the carotid artery.

17 Claims, 56 Drawing Sheets

Related U.S. Application Data filed on Jun. 15, 2016, provisional application No. 62/350,576, filed on Jun. 15, 2016, provisional application No. 62/350,617, filed on Jun. 15, 2016.

(51) Int. Cl.
*A61B 7/04* (2006.01)
*A61B 8/06* (2006.01)
*A61B 5/02* (2006.01)
*H04R 29/00* (2006.01)

(52) U.S. Cl.
CPC ............... *A61B 5/726* (2013.01); *A61B 7/04* (2013.01); *A61B 8/06* (2013.01); *A61B 5/684* (2013.01); *A61B 5/6843* (2013.01); *A61B 5/6844* (2013.01); *A61B 5/7203* (2013.01); *A61B 5/7257* (2013.01); *A61B 5/742* (2013.01); *A61B 2560/0425* (2013.01); *A61B 2560/0431* (2013.01); *A61B 2560/0462* (2013.01); *A61B 2562/0204* (2013.01); *A61B 2562/166* (2013.01); *H04R 29/00* (2013.01)

(58) Field of Classification Search
CPC ...... A61B 2562/0204; A61B 2562/166; A61B 5/02007; A61B 5/0285; A61B 5/6822; A61B 5/384; A61B 5/3843; A61B 5/6844; A61B 5/7203; A61B 5/7221; A61B 5/7257; A61B 5/726; A61B 5/742; A61B 7/04; A61B 8/06; H04R 29/00
See application file for complete search history.

(56) References Cited

U.S. PATENT DOCUMENTS

| | | | |
|---|---|---|---|
| 8,702,628 B2 | 4/2014 | Horii | |
| 2002/0072684 A1 | 6/2002 | Stearns | |
| 2004/0249293 A1* | 12/2004 | Sandler | A61B 7/00 600/481 |
| 2005/0123146 A1* | 6/2005 | Voix | H04R 29/004 381/60 |
| 2008/0039733 A1 | 2/2008 | Unver et al. | |
| 2008/0221414 A1* | 9/2008 | Baker | A61B 5/14551 600/310 |
| 2012/0232427 A1* | 9/2012 | Bakema | A61B 7/04 600/586 |
| 2014/0081175 A1 | 3/2014 | Telfort | |
| 2015/0051473 A1 | 2/2015 | Huang et al. | |
| 2015/0150505 A1* | 6/2015 | Kaskoun | A61B 5/684 600/300 |
| 2015/0320323 A1 | 11/2015 | Bakema et al. | |
| 2016/0158546 A1* | 6/2016 | Fredelake | G10L 25/78 607/57 |
| 2017/0340306 A1* | 11/2017 | Spiegel | A61B 5/4255 |

OTHER PUBLICATIONS

Bier, Martin et al., "Murmurs and noise caused by arterial narrowing—Theory and clinical practice", Fluctuation and Noise Letters, vol. 6, No. 4, Dec. 8, 2006, L422-L423.

\* cited by examiner

METHOD FOR DETECTING BLOCKAGE IN A FLUID FLOW VESSEL

CROSS-REFERENCE TO RELATED APPLICATION

This application is a 371 of PCT Application No. PCT/US2017/037805, filed Jun. 15, 2017, which claims the benefit of U.S. Provisional Application Ser. No. 62/350,614, filed Jun. 15, 2016, 62/350,617, filed Jun. 15, 2016, 62/350,576, filed Jun. 15, 2016, and 62/350,268, filed Jun. 15, 2016, the disclosure contents of which are hereby incorporated by reference in their entirety.

FIELD OF INVENTION

The present application is generally related to a method for determining blockage in a fluid flow vessel by utilizing a device comprising at least two sensor pods comprising a piezo or listening element for listening to the sound of fluid flow through the vessel to determine an amount of blockage in the vessel.

BACKGROUND OF THE INVENTION

Fluid flow in vessels is a critical issue in many fields. In the field of medicine, the flow of blood through the circulatory system is of particular interest, as stenosis, or blockages of vessels leads to stroke, heart attack, and other medical emergencies. To date, the ability to quickly and accurately determine blockage in the circulatory system is performed by Doppler type systems. However, these systems require specialized training and have some issues with false positive and false negative readings.

Fluid flow is also paramount in industrial applications where determination of the amount of blockage in a pipe is critical to performance of numerous industrial and municipal components. For example, the gas and oil industry routinely pipes millions of gallons of fluids through large pipes for transmission of these materials. However, accrued materials slowly adhere to the inside surfaces of pipes or transmission vessels; with some sections being worse than others.

Municipal systems also have issues with fluid flow in sewer systems, storm water systems, drinking water systems, gas distribution systems, etc. It is well known that sewer and storm systems frequently get clogged and fail, and currently there are no simple and easy machines or methods for determining blockage in these systems.

Of course, one of the most relevant fluid flow vessels is the human circulatory system. Rupture and blockage of the circulatory system leads to significant morbidity, mortality, and health care expense all over the world. Indeed, stroke is the major cause of adult neurological disability in the world. About eighty percent of all strokes occur from vessel blockage. Stroke is an enormous health burden on society. Ischemic Stroke is the most common cause of disability in adults and the third leading cause of mortality in developed countries. Around the world, stroke causes nine percent of all deaths (1 in 11) and is the second leading cause of death. According to the World Health Organization fifteen million people suffer stroke annually. Of these five million die and another five million are permanently disabled. In the United States stroke is the fifth, (1 in 19 in USA) leading cause of death affecting eight hundred thousand people annually (http://www.cdc.gov/stroke/). Ischemic stroke, occurring due to insufficient blood supply to the brain, accounts for the largest number of strokes (88%), followed by intracerebral hemorrhage (9%) and subarachnoid hemorrhage (3%) (http://www.strokeassociation.org/STROKEORG/About-Stroke/TypesofStroke/IschemicClots/Ischemic-Strokes-Clots_UCM_310939_Article.jsp#.V17hu46TRE4).

The primary cause of Ischemic stroke is atherosclerosis, which is a long-term inflammatory disease, begins at the adluminal surface and eventually causes endothelial abnormalities. The thickening and hardening of the vessel wall eventually produces atherosclerotic plaques which are essentially composed of lipid fibrous tissue and inflammatory cells. Progression of the plaque can lead to a narrowing of the lumen, i.e., stenosis. (The percentages of stenosis that will be quoted herein are by the NASCET standard of measuring stenosis). The superficial location of the carotids allows non-invasive methods to be used in detecting abnormal blood flow within them. Computational simulations and experimental flow visualizations both demonstrate marked differences in flow patterns distal to concentric and eccentric stenosis for moderately and severely stenosed cases. This is one example of an important parameter for blood flow characteristics which is dependent upon more than just the degree of stenosis.

Roughly half of all strokes are caused by artherothromboembolism and most of these are extracranial atheromatous lesions, most often involving narrowing of the internal carotid arteries (ICAs). Symptomatic patients with severe stenosis (70-99%) benefit from carotid endarterectomy. It has been suggested that endarterectomy could also reduce the risk of stroke from moderate (50-69%) stenosis, therefore imaging of the carotid artery is indicated in patients with symptoms of cerebral ischemia. There are several methods known in the art for attempting to accurately determine the level of stenosis in an artery.

It is a well-known fact that death from stroke has declined dramatically in the US. Lately stroke has been listed as the fifth leading cause of death rather than the third leading cause because more people are dying from lung cancer than from stroke. The American Stroke Association commissioned a panel of doctors (a "Stroke Council"), chosen on the basis of recent work in their respective fields of expertise, to assess what factors have been influencing the decline in stroke mortality. This Council issued its conclusions as "A statement from the American Heart Association/American Stroke Association" in 2008. The report was based upon systematic literature reviews, published clinical and epidemiological studies, morbidity and mortality reports, clinical and public health guidelines, authoritative statements, personal files, and expert opinion to summarize evidence. The document underwent extensive American Heart Association internal peer review, Stroke Council leadership review, and Scientific Statements Oversight Committee review before consideration and approval by the American Heart Association Science Advisory and Coordinating Committee. The review declares that "The decline of stroke mortality over the past decades represents a major improvement in population health that is observed for both sexes and all racial/ethnic and age groups. The major decline in stroke mortality represents a reduction in years of potential lives lost."

The remarkable decline in stroke mortality was acknowledged as one of the ten great public health achievements in the twentieth century. This decline has continued over the prior decade (2001 to 2010) and the drop in stroke mortality was again identified as one of the ten great public health achievements of the first decade of the twenty-first century. The Stroke Council report states that stroke mortality in the U.S. has been falling faster than ischemic heart disease mortality for several decades now. Medications for blood pressure control have had a larger and more immediate impact on stroke than on heart disease. Public health officials consider the lowering of blood pressure and hypertension control as the major contributors to the decline of stroke.

Also mentioned as contributing to the decline of stroke have been smoking cessation programs, improved control of diabetes and of abnormal cholesterol levels, and better as well as faster treatment. The Stroke Council concluded that efforts in hypertension control initiated in the 1970's were the most substantial influence to the decline in stroke mortality. An interesting aspect of this extensive report is that Duplex Ultrasonograph ("DUS") is not mentioned specifically, in spite of all of its improvements over the decades. This dovetails well with the fact that DUS lacks precision in that there is an inability to distinguish between some of the various sub-classifications of stenosis from each other, and generally, the DUS devices provide results with error bars which cross over entire decimal percentage subdivisions. As another example of this, DUS has a very high rate of variability in detecting and confirming stenosis at 50-69%, a "moderate" stenosis level, as compared to other levels of stenosis. This lack of precision and variability is concerning.

Despite the recent gains in stroke treatment, there remains a massive hole in early detection and treatment of patients before, not after, they have experienced stroke. Any stroke, even small, frequently leads to a rapid reduction in quality of life and this morbidity is especially troublesome as improved devices and scanning of patients could remove and avoid a large number of stroke occurrences, especially to patients that are generally deemed at a moderate or low risk.

SUMMARY OF THE INVENTION

In accordance with these and other objects, a first embodiment of an invention disclosed herein is directed to an apparatus that provides for a method of detecting and quantifying blockage in a fluid flow vessel through measurements of acoustic signals generated by vortices in the fluid flow vessel, and wherein said acoustic signals are detected and measured by a piezoelectric device positioned adjacent to the flow driving device and adjacent to an area of suspected blockage in the fluid flow vessel.

A preferred embodiment comprises a method of detecting a blockage in the carotid artery, by applying a listening device to the carotid artery for detection of stenosis: the method comprises a sensor array comprising at least two sensors, and a sensor base, said sensor base comprising means for performing a quality control procedure;

1. performing a quality control procedure by playing a predetermined set of tones from said base wherein said at least two sensors detect said predetermined set of tones and confirm that said sensors are functioning;
2. placing said sensors adjacent to at least one carotid artery and performing a second quality control procedure, wherein the sensors detect sounds from the carotid artery and compare said sounds to a predetermined set of sounds to confirm placement of said sensors on the carotid artery;
3. detecting, for a sufficient amount of time, the fluid flow through the carotid artery, measuring at a sampling rate between 2.4 kHz and 20 kHz;
4. amplifying the analog signal received from the sensors and converting the signal to digital within a file;
5. separating the file into a set of equal length segments of time;
6. filtering the data through a low pass filter and eliminating frequencies above about 2500 Hz;
7. Filtering the data using windowed FFT or wavelets based approaches;
8. Plotting a PSD with frequency in the x axis and intensity in the y axis, to reveal peaks from the data;
9. Utilizing a Welch method of smoothing the data, by chopping the data into pieces;
10. Examining peaks in the data after the Welch method;
12. Calculating stenosis based upon $(1-f1/f2)\times 100$, for each of the separate set of equal length segments of time from step 5.
13. Eliminating at least one of the separate sets of equal length segments
14. Re-calculating stenosis after eliminating at least of the separate sets;
15. Providing a value of stenosis based on $(1-f1/f2)\times 100$.

A further embodiment is directed to a method for measuring sound from vortices in the carotid artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones; performing a second quality control procedure on at least two sensing elements, wherein said second quality control procedure is performed by detecting blood flow through the carotid artery and comparing said detected sounds to a pre-determined sound signature; and detecting sounds generated by the vortices in the carotid artery for at least 30 seconds. The method wherein the sounds detected from the vortices in the carotid artery are between 40 Hz and 3000 Hz. The method wherein a further step (d) comprises eliminating sounds from the carotid artery that are outside of the range of 40 Hz and 3000 Hz. The method comprising a further step (e) comprising generating a power spectral density graph of the sounds from step (d). The method comprising three sensor pods. The method wherein in step a, wherein if the comparison between said detected tones and said pre-determined tones has a variance of more than 10% relative to the frequency, then the sensing element needs to be replaced. The method wherein in step b, if the detected sounds compared to the pre-determined sound signature have a variance of more than 25% relative to frequency, then the sensing elements need to be repositioned. In certain embodiments, the method wherein the difference is more than 100% relative to frequency, then repeating step a.

A further embodiment is directed to a method for measuring vortices produced in the carotid artery due to plaque accumulation in the artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones, wherein if said tones are within 10% of the frequency, the quality control procedure is passed, wherein the quality control fails, replacement of one or more sensing elements is required; performing a second quality control procedure on at least two sensing elements, wherein said second quality control procedure is performed by detecting sounds generated by blood flow through the carotid artery; wherein said at least two sensing elements detect said sounds generated by blood flow through the carotid artery, and said detected sounds are compared to a previously recorded sound signature, wherein detected sounds within 25% of the frequency of the sound signature indicates an appropriate position, and wherein detected sounds greater than 25% require repositioning of one or more of the sensors; and detecting sounds generated by sounds from vortices in the carotid artery for at least 30 seconds. The method comprising three sensor pods, wherein in step (c), detection of sounds generated by sounds from the vortices in the carotid artery are detected simultaneously by the sensor pods. The method wherein the sounds detected in step (c) are between 20 and 3000 Hz.

A further embodiment is directed to a system for measuring vortices in the carotid artery comprising: a computer, a microprocessor and memory attached thereto capable of running software, a software program, a base unit comprising at least one speaker, and an array comprising at least three sensor pods, wherein said sensor pods comprising a piezoelectric unit suitable for detecting sounds in the range of 20 Hz to 3000 Hz; wherein said array and sensor pods are positioned within a cradle of said base unit, and wherein said software generates a set of pre-determined tones through said at least one speaker and wherein said pre-determined tones are detected by said sensor pods and said software compares the detected sounds to the generated pre-determined tones to confirm that each sensor pod is accurately detecting said pre-determined tones within 10% of the Hz and amplitude of the pre-determined tones; wherein said array and sensor pods are placed onto a patient and wherein one sensor pod is placed adjacent to the heart and the second and third sensor pods are placed adjacent to the left and right carotid arteries; wherein a second quality control procedure is performed, wherein the sensor pods detect sounds from the heart and the carotid arteries and the software compares the detected sounds to a pre-determined set of sounds corresponding to the heart and sounds generated by fluid flow in the carotid arteries; detecting sounds from the heart and the carotid arteries for between 30 to 120 seconds; down sampling the detected sounds from analog to digital at a sampling rate of 20 KHz; and removing sounds from the digital outside of the 40 Hz to 3000 Hz range. The method further comprising a further step (g) of generating a Power Spectral Density plot and detecting peaks in said plot. The method comprising a further step (h) of determining percent stenosis from the peaks in said plot by calculating $(1-f1/f2) \times 100$.

A further embodiment is directed to a method for determining stenosis of the carotid artery in a human patient consisting of a first step of placing a sensing device comprising an array and three sensing elements onto the patient, wherein a first sensing element is placed near the heart and the two remaining sensing elements are placed adjacent to the carotid arteries; the sensing elements then measure sounds from each of the three sensing elements, resulting in sound from three channels; wherein the sound is measured in analog and modified to digital format via down sampling the detected sounds at a sampling rate of 20 KHz; wherein the digital sounds between 20 Hz and 3000 Hz are maintained and a power spectral density analysis is performed; wherein the power spectral density graph reveals peaks related to the vortices generated due to stenosis in the carotid artery; wherein said power spectral density graph provides for a determination of stenosis in the carotid artery. In a further embodiment, the method comprising a first step of performing a quality control procedure by playing a pre-determined tone from a speaker on a base supporting said array; detecting the sound from the speaker in each of the three sensing elements and comparing the detected sounds to the pre-determined tone; wherein said sensing elements are placed near the heart and adjacent to the carotid arteries if each sensor's detected sound is within 25% of the frequency of the pre-determined tone. In a further embodiment, the method wherein an indicator identifies if any sensor detects a sound more than 25% from the frequency of the pre-determined tone. In a further embodiment, the method wherein a sensor is replaced if the frequency is more than 25% from the frequency of the pre-determined tone.

In a further embodiment, a method for detecting stenosis in the carotid artery of a human patient consisting of: applying a set of three piezoelectric sensors to a patient, wherein said piezoelectric sensors are positioned on a Y-shaped array, positioning a first sensor on the heart and the two remaining sensors on each side of the neck of the patient, adjacent to the carotid artery; detecting and recording the sound from the three sensors simultaneously; formatting the measured sound from analog to digital via down sampling the data at 20 KHz; graphing the digital sound from a range of 20 Hz to 3000 Hz in a power spectral density graph and removing all other sounds; and determining the level of stenosis based on the graphical representation of the power spectral density graph.

In a further embodiment, a method of detecting an occlusion in an industrial fluid flow vessel comprising; placing a sensor pod having a listening device, onto said fluid flow vessel; detecting sounds passing through said fluid flow vessel; performing wavelet analysis and removing low frequency sounds below 60 Hz; performing Burg or Welch's method or both to de-noise the data; plot a Power Spectral Density plot of the frequency in the x axis and intensity in the y axis; calculating the primary two peaks in the Power Spectral Density Plot; determining stenosis of the fluid flow vessel by calculating $(1-f1/f2) \times 100$. The method wherein a first quality control procedure is performed on said listening device comprising playing from a base, a predetermined sound signature; detecting said sound signature with said listening device; comparing said detected sound signature to the predetermined sound signature; confirming proper function of the listening device if the difference between the frequency of the detected sound and the predetermined sound signature is 10% or less.

In a further embodiment, a method of detecting an occlusion in an arterial vessel comprising; placing a sensor pod having a listening device, on the skin of a patient, adjacent to said arterial vessel; detecting sounds passing through said arterial vessel; performing wavelet analysis and removing low frequency sounds below 60 Hz; performing Burg or Welch's method or both to de-noise the data; plot a Power Spectral Density plot of the frequency in the x axis and intensity in the y axis; calculating the primary two peaks in the Power Spectral Density Plot; determining stenosis of the fluid flow vessel by calculating $(1-f1/f2) \times 100$. The method wherein said arterial vessel is the carotid artery. The method wherein said arterial vessel is the coronary artery. In a further embodiment, the method comprising performing a first quality control procedure is performed on said listening device comprising playing from a base, a predetermined sound signature; detecting said sound signature with said listening device; comparing said detected sound signature to the predetermined sound signature; confirming proper function of the listening device if the difference between the frequency of the detected sound and the predetermined sound signature is 10% or less. In a further embodiment, the method comprising performing a first quality control procedure on said patient, comprising detecting with said listening device sounds of fluid flow through said arterial vessel; comparing said detected sounds to a predetermined sound signature corresponding to an expected frequency through said arterial vessel; proceeding with said detection method if said detected sound identifies a frequency corresponding to said expected frequency. In a further embodiment, the method where said expected frequency is between 60 and 260 Hz.

A further embodiment is directed to a device for detecting stenosis in the arterial circulatory system comprising a base and at least one sensor pod; said base comprising a processor and a speaker, capable of playing a predetermined sound through said speaker; said sensor pod comprising a circular piezo cap comprising a top and a bottom an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to an assembly base.

A further embodiment is directed to a method for detecting stenosis of the arterial circulatory system comprising: performing a self-diagnosis quality control procedure on a sensor element by playing a pre-determined sound signature from a speaker; detecting said pre-determined sound signature with said sensor element; comparing said detected sound signature to said pre-determined sound signature; proceeding to a second quality control procedure where said detected sound is within 25% of the frequency of the pre-determined sound signature or replacing said sensor element if said detected sound is more than 25% from the frequency of the pre-determined sound signature; placing said sensor element on an artery of interest; detecting the flow of fluid through said artery of interest; detecting a frequency of between 60 and 260 Hz to confirm proper position of said sensing element; moving said sensing element to a different position if a frequency between 60 and 260 Hz is not detected; upon detecting said frequency between 60 and 260 Hz, capturing data from said sensing element; plotting a Power Spectral Density Plot; calculating stenosis based on $(1-f1/f2) \times 100$. The method further comprising performing a wavelet analysis after capturing data from said sensing element. The method further comprising performing Burg's Method after the wavelet analysis. The method further comprising performing Welch's method after performing Burg's Method. In a further embodiment, the method wherein the calculation of stenosis is a binary calculation of greater than or less than 50%.

In a further embodiment, the invention can be simplified to the following steps by use of a sensitive listening device comprising at least two listening devices; (1) placing said at least two listening devices adjacent to the carotid artery; (2) detecting the flow of fluid through the carotid artery for a predetermined amount of time by sampling the sound at between 2.4 kHz and 20 kHz; (3) performing a filtering analysis using wavelets; (4) plotting the data from the wavelets analysis to a PSD plot with frequency in the x axis and intensity in the y axis; and (5) determining stenosis based on peaks in the PSD, wherein the stenosis is calculated according to $(1-f1/f2) \times 100$.

In a further embodiment, a method of quantifying stenosis in the carotid artery comprises: applying a first sensor to a position proximate to the heart; applying a second sensor to a position proximate to the left external carotid artery; and applying the third sensor to a position proximate to the right external carotid artery; utilizing the sensors recording the acoustic sounds at between 20 Hz and 3000 Hz from the heart and the right and left carotid arteries; transforming the acoustic sounds into digital; de-noising the data by wavelet analysis; plotting a PSD; determining stenosis based upon $(1-f1/f2) \times 100$.

A method for measuring sound from vortices in the carotid artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones; performing a second quality control procedure on at least two sensing elements, wherein said second quality control procedure is performed by detecting sounds generated by the heart and by blood flow through the carotid artery; wherein said at least two sensing elements detect said sounds generated by the heart and blood flow through the carotid artery, and said detected sounds are compared to a previously recorded set of sounds corresponding to the sounds generated by the heart and blood flow through the carotid artery; and detecting sounds generated by the heart and sounds from vortices in the carotid artery for at least 30 seconds; plotting a PSD with the frequency in the X axis and intensity in the y axis; determining peaks from the PSD; and calculating stenosis based upon $(1-f1/f2) \times 100$.

A further embodiment comprises wherein the sounds detected from the vortices in the carotid artery are between 40 Hz and 3000 Hz. A further embodiment comprises a further step (d) of eliminating sounds from the carotid artery that are outside of the range of 40 Hz and 3000 Hz. A further embodiment comprising a further step (e) comprising generating a power spectral density graph of the sounds from step (d). A further embodiment wherein three sensor pods are utilized to simultaneously detect sounds from the heart and carotid arteries.

In a further embodiment, the methods wherein if the comparison between said detected tones and said pre-determined tones has a variance of more than 5% relative to the amplitude or wavelength, then the sensing element needs to be replaced. And a further embodiment requires wherein if the detected sounds compared to the previously recorded sounds have a variance of more than 25% relative to the amplitude or wavelength, then the sensing elements need to be repositioned.

A method for measuring vortices produced in the carotid artery due to plaque accumulation in the artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones, wherein if said tones are within 5% of the amplitude and wavelength, the quality control procedure is passed, wherein the quality control fails, replacement of one or more sensing elements is required; performing a second quality control procedure on at least two sensing elements, wherein said second quality control procedure is performed by detecting sounds generated by the heart and by blood flow through the carotid artery; wherein said at least two sensing elements detect said sounds generated by the heart and blood flow through the carotid artery, and said detected sounds are compared to a previously recorded set of sounds corresponding to the sounds generated by the heart and blood flow through the carotid artery, wherein detected sounds within 25% of the previously recorded set of sounds based on amplitude and wavelength confirms an appropriate position, and wherein detected sounds greater than 25% require repositioning of one or more of the sensors; and detecting sounds generated by the heart and sounds from vortices in the carotid artery for at least 30 seconds.

In preferred embodiments the methods utilize three sensor pods, wherein the detection of sounds generated by the heart and sounds from the vortices in the carotid artery are detected simultaneously by the three sensor pods at between 20 and 3000 Hz.

A system for measuring vortices in the carotid artery comprising: a computer, a microprocessor and memory attached thereto capable of running software, a software program, a base unit comprising at least one speaker, and an array comprising at least three sensor pods, wherein said sensor pods comprising a piezoelectric unit suitable for detecting sounds in the range of 40 Hz to 3000 Hz; wherein said array and sensor pods are positioned within a cradle of said base unit, and wherein said software generates a set of pre-determined tones through said at least one speaker and wherein said pre-determined tones are detected by said sensor pods and said software compares the detected sounds to the generated pre-determined tones to confirm that each sensor pod is accurately detecting said pre-determined tones within 5% of the Hz and frequency of the pre-determined tones; wherein said array and sensor pods are placed onto a patient and wherein one sensor pod is placed adjacent to the heart and the second and third sensor pods are placed adjacent to the left and right carotid arteries; wherein a second quality control procedure is performed for 15 seconds, wherein the sensor pods detect sounds from the heart and the carotid arteries and the software compares the detected sounds to a pre-determined set of sounds corresponding to the heart and sounds generated by fluid flow in the carotid arteries; detecting sounds from the heart and the carotid arteries for between 30 to 120 seconds; and down sampling the detected sounds from analog to digital at a sampling rate of 20 KHz; and, removing sounds from the digital outside of the 20 Hz to 3000 Hz range. Certain embodiments use within 10%, 25%, or 50% of the frequency.

A further embodiment is directed to a method for determining stenosis of the carotid artery in a human patient consisting of a first step of placing a sensing device comprising an array and three sensing elements onto the patient, wherein a first sensing element is placed near the heart and the two remaining sensing elements are placed adjacent to the carotid arteries; the sensing elements then measure sounds from each of the three sensing elements, resulting in sound from three channels; wherein the sound is measured in analog and modified to digital format via down sampling the detected sounds at a sampling rate of 20 KHz; wherein the digital sounds between 20 Hz and 3000 Hz are maintained and a power spectral density analysis is performed; wherein the power spectral density graph reveals peaks related to the vortices generated due to stenosis in the carotid artery; wherein said power spectral density graph provides for a determination of stenosis in the carotid artery.

A further embodiment is directed to a method for detecting stenosis in the carotid artery of a human patient consisting of: applying a set of three piezoelectric sensors to a patient, wherein said piezoelectric sensors are positioned on a Y-shaped array, positioning a first sensor on the heart and the two remaining sensors on each side of the neck of the patient, adjacent to the carotid artery; detecting and recording the sound from the three sensors simultaneously; formatting the measured sound from analog to digital via down sampling the data at 20 KHz; graphing the digital sound from a range of 20 Hz to 3000 Hz in a power spectral density graph and removing all other sounds; and determining the level of stenosis based on the graphical representation of the power spectral density graph.

A further embodiment is directed to a method of quantifying stenosis in the carotid artery using a Y-shaped array having three sensors, consisting of: applying a first sensor attached to the leg of the Y-shaped array, to a position proximate to the heart; applying a second sensor to a position proximate to the left external carotid artery, and applying the third sensor to a position proximate to the right external carotid artery; utilizing the sensors recording the acoustic sounds at 20 to 3000 Hz from the heart and the right and left carotid arteries; transforming the acoustic sounds into digital; plotting a graph of the power spectral density from the recorded sounds, and determining the level of stenosis in the carotid artery.

A further embodiment is directed to a method for detecting stenosis in the carotid artery of a human patient consisting of the following steps: applying a set of three piezoelectric sensors to a patient, wherein said piezoelectric sensors are positioned on a Y shaped apparatus, positioning a first sensor on the heart and the two remaining sensors on each side of the neck of the patient, adjacent to the carotid artery; measuring the sound from the first sensor and from the second and third sensors; formatting the measured sound from analog to digital; removing noise from the data; graphing the sound from 60 to 3000 Hz in a power spectral density graph; and determining the level of stenosis based on an algorithm to the data from the power spectral density graph.

A further embodiment is directed to a device suitable for measuring vortices in the carotid artery comprising: a base unit, an array and three sensor pods; wherein the base comprises a speaker engaged to a computer system and wherein the array is a Y shaped array having disposed on each branch a sensor pod; wherein each sensor pod comprises a piezoelectric unit capable of detecting and transmitting sounds between 60 and 3000 Hz to the computer system for detection of vortices in the carotid artery.

Certain further embodiments for detecting stenosis comprise disposable sensor, comprising a piezoelectric element ("Piezo"), a cap, and a contact board. The sensor is mounted to the cap on one end, and the contact board mounted on the opposing end of the cap, wherein the cap comprises attachment means to secure to a base component, together defining a sensor pod.

A further embodiment is directed towards a disposable sensor assembly comprising a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects to a paired locking means, forcing contact with the contact board and powering the piezo. However, upon need for replacement, said disposable sensor assembly is quickly and easily withdrawn and replaced.

A further embodiment is directed towards a disposable sensor pod, comprising a piezo, a cap, a contact board, a PCB processor board, and a PCB housing, wherein the PCB housing comprises attachment means to secure to an array, suitable for placing said sensor pod on a patient.

A further embodiment is directed towards a disposable sensor pod comprising a disposable sensor assembly and a disposable sensor base assembly, said disposable sensor base assembly comprising a PCB processor board, a PCB housing, a diaphragm bellows membrane, locking means to secure said diaphragm bellows membrane, and a locking cap, wherein attachment means are provided to allow said disposable sensor base assembly to engage to and disengage from an array device.

A further embodiment is directed towards a disposable sensor pod comprising a piezo, a cap, a contact board, a PCB processor board, a PCB housing, a diaphragm bellows membrane (DBM) and a locking cap, wherein said piezo, cap and contact board are secured to the PCB housing, which forces contact between the contact board and the PCB processor board, and on an opposing end of the PCB housing, the DBM is defined through an aperture in an array device, and secured to said array with a locking cap that secures said DBM to said array device, with the DBM being positioned through said aperture allowing movement of the disposable sensor pod.

A further embodiment is directed towards a disposable sensor pod comprising a diaphragm bellow membrane (DBM), said DBM comprising a top, a bottom, and outer edge comprising a flange, and an opening, between said top and bottom, with an inner flange around said opening; said DMB being secured at the outer flange between an inner and outer array: and said inner flange being secured between a locking cap and a PCB housing; wherein a disposable sensor assembly engages to and selectively engages the PCB housing. In certain embodiments, the disposable sensor assembly comprises a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects to a paired locking means, forcing contact with the contact board and powering the piezo. However, upon need for replacement, said disposable sensor assembly is quickly and easily withdrawn and replaced.

A further embodiment is directed towards a disposable sensor array comprising a track structure for securing at least two sensor pods: a disposable sensor pod comprising a sensor base having an track engaging means for selectively engaging to a slideably attaching to said track structure; said disposable sensor pod comprising a disposable piezo sensor and a PCB board. In certain embodiments said disposable sensor pod comprises a diaphragm bellow membrane (DBM), said DBM comprising a top a bottom and outer edge comprising a flange, and an opening, between said top and bottom, with an inner flange around said opening; said DMB being secured at the outer flange between an inner and outer array; and said inner flange being secured between a locking cap and a PCB housing; wherein a disposable sensor assembly engages to and selectively engages the PCB housing. In certain embodiments, the disposable sensor assembly comprises a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects to a paired locking means, forcing contact with the contact board and powering the piezo. However, upon need for replacement, said disposable sensor assembly is quickly and easily withdrawn and replaced.

A further embodiment is directed towards a disposable sensor array comprising a track structure for securing at least two sensor pods; a disposable sensor pod comprising a sensor base having a track engaging means for selectively engaging to a slideably attaching to said track structure. A further embodiment is directed to disposable curved sensor pads that are configured to selectively secure to a sensor pod, and which are replaceable units for use with an individual patient. The sensor pads are made from a silicon like gel material and are molded into a predetermined shape, wherein the predetermined shape aids in transmitting sound waves from the body to the piezo elements and also in blocking out extraneous noise to prevent debris and noise within the signal and data to be analyzed.

A further embodiment is directed towards a disposable array for determining carotid artery stenosis in a human patient comprising: a stem; a neck coupled to the stem and defining an angle of between 125° and 175°; a neck vertex coupled to the neck opposite the stem; and a pair of arms extending from the neck vertex, the pair of arms defining an angle of between 90° and 145°, and wherein each of the legs and arms are made of a flexible material that is configured to be flexed away from its resting state; and wherein the flexible plastic material imparts a force to return back to its resting state. A further embodiment is directed towards the array wherein the stem and arms define a track section. A further embodiment is directed towards the array wherein each of the arms and the stem are configured to receive a sensor pod.

A further embodiment is directed towards the array for determining carotid artery stenosis in the human patient wherein each of the sensor pods comprises: a housing configured to be coupled to the arms and the stem; a disposable cap configured to removeably attach to the housing; a diaphragm that extends out of the disposable cap; a printed circuit board having integrated circuits, a rechargeable battery, spring loaded contact, an input, and LED status lights arranged thereon; a piezo element configured to receive vibrations from the diaphragm and output a signal to the input of the printed circuit board; and, optionally, a wireless charging coil configured to inductively charge the rechargeable battery.

A further embodiment is directed towards a disposable array for use in a carotid artery sensor configured as a Y-shaped structure comprising: a neck; a stem; a stem vertex arranged between the neck and the stem; a neck vertex coupled to the neck opposite the stem vertex; a left and a right arm coupled to the neck vertex, wherein the neck and stem are connected via the stem vertex such that the neck is biased at an angle of about 165 degrees; wherein the left and right arms extend substantially perpendicularly from the neck from the neck vertex, and wherein the left and right arms create a bell-like shape. A further embodiment is directed towards the array wherein each of the arms and the stem define a track like structure are configured to receive a sensor pod. A further embodiment is directed towards the array wherein the sensor pod comprises: a housing configured to be coupled to the arms and the stem; a friction plunger defined to secure the sensor pod to the track like structure on the array; a disposable cap configured to removeably attach to the housing; a diaphragm that extends out of the disposable cap; a printed circuit board having integrated circuits, a rechargeable battery, spring loaded contact, an input, and LED status lights arranged thereon; a piezo element configured to receive vibrations from the diaphragm and output a signal to the input of the printed circuit board; and, optionally, a wireless charging coil configured to inductively charge the rechargeable battery.

A further embodiment is directed towards a disposable piezo assembly comprising: a circular piezo cap comprising a top and a bottom an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to an assembly base.

A further embodiment is directed towards a sensor base for connecting to an array comprising a diaphragm bellows membrane a printed circuit board housing, a printed circuit board, and a cap; said diaphragm bellows membrane being a ring shape having an outer flange on an outer circumference of said ring, and an inner flange on an inner circumference of said ring; said outer flange engaging to said array and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means a the top of the top; said printed circuit board fitting within said opening. In certain embodiments, the attachment means being a magnet, one-half of a quarter turn locking mechanism; a groove, a pin, or threading.

A further embodiment is directed towards a disposable sensor pod comprising disposable piezo assembly and a sensor base, said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging to said array and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a disposable array comprising an array body, and three sensor pods; said array body comprising an inner array half and an outer array half, each inner and outer half comprising two arms and a neck; and three openings defined at each end of the arms and neck; said openings defined to accept a diaphragm bellows membrane, wherein said diaphragm bellows membrane comprises an outer flange to be accepted between said inner array half and outer array half; and a disposable sensor pod comprising a disposable piezo assembly and a sensor base, said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging between said inner array half and said outer array half in each of said three openings, and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a disposable array comprising a track body for accepting at least two sensor pods; said disposable array defined in a "C" like shape, wherein the track body receives a sensor having a track accepting opening, and wherein said sensor is capable of being positioned on said array by sliding said sensor along said track.

A further embodiment is directed towards a slideable disposable sensor pod comprising a disposable piezo assembly and a track accepting base end, comprising an opening defined to position on a track structure of an array; said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging to a locking groove in said track accepting base end; and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a slideable sensor pod comprising a piezo cap defining an opening between a top and bottom, a flange in said top, disposed to accept a piezo through said bottom and secure adjacent to said flange; a printed circuit contact board engaging electrical contacts between said piezo and a printed circuit board positioned below said piezo; a knuckle having an opening between a top and bottom, with said top opening receiving said printed circuit board and the bottom opening receiving a sled ball; said sled ball comprising a top having a globular shape to match the shape of the opening in the bottom of said knuckle, and a bottom defined to slide along a track of an array; a compression spring and compression washer engaging the knuckle and said sled ball to allow for movement of the sled ball to orient the sensor pod at angles from the sled ball.

Further embodiments utilize additional quality control procedures and methods to ensure accuracy of devices when detecting blockage in a fluid flow vessel. Quality control procedures can be a self-diagnostic test or an active diagnostic test. Each quality control procedures is itself sufficient to ensure proper functioning of the device, however the two procedures can be seamlessly combined to ensure proper functioning of the device and proper positioning on a patient.

A quality control embodiment comprises a sensor base, comprising a charging component, a speaker, a processor, at least one sensor, and an indicator; wherein the charging component charges a sensor pod or sensor array placed on said sensor base, and the speaker is engaged to the processor, wherein the processor generates, and plays through the speaker, a predetermined sweep of sounds across the frequency and amplitude of sounds to be detected. A sensor placed on said sensor base detects the predetermined sweep of sounds and the indicator, confirms whether the sounds detected by the sensor are within a specified tolerance of the predetermined sweep of sounds. The indicator providing one signal to indicate within the tolerance, and a second signal to indicate failure of the tolerance, thus requiring replacement of the sensor. This ensures that the piezoelectric element is functioning properly in the range to be detected by the device for analysis. In certain embodiments, the sounds played are between 1-5000 Hz, which define a predetermined sound signature. Where the sensor passes the test, the sensor is ready for use. If the sensor fails the test, the sensor or the base alerts the user to replace the sensor pod or disposable piezo assembly.

A further embodiment is directed towards a method of performing a self-diagnostic test on a sensor, comprising a base having a speaker and a processing unit, at least one sensor, comprising a piezoelectric unit, and at least one indicator, comprising: playing a predetermined sound signature from said speaker; detecting said sound signature with said sensor; processing said detected sounds and comparing said detected sounds to said predetermined sounds; indicating a failed sensor if the detected sounds are more than 25% apart from the predetermined sounds in frequency and intensity; and indicating proper function if said detected sounds are within 25% of the frequency of the predetermined sounds, wherein the sensor is ready for use. Where the indication is a failed sensor, the sensor will need to be replaced and the self-diagnostic test re-run. In certain embodiments both frequency and intensity are with a tolerance, for example 25% of a predetermined sound and intensity.

In certain embodiments, an active diagnostic test can be run immediately after the self-diagnostic test is run, wherein the active diagnostic test is a method for determining proper function of a sensor comprising, placing a sensor on a patient; detecting sounds from a patient; comparing said detected sounds from said patient to a predetermined signature; wherein a sensor is indicated as working properly if the detected sounds are within 25% of frequency of the predetermined signature, and indicated to fail if outside of 25% of the frequency.

In certain embodiments, an active diagnostic test can be run immediately after the self-diagnostic test is run, wherein the active diagnostic test is a method for determining proper function of a sensor comprising, placing a sensor on a patient; detecting sounds from a patient; comparing said detected sounds from said patient to a predetermined signature; wherein a sensor is indicated as working properly if the detected sounds are within 25% of frequency and intensity of the predetermined signature, and indicated to fail if both frequency and intensity are outside of that range.

In certain embodiments, an active diagnostic test can be run immediately after the self-diagnostic test is run, wherein the active diagnostic test is a method for determining proper placement and function of a sensor comprising: placing a sensor on a patient; detecting sounds from a patient; comparing said detected sounds from said patient to a predetermined signature; wherein a sensor is indicated as working properly if the detected sounds are within 25% of frequency of the predetermined signature, and indicated to fail if outside of that range. Wherein said sensor comprises at least three indicators, a first indicator signifying working properly, a second indicator signifying failure, and a third indicator signifying improper position, wherein an improper position indicator is generated where the frequency is between 25-50% off of the predetermined signature, wherein the sensor is re-positioned until a first indicator is signified. In certain embodiments, if no first indicator is signified within 30 seconds, a failure ($2^{nd}$) indicator is generated. In certain embodiments, a first indicator is green, a second indicator is red, and a third indicator is yellow.

In certain embodiments, the sound signature for active diagnostic test on a patient is listening for the "heartbeat" like Doppler hearing the "lub, dub." This sound is easily recognizable, and so the sound can be detected and transmitted, amplified, and played through the base speaker to indicate to the patient and to the tech, that the system is working. Furthermore, as this is a sound that is so well recognized, it may allow patients to relax or be familiar with the sound, and allow completion of the test with minimal or reduced anxiety.

In further embodiments, the sound signature is looking for the sound of flow through a particular arterial system. For example, flow through the carotid includes at least one sound signature at between 60-260 Hz. If the device does not pick up that sound, then it is not on the carotid or the carotid is highly stenosed. Accordingly, when testing the carotid, this may be a suitable sound signature. Even when this is the signature being used, it may be appropriate to still play or indicate another sound, for example, the heart beat sound.

A further embodiment is directed to an active quality control process, the method comprises: placing a sensor on the body, detecting a sound, comparing the detected sound to a sound signature, if the detected sound is within a predetermined tolerance of the sound signature proceed to start the test; if the detected sound is between 25 and 50% different than the predetermined sound signature, reposition the sensor, if the detected sound is more than 50% different than the predetermined sound signature, restart the self-diagnostic test. In certain embodiments, only the frequency is detected and used to determine the sound signature, as patient variability and environment can induce large variability that may increase false readings. Accordingly, in each embodiment, both frequency and intensity can be utilized, or only frequency for determining a sound signature.

In certain embodiments, a third indicator can illuminate if the sensor needs to be repositioned, and after repositioning, if a change in sound is detected, another indicator will illuminate, either the first and third, signifying the position is better, or the second and third, indicating the position is worse. This assists with re-positioning the sensor to the proper location until a first indicator is solely illuminated.

A method for determining proper position of sensor pod on a patient comprising: Performing a first diagnostic test on a sensor pod wherein said first diagnostic test is performed using a detection system comprising a base unit having a cradle, at least two sensor pods, a display and at least one alarm mechanism; wherein, while the sensor pods are engaged in the base unit cradle a base unit quality control procedure is performed to confirm that the sensor pods are properly functioning. After confirmation of the proper function of each of the sensor pods, the device is placed onto a patient wherein an active quality control procedure is performed. The active quality control program is run for between 5 and 30 seconds wherein each sensor pod is communicating with the computer of the system in real-time to ensure that each of the sensor pods is measuring the appropriate sounds. Wherein the system provides for an audio or visual notification that the quality control program is met, or wherein the system identifies one or more sensor pods that are improperly placed. Wherein the system then provides an alarm to any sensor pod that is not properly placed. Wherein a visual or audio mechanism is provided to provide real-time feedback as to the proper position for each sensor pod, and wherein one example provides for a red light for improper position and green light for a proper position.

A further embodiment is directed to a method above, wherein another audio or visual alarm or mechanism may be further included in the system so as to aid in the placement of the sensor pods on a patient.

A further embodiment is directed to an active quality control procedure wherein the sensor pod quality control step on the patient provides for immediate real-time feedback to the correct placement of each sensor pod to ensure fast and reliable positioning of the sensor pods, and also to confirm fast, precise, and accurate detection and determination of stenosis on the patient.

A method for determining proper placement of a sensor pod on a patient comprising: performing a first quality control procedure on a device, wherein said device comprises a base unit, at least two sensor pods, a computer system implementing appropriate software, and a display; wherein the first quality control procedure generates a tone from a speaker embedded within said base unit and wherein each of said sensor pods measures and compares the measured sound to a predetermined measurement in real-time; wherein a sensor pod is determined to have met quality control if said sound is within 5% of the predicted measurements; performing a second quality control procedure on said sensor pods, wherein said sensor pods measure sounds on a patient; wherein the system, once engaged, detects sounds from the sensor pods and compares the detected sounds in real-time to a predicted sound based on the fluid flow vessel; and wherein said method provides for an audio or visual alarm when said sensor pod is not detecting the predicted sounds, indicating an improper location for the sensor pod.

A further embodiment is directed to a method of confirming the proper position of a medical device upon a patient comprising: performing a first quality control procedure to ensure functioning of the sensor pods, comprising playing a predetermined set of sounds and comparing the predetermined sounds to the detected sounds; performing a second quality control procedure while detecting sounds from a patient wherein the test compares the detected sounds to sounds that are ordinarily present in detection of the particular artery or vessel of interest; and triggering an alarm wherein the detected sound does not meet the predicted sound, or triggering an approval if the detected sound confirms with the predicted sound.

A further embodiment is directed to a base unit that determines appropriate time for replacement of sensing devices, wherein said base unit comprises a computer implemented software connected to a database system, charging units, and a speaker, wherein the software plays a predetermined set of tones through the speaker and wherein a sensor pod placed within said base unit detects and displays the detected sound, which is compared to the predetermined set of tones played by the speaker; wherein replacement of a sensor pod is determined after the lesser of 50 quality control runs, or two quality control runs wherein the sensor pod diverges from the predicted sound by greater than 10%.

A further embodiment is directed towards a method of determining replacement of an acoustic sensing pod, comprising performing a quality control test of a base unit and at least one sensor pod, wherein said base unit comprises a computer implemented software connected to a database system, and a speaker, wherein a predetermined set of tones is played through the speaker and wherein a sensor pod placed within said base unit detects the detected sound, which is compared to the predetermined set of tones played by the speaker. The sensor pod is determined to be properly functioning wherein the detected sound differs from the pre-determined sound by less than 10% with regard to amplitude and frequency; and determined for replacement if outside of this tolerance. In certain embodiments, the sensor pod will automatically indicate replacement after a predetermined number of quality control runs. For example, at 25, 50, 75, or 100 runs will require or indicate replacement of the sensor pod.

A method for determining proper placement of a sensing pod on a patient comprising; placing a sensing pod on a patient adjacent to an area of interest; detecting sounds from the area of interest; comparing the detected sounds from the area of interest to a pre-determined sound signature; indicating proper placement if said comparison is within 25% of the detected sound as compared to the sound signature in frequency; indicating improper placement is said comparison if more than 25% variance between the detected sounds and the sound signature; moving said sensing pod on said patient until a proper placement is indicated. Generating a second indicator, providing indication if said placement is better or worse than a prior position relative to the % variance from the sound signature and detected sound.

A method for determining proper placement of a sensing pod on a patient comprising; placing a sensing pod on a patient adjacent to an area of interest; detecting sounds from the area of interest; comparing the detected sounds from the area of interest to a pre-determined sound signature; indicating proper placement if said comparison is within 25% of the detected sound as compared to the sound signature in both frequency and amplitude; indicating improper placement is said comparison is more than 25% variance between the detected sounds and the sound signature; moving said sensing pod on said patient and detected in a second sound and comparing said second sound to said pre-determined sound signature; and indicating replacement of said sensor pod wherein the variance is more than 75%.

A method for determining proper position of sensor pod on a patient comprising: performing a first diagnostic test on a sensor pod wherein said first diagnostic test is performed using an self-diagnostic test, comprising a base unit having a cradle for receiving said sensor pod, a speaker, a processing unit, a display, and at least one indicator; wherein while sensor pod is engaged in the base unit cradle and a pre-defined set of tones is played from the speaker and compared to the predefined set of tones for tolerance within 25% of the frequency of the predefined set of times; confirming proper function of each of the sensor pods within said 25% tolerance; placing said sensor pod onto a patient in a first position, wherein an active quality control procedure is performed; detecting sounds from the patient and comparing the detected sounds, in real-time, with an expected sound signature, wherein appropriate position is indicated when the detected sound is within 25% of the frequency of the expected sound; and wherein the system provides a second indicator if said detected sound is not within 25% of the frequency of the expected sound. The method further comprising moving the sensor pod to a second position if the sensor is not within 25% of the frequency of the expected sound. The method wherein another audio or visual alarm or mechanism may be further included in the system so as to aid in the placement of the sensor pods on a patient. The method wherein a set of indicators identifies whether the second position is closer to the 25% tolerance or farther away from said 25% tolerance from said first position. The method wherein the tolerance is 10%.

A method of confirming the proper position of a medical device upon a patient comprising: performing a first quality control procedure to ensure functioning of the sensor pods, comprising playing a predetermined set of sounds, detecting said predetermined set of sounds to create a first detected sounds, and comparing the predetermined sounds to the first detected sounds; performing a second quality control procedure by detecting a second detected sounds from a patient wherein the second quality control procedure compares the second detected sounds to a predetermined sound signature corresponding to the particular artery or vessel of interest; and triggering an alarm wherein the second detected sound does not meet the predetermined sound signature, or triggering an approval if the second detected sound is within a predefined tolerance from the predetermined sound signature. The method wherein the tolerance is 25%. The method of claim 6 wherein in the first setup, the comparison requires a tolerance of 25% to move to the second step.

A base unit for performing a self-diagnostic quality control process on at least one sensing pod; said base unit comprises a computer implemented software connected to a database system, charging units, and a speaker, wherein the software plays a predetermined set of tones through the speaker and wherein a sensor pod placed within said base unit detects and displays the detected sound, which is compared to the predetermined set of tones played by the speaker; wherein replacement of a sensor pod is determined after the lesser of 50 quality control runs, or two quality control runs wherein the sensor pod diverges from the predicted sound by greater than 10%.

A method of determining replacement of a wear unit comprising performing a quality control test of at least one sensor pod, comprising, placing said sensor pod onto a base unit, wherein said base unit comprises a computer implemented software connected to a database system, charging units, and a speaker, wherein the software plays a predetermined set of tones through the speaker and wherein a sensor pod placed within said base unit detects and displays the detected sound onto a display, which is compared to the predetermined set of tones played by the speaker; and determining whether to replace said sensor pod, wherein replacement of a sensor pod is determined after the lesser of 50 quality control runs, or two quality control runs wherein the sensor pod diverges from the predicted sound by greater than 10%.

A method for performing a quality control procedure on a listening device comprising: a listening device having at least one sensing element, and a base, said base comprising at least one speaker and a processing unit capable of playing a pre-determined set of tones through said speaker; playing a pre-determined set of tones through said speaker; detecting said pre-determined tones in said at least one sensing element; comparing the pre-determined tones to the detected tones; providing an indicator that the pre-determined tones are within a pre-determined tolerance of the detected tones and indicating an approval if the detected tones are within said tolerance and a rejection of the detected tones are outside of said tolerance; placing said sensing element on a patient adjacent to the carotid artery; detecting sounds from the carotid artery; comparing the sounds from the carotid artery to a predetermined carotid sound; providing a notification that the detected sounds from the carotid artery are within a pre-determined tolerance, or a rejection if the detected sounds are outside of the pre-determined tolerance; where the detected sounds are within the pre-determined tolerance, detecting sounds from the carotid artery and saving into storage for processing said sounds. The method wherein the indicator or the notification is selected from a tone, light, visual, or audio indication. The method wherein the indicator or notification is provided on the base unit, the sensor pod, the array, or combinations thereof. The method wherein the indicator and the notification are the same. The method wherein a further step comprises replacing said sensing element if a rejection is provided, and restarting the quality control procedure. The method wherein a further step comprises replacing said sensing element if a notification is provided, and restarting the quality control procedure.

A system for determining proper function and placement of a listening device; comprising a base unit comprising a speaker, computer implemented memory, and a processor, and a listening device comprising at least one sensing element; wherein said system generates a tone from said speaker and wherein said at least one sensing element detects said tone from said speaker and indicates to said processor whether the sensing element is detecting said tone within 25% of the actual frequency of the tone generated.

A method of performing a diagnostic test on a stenosis detection device; said stenosis detection device comprising at least one sensing element in electrical communication with a processor; and a base unit, in electrical communication with said processor; said base unit comprising a speaker and memory; playing a predetermined set of tones from said speaker; receiving said predetermined set of tones with said sensing element; processing in said processor said received tones and comparing said received tones to said predetermined set of tones; indicating success of said diagnostic test if said received tones are within 25% of the frequency of said predetermined set of tones; indicating failure of said diagnostic test if said received tones are more than 25% of the frequency of said predetermined set of tones, and replacing said sensing element and re-starting said quality control test; placing said stenosis detecting device onto a patient once a success is indicated; detecting sounds from said patient; comparing said detected tones to a predetermined fingerprint; and indicating success if said comparison is within 25% of said predetermined fingerprint with regard to frequency; and indicating failure if said comparison is outside of 25% of said predetermined fingerprint with regard to frequency; moving said sensing device on said patient until a success is indicated on said patient; and begin capturing data from said patient once success is indicated on said patient. The method wherein the sensing element is a piezo.

A further embodiment is directed towards a method for performing a quality control process on a sensor comprising: placing a sensor adjacent a skin surface of a patient, said sensor comprising a piezoelectric element for detecting waves generated under said skin surface; detecting said waves with said sensor; comparing said detected waves to a predetermined sound fingerprint corresponding to the area of skin surface being tested; determining whether said piezoelectric element is functioning if said detected waves are within a predetermined tolerance of said sound fingerprint; replacing said piezoelectric element if said detected waves are outside of said tolerance; and proceed to take a data sample from said patient if said detected waves are within said predetermined tolerance.

A further embodiment is directed towards a Y shaped array made of two components, an inner array and an outer array, comprising three openings, one at each of the end of the Y branches; said array made of a sound attenuating material, sufficient to reduce the ambient noises generated by the movement of the array; configured to said Y shaped array are three sensors, one positioned in each of the three openings; a diaphragm bellows membrane having a ring shape, an outer flange at the outer circumference, and an inner flange on the inner circumference of said ring; said outer circumference compressed between said inner and outer array in each opening; a sensor base configured having a locking groove to accept the inner flange between said a base housing and a locking cap; and a processing board; configured to said base housing is a disposable sensor assembly comprising a piezo sensor mounted onto a flange of a piezo cap, and comprising attachment means between said piezo cap and said housing.

A further embodiment is directed towards a C-shaped yoke having a track like feature capable of securing to said track-like feature two or more sensor pods, wherein said sensor pods are secured via a track opening in the base of each of said sensor pod.

A further embodiment is directed towards an array comprising an array body, and three sensor pods; said array body comprising an inner array half and an outer array half, each inner and outer half comprising two arms and a neck; and three openings defined at each end of the arms and neck; said openings defined to accept a diaphragm bellows membrane, wherein said diaphragm bellows membrane comprises an outer flange to be accepted between said inner array half and outer array half; and a disposable sensor pod comprising a disposable piezo assembly and a sensor base, said disposable piezo assembly comprising: a circular piezo cap comprising a top and a bottom an inner face and an outer face, with an opening between the top and bottom with the opening larger at the top than the opening at the bottom; a flange positioned on the inner face of the opening; a piezo having a top a bottom and a perimeter support; said piezo disposed of within said opening, with the bottom of the perimeter support engaged to an adhered to said flange; a Printed Circuit Board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane a printed circuit board housing, a printed circuit board, and a cap; said diaphragm bellows membrane being a ring shape having an outer flange on an outer circumference of said ring, and an inner flange on an inner circumference of said ring; said outer flange engaging between said inner array half and said outer array half in each of said three openings, and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means a the top of the top; said printed circuit board fitting within said opening.

A further embodiment is directed towards a passive noise attenuating sensor pod comprising a disposable piezo assembly and a sensor base, said disposable piezo assembly comprising: a circular piezo cap comprising a top and a bottom an inner face and an outer face, with an opening between the top and bottom with the opening larger at the top than the opening at the bottom; a flange positioned on the inner face of the opening; a piezo having a top a bottom and a perimeter support, and a noise attenuating barrier positioned around the top of the opening of the circular piezo cap, creating a second seal around a surface for detecting stenosis; said piezo disposed of within said opening, with the bottom of the perimeter support engaged to an adhered to said flange; a Printed Circuit Board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane a printed circuit board housing, a printed circuit board, and a cap; said diaphragm bellows membrane being a ring shape having an outer flange on an outer circumference of said ring, and an inner flange on an inner circumference of said ring; said outer flange engaging between said inner array half and said outer array half in each of said three openings, and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means a the top of the top; said printed circuit board fitting within said opening.

A further embodiment is directed towards an active noise cancelling method comprising; a first sensor placed adjacent to a skin surface and second sensor disposed of away from said skin surface; detecting sounds, simultaneously in said first and second sensor; processing said sounds from analog to digital and subtracting said digital sounds from said second sensor from said first sensor.

A further embodiment is directed towards an active noise cancelling method comprising: a first sensor placed adjacent to a skin surface and a second sensor disposed of away from said skin surface; detecting sounds simultaneously in said first and second sensors; processing the sounds received in said second sensor and phase shifting said sounds by 180 degrees and emitting a proportional phase shifted sound.

A further embodiment is directed towards a method of de-noising data collected from a sensor comprising receiving analog data from a first sensor; amplifying said analog data; converting the analog data to digital; performing a wavelet analysis through removal of sounds in the range of 1-70 Hz.

A further embodiment is directed towards a method of de-noising data collected from a sensor comprising receiving analog data from a first sensor; amplifying said analog data; converting the analog data to digital; performing a wavelet analysis through removal of sounds in the range of 1-70 Hz; performing a method selected from the group consisting of Burg's Method, Welch's method, or combinations thereof, and generating a Power Spectral Density.

A further embodiment is directed towards a method of reducing noise received at a sensor comprising: placing a sensor adjacent to the skin surface of a patient; wherein said sensor comprises a disposable piezo assembly and a sensor base, said disposable piezo assembly comprising: a circular piezo cap comprising a top and a bottom an inner face and an outer face, with an opening between the top and bottom with the opening larger at the top than the opening at the bottom; a flange positioned on the inner face of the opening; a piezo having a top a bottom and a perimeter support, and a noise attenuating barrier positioned around the top of the opening of the circular piezo cap, creating a second seal around a surface for detecting stenosis; said piezo disposed of within said opening, with the bottom of the perimeter support engaged to an adhered to said flange; a Printed Circuit Board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane a printed circuit board housing, a printed circuit board, and a cap; said diaphragm bellows membrane being a ring shape having an outer flange on an outer circumference of said ring, and an inner flange on an inner circumference of said ring; said outer flange engaging between said inner array half and said outer array half in each of said three openings, and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means a the top of the top; said printed circuit board fitting within said opening; placing a second sensor away from said skin surface; detecting sounds, simultaneously in said first and second sensor; processing said sounds from analog to digital and subtracting said digital sounds from said second sensor from said first sensor.

In a further embodiment, taking a method of reducing noise at a sensor from above and further by receiving analog data from a first sensor; amplifying said analog data; converting the analog data to digital; performing a wavelet analysis through removal of sounds in the range of 1-70 Hz.

In a further embodiment, further subjecting the data to Burg's method, Welch's method or both.

A further embodiment is directed to A method for eliminating noise from a data sample comprising passive noise cancellation, active noise cancellation, and a software based filtering process; said passive noise cancellation comprises collecting data from a piezo sensor that is sound isolated by a noise attenuating material surrounding said piezo sensor and forming a connection to the surface to be sampled; isolating said piezo sensor on a device comprising a membrane; said active noise cancellation comprises utilizing a second sensor adjacent to said piezo sensor to detect ambient sounds and subtracting said ambient sounds detected from said second sensor from said data; performing a wavelet analysis on said data; and performing a method selected from the group consisting Burg's method, Welch's method, and combinations thereof. The method wherein said membrane is a diaphragm bellows membrane. The method wherein said diaphragm bellows membrane is ring shaped having an outer circumference and an inner circumference; and an outer flange on the outer circumference and an inner flange on said inner circumference. The method wherein said inner flange is connected to a sensor pod comprising said piezo sensor.

A further embodiment is directed towards methods of determining stenosis include a new data adaptive filter based on wavelets that improves the ability of determining specific sounds measured by piezoelectric units by filtering out the unwanted sound frequencies such as the background noise in the input signal. The process of removing the background noise in the input signal is very complicated and challenging. Sources of the noise are many. Some can be prevented by our highly engineered and sensitive sensor. Others are unavoidable such as human voices or the ambient sounds in the room where the recording was taken. This type of noise is stationary but it is more challenging to detect sounds that are non-stationary such as the patient movement, or unexpected interruptions related to breathing, sneezing, or coughing. So many methods have been explored and the wavelets remain an effective tool for filtering out the unwanted sound frequencies, and after analyzing thousands of samples of the human artery sound data, our objective has been achieved by identifying a class of the wavelets that works very effectively to de-noise the signal for the next procedure which is based on Fast Fourier Transform to extract the desired sound spectrum for quantifying the degrees or percent of partially occluded arteries.

A further embodiment is directed towards an array, comprising a disposable sensor pad, a disposable piezo assembly, wherein said device is capable of communicating with a base device for performing a self-diagnosis quality control procedure; wherein said disposable piezo assembly is utilized to gather data from a fluid flow vessel and wherein based on said data, percent occlusion of said fluid flow vessel can be calculated.

A sensor device, comprising a base having a quality control mechanism, and a processor capable of de-noising a detected sample.

A sensor device comprising a component for performing a quality control procedure; indicators for indicating quality control procedure; a sensor pod comprising a sound attenuating barrier for passively preventing ambient noise from reaching said sensor pod; active noise cancellation components; comprising a parallel sensor measuring ambient sounds; and a processor for determining occlusion in the fluid flow vessel from data collected from said sensor pod.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The embodiments contemplate devices, systems, and methods for determining blockage in a fluid flow vessel. To reliably determine fluid flow, we need to determine that the components of the device are working properly, are clean and sanitary, are positioned in the correct locations for detection. Furthermore, the device needs to passively prevent ambient noise from entering the sensing device. However, active noise cancellation strategies can further eliminate ambient noise. Finally, processing strategies can be utilized to filter the collected data and to break it apart into useable packets of data for determination of occlusion in a fluid flow vessel.

For many cases, fluid flow vessels include the arterial circulatory system, for example the carotid artery, but also the arteries of the heart, the coronary arteries. However, flow through industrial pipes can also be evaluated using the devices and methods described herein.

Description of Ring Vortices being Detected

Figure 1:
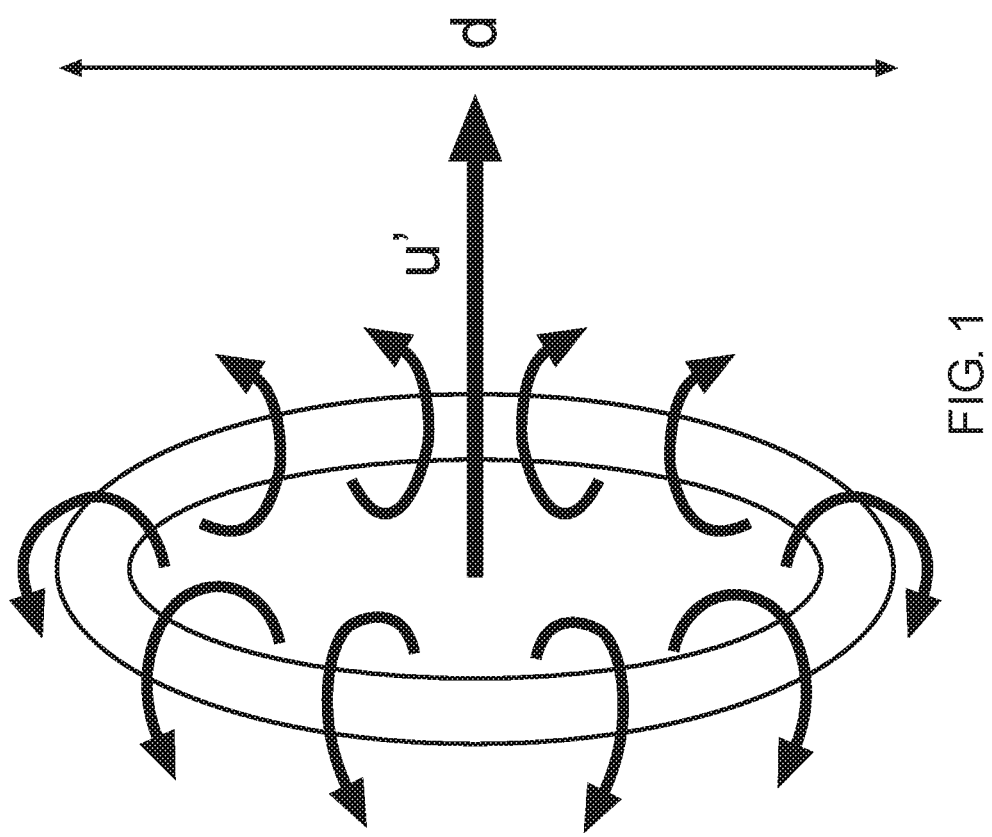
FIG. 1 depicts a ring vortex.

FIG. 1 is the side view of a ring vortex showing the rotation of the core, the velocity of the motion of the center of the core (u'), and the diameter of the vortex (d). In a carotid artery, the diameter of the vortices are initially equal to the diameter of the stenosed region. This is followed by a second region in which the diameter is equal to the inside diameter of the artery. Note that the core is thin compared to the radius of the entire ring. Inside the core, the blood molecules rotate as shown by FIG. 1 in circular or near circular (elliptical) motion around the center of the core. A blood molecule farther from the center rotates at higher velocity than one which is closer to the center. This is similar to a solid disk. The rotational motion is coherent, which maintains the same angular velocity without friction between particles at different distances from the center. This solid like motion eliminates internal frictional, dissipative forces, which if they existed would diminish the energy of the rotation quite rapidly. In such a case, the vortices would not travel nearly as far, turning to full turbulence at shorter distance of motion.

Figure 2:
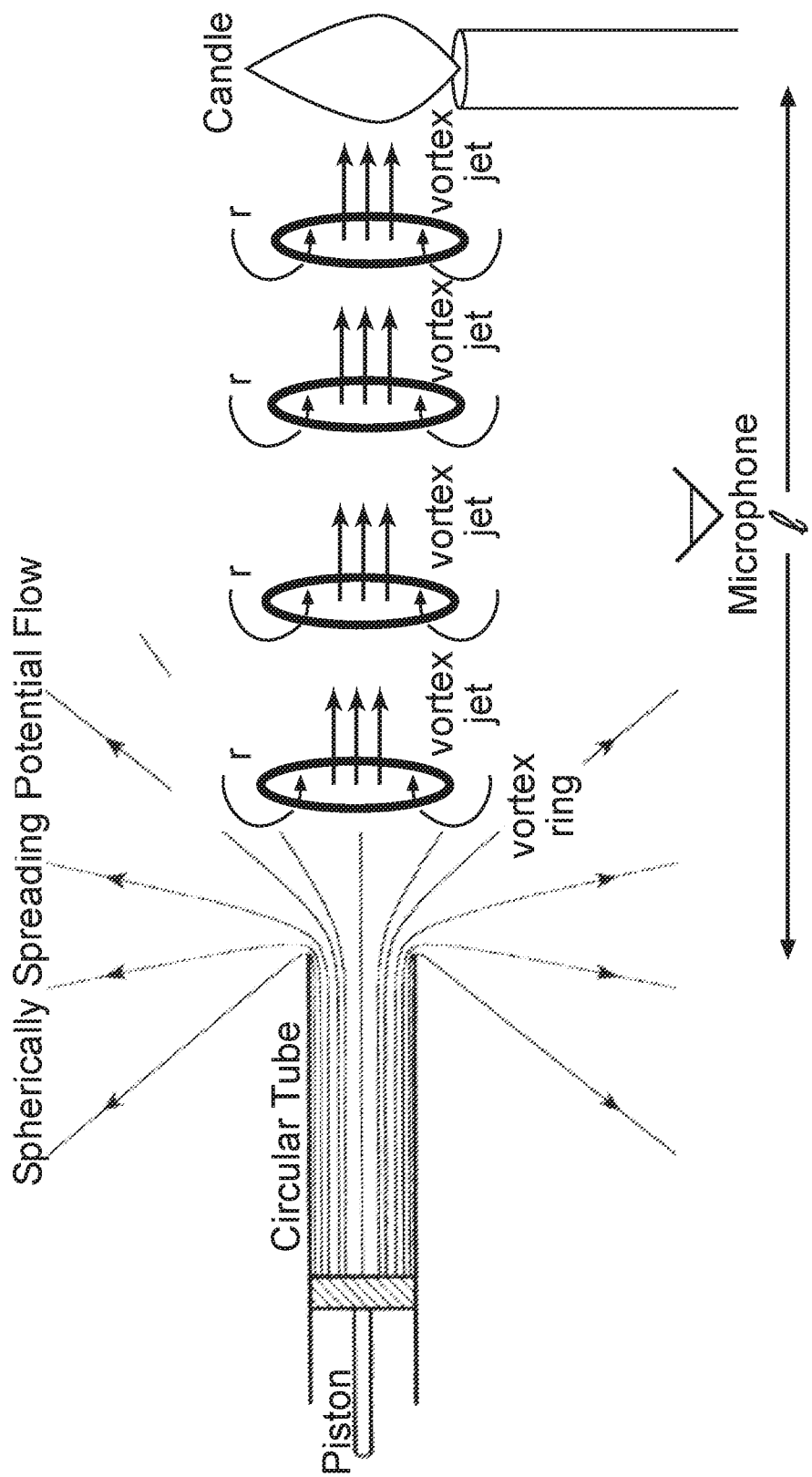
FIG. 2 depicts a ring vortex.

The ring vortices are produced equidistant from each other at a distance between them equal to their diameter as they move downstream, as illustrated in FIG. 2 which shows the formation of ring vortices upon the exit of air from a long tube. In this well-known experiment, air is being blown from a cylinder due to the motion of a piston within the cylinder. As the air departs the cylinder at sufficient velocity, ring vortices in the emerging air are formed and remain at the same diameter and distances between adjacent vortices for the entire distance that they travel. They will later dissipate into smaller eddies, which is called full turbulence. As the ring vortices pass the flame, the high speed of the air within the core of the ring vortices will blow out the flame. The air ring vortices are sufficiently stable to travel a distance of 10-20 times the distance between the individual rings. The arrows above and below the cylinder shows that air spreads out as it leaves the cylinder because there are no containing walls. Yet the diameter of the rings does not increase as they move toward the flame. Within the carotid artery, the medium is blood rather than air but the behavior is the same if the Reynolds number is the same. In the artery blood is not free to expand beyond the size of the artery, however, the size of the vortices in the flow of blood remains the same diameter as the orifice (stenosis) opening, even though the size of the artery is larger than the diameter of the vortices. In FIG. 2 which illustrates vortices in air the size of the vortices is a small percentage larger than the size of the cylinder opening. In the flow of blood in which the flow is restricted to the size of the artery rather than being free to expand, the size of the vortices is the same as the size of the jet emerging from the stenosed section of the artery. Note that the most recent vortex formed is at a distance of approximately one vortex diameter from the orifice. A microphone placed to the side of the vortex flow will measure sound at a frequency given by the frequency in which the vortices pass in front of the microphone. Sound is produced by the vortices because the rapid motion of molecules inside the ring is highly organized, that is non-random, which causes lower pressure at the surface of each individual vortex ring. This lower pressure at the surface of the vortex ring followed by a higher pressure between the vortex rings, causes sound to be transmitted to the microphone. This is the same principle as occurs in the passage of ring vortices within a blood vessel [Mollo-Christensen, Kolpin, and Marticcelli, "Experiments on jet flows and jet noise far-field spectra and directivity patterns," Journal of Fluid Mechanics 1964, Vol. 18, Iss. 2, 285-301]. Note the sound is produced in a direction perpendicular to the motion of the ring vortices, along the axis of the artery.

Figure 3:
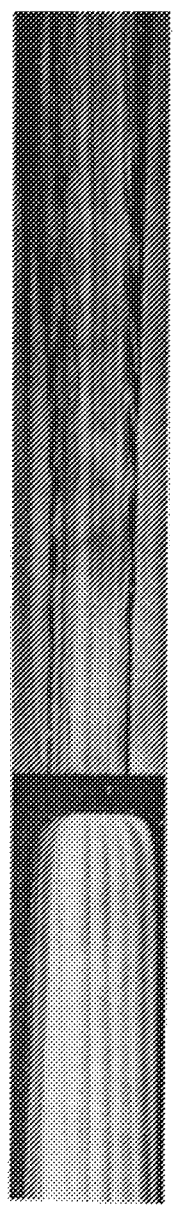
FIG. 3 depicts a ring vortex.

In FIG. 3, [Johansen 1930, FIG. 8 of "Flow through pipe orifices at low Reynolds numbers," Proceedings of the Royal Society A, vol. 126, 231-245.] is a photograph of blood flow below the critical value. This Reynolds Number (RE) equals $vD/\eta = 600$, where v is blood velocity, D is diameter of artery, and $\eta$ is blood kinematic viscosity (equals $0.035 \text{ cm}^2/\text{s}$, at human temperature). Flow is from left to right. Note that there are no ring vortices yet formed since the velocity of the blood is too low as in the diastolic phase of the cardiac cycle and latter part of the systole. There are however small striations which occur at RE lower than the critical value, but vortex rings do not yet form.

Figure 4:
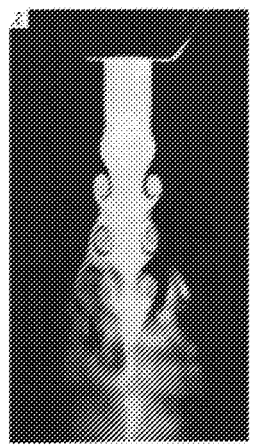
FIG. 4 depicts a ring vortex.

At RE less than 800 or greater than 2100, ring vortices do not form. The closer to 800 while still remaining below 800, the more string-like motions are seen, as seen in FIG. 3. At greater than 2100, the vortices break-up into small eddies with random orientations [Johansen 1930]. FIG. 4, [Becker & Massaro, FIG. 5, number 2 of "Vortex evolution in a round jet" Journal of Fluid Mechanics 1968, vol. 31, part 3, 435-448] shows three ring vortices emerging from an orifice. Note that the ring vortices without confining walls disintegrate into small eddies after only three ring vortices. Also note that the diameter of the ring vortices remains constant and the distance between adjacent vortices is equal to the diameter of a single vortex.

Figure 5:
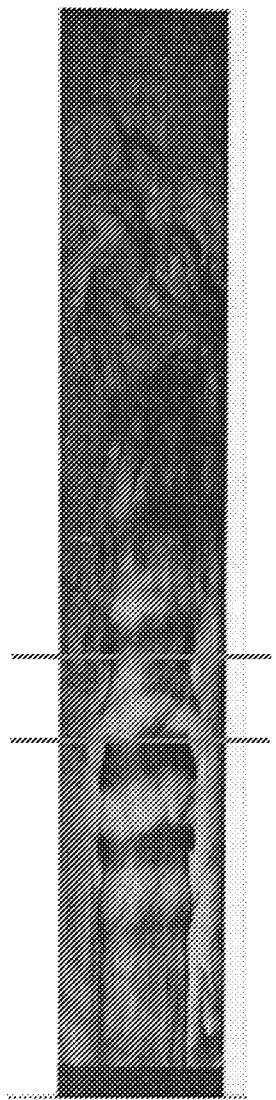
FIG. 5 depicts a ring vortex.

FIG. 5, [Johansen 1930, FIG. 8] shows the blood flow pattern including ring vortices when the RE is 1000, which is above the critical value for ring vortices to be formed. The blood flow is from left to right, the transition region from smaller diameter vortices to larger occurs rapidly in less than the distance between two of the larger vortices. The centers of all vortices, small or large, travel at the same speed. We call the first region, with smaller diameter vortices, Region I. The region of the larger vortices we call Region II. Region III follows Region II, where the vortices have disintegrated into small eddies. Because the vortices in Region I are closer together a higher sound frequency is produced, which we call f2, than is produced by the larger vortices which have a larger distance between them which produce lower sound frequency, f1. The diameter of the small vortices matches the diameter of the stenosed region. The diameter of the large vortices matches the diameter of the blood vessel in the non-stenosed region. The ratio of the two frequencies is the same as the ratio of the diameters, from which percentage stenosis can be determined. Variations from one patient to another in diameter of artery, velocity of blood, blood viscosity, temperature, and other variables cancel when taking the ratio of the two frequencies. In each heart cycle, the velocity rises above critical value during systole, and drops below critical value during diastole. Typical values for the Internal Carotid Artery (ICA) at Peak Systolic Velocity (PSV) range from velocity of 64-77 cm/s and diameter of ICA between 0.511 cm (for men) and 0.466 cm (for women) yield RE equal to 852 (for men) and 1124 (for women), well within the range that produces ring vortex flow in the ICA. Also the ring vortices only appear during the deceleration phase of the systolic part of the heart cycle that is following the moment of peak systolic velocity. Using the formulas given on by Becker and Massaro [1968, pg 446], $f*d/v = 0.0122*\mathrm{Sqrt}(RE)$, where v is the blood velocity, d is the diameter of the vortices, and f is the observed frequency seen at the microphone placed over the artery. Typical values of the solution of this equation at 50% stenosis yields f1=178 Hz and f2=356 Hz with a similar formula from other authors also quoted by Becker and Massaro [1968, pg 446], one obtains f1=236 Hz and f2=472 Hz. Different patients at 50% stenosis could have different values of frequency for the two peaks, but they will remain at the same proportionality.

If no f1 appears in the PSD (between 60 and 260 Hz), there was insufficient energy in the flow emerging from the stenotic region for the vortices to reach Region II, in which the larger vortices appear, at the lower frequencies. This indicates the artery is heavily stenosed. If there is no f2, there is an insufficient amount of stenosis to create the smaller vortices (Region I) indicating a low level of stenosis (below 15%) as reported by Khalifa and Giddens ["Characterization and evolution of poststeotic flow disturbances," Journal of Biomechanics 1981. Vol. 14, No. 5, pg292] who report that below 25% reduction in area due to stenosis (which corresponds to a reduction of 13% in diameter), no signal is picked up. If there is neither f1 nor f2, the indication is that there is a near blockage level of stenosis, as the vortices cannot be produced even when the velocity is sufficient to give RE between 800 and 2100.

To measure the large ring vortices, we need to ensure that the device we are using contains properly sterile and functioning elements. Described herein are certain disposable components, methods for determining proper function of these elements, and methods for eliminating and reducing noise from the data sample in order to accurately and efficiently measure and quantify stenosis in the arterial circulatory system.

Figure 52:
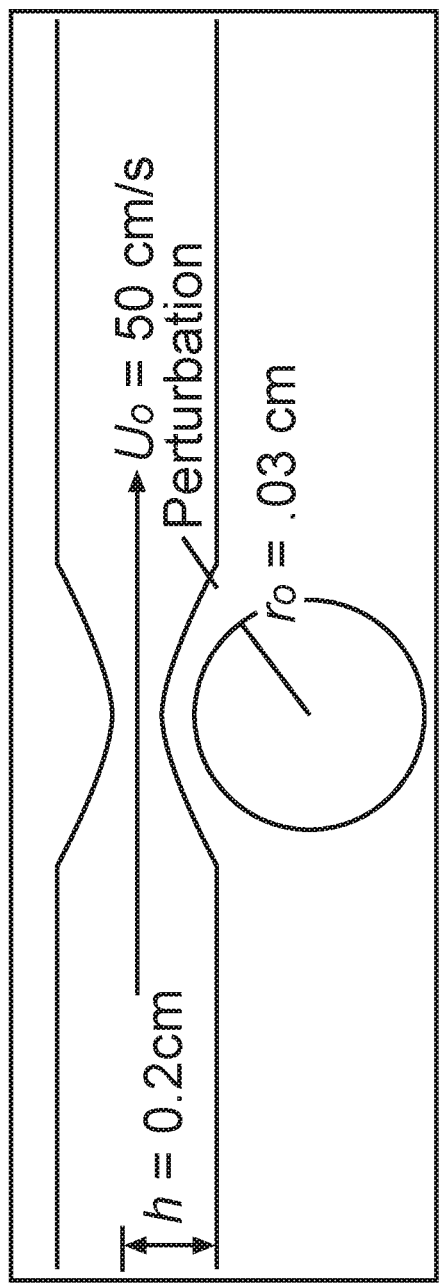
FIG. 52 depicts a perturbation representative in an artery.

Furthermore, these aspects and teachings can be applied into industrial structures. For example, these same perturbations that are present in industrial piping, such as fluid flow in gas an oil industries, production of fats, oils, and other consumer goods, chemical and biological production, and the like. Representative perturbations are depicted, for example in FIG. 52. Accordingly, the device can be utilized to identify and quantify percent blockage within a fluid flow vessel, whether that is in the arterial circulatory system or whether it is within an industrial pipe or tube.

Replacement components provide for accurate and clean components that ensure greater chance of accuracy and reproducibility. Piezoelectric sensors have a variety of potential uses, but as described herein, they are being utilized as a contact microphone. The principle of operation of a piezoelectric sensor is that a physical dimension, transformed into a force, acts on two opposing faces of the sensing element. Detection of pressure variations in the form of sound is the most common sensor application, e.g. acting as a microphone, wherein the sound waves bend the piezoelectric material creating changing voltage. Accordingly, the piezo sensor can be placed on or near a sound to receive the sounds.

Piezo sensors are especially used with high frequency sound in ultrasonic transducers for medical imaging and industrial nondestructive testing. However, piezo sensors are also frequently used for the detection and activation of a device, based on the ability to receive a signal and to then send an electronic signal, thereby acting as the actuator. In the embodiments herein, piezoelectric sensors ("Piezo") are utilized for their ability to detect certain frequency sounds or vibrations caused by the distortion of a fluid flow vessel, specifically of the arterial circulatory system.

Because of the sensitivity of these sensors, piezoelectric sensors can be somewhat fragile and can be broken from both normal use and misuse. Furthermore, as utilized in a medical device, there is the inherent need to ensure accuracy of each of the three piezoelectric sensors. Accordingly, any slight modification of the sensor may result in a modification of the input received and thus would result in erroneous data.

Replacement components may be one of three different components as described herein. A first component may be a disposable piezo assembly, a second component may be a sensor pod, which comprises the disposable piezo assembly and a sensor base, and a third component may be a disposable array, comprising one or more sensor pods. In this manner, each component may be disposable to allow for easy replacement after use.

Piezo sensors can include any number of materials. Typically, however, the sensor contains a portion of ceramic material and a metallic component. Piezo sensors may also use a polymer film configuration which exhibits a low acoustic impedance similar to that of human tissue, or made of metallic materials. These sensors, as used in the invention herein, are typically a circular shape with a diameter of about 3 inches. Typical piezos have a diameter from about 0.01 to about 6 inches for use in medical settings, with most typical sizes between about 0.5 to about 4 inches in diameter. For most applications, including industrial settings, a range of 0.01 inch to about 12.0 inches is preferred, wherein the size of the piezo is generally related to the diameter of the fluid flow vessel to be measured. In preferred embodiments, the fluid flow vessels are veins and arteries in the body, for which a 4.0 inch or smaller diameter piezo is preferable.

There is no inherent frequency limit for a piezoelectric sensor. However, the limits of applications are usually determined by resonances associated with the shape and/or the size of the transducer design. The Piezo sensors utilized herein have a thickness of about 0.01 to 2.0 mm and are capable of detecting sounds between 10 Hz and 32 KHz and an amplitude of 0.0002 N/m2 to greater than 10 N/m2. In preferred embodiments, the piezos attached to a sensor pod detect sounds between about 20 to 3000 Hz, which are relevant towards measurements of fluid flow in the body. Typically, these sounds have an amplitude of between 0.002 N/m2 and 20 N/m2. While additional sounds are recorded, many of these sounds, i.e. the heart beat and extraneous noise, are removed from the data set through several filters.

Figure 23:
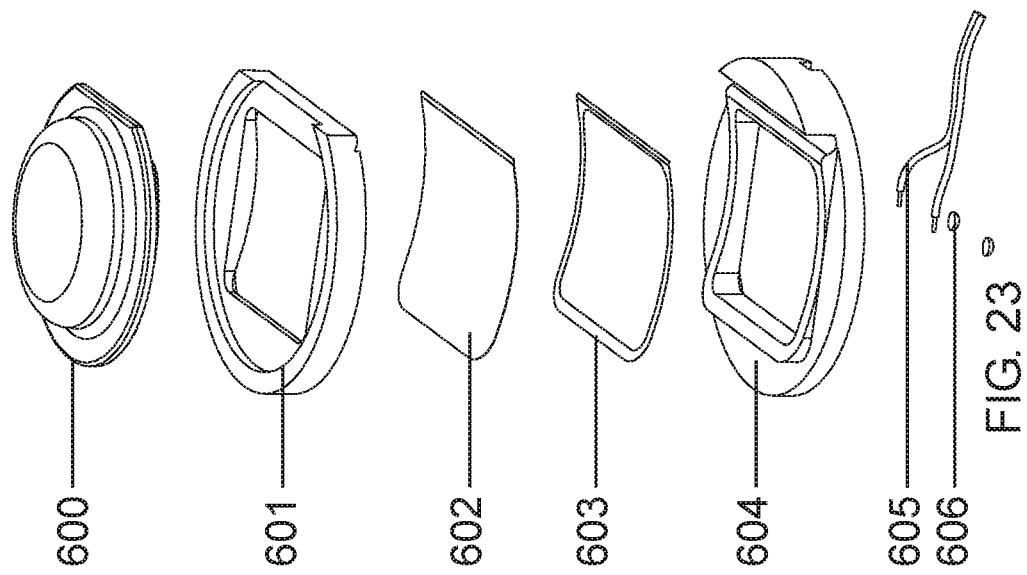
FIG. 23 depicts a concave piezo.
Figure 22:
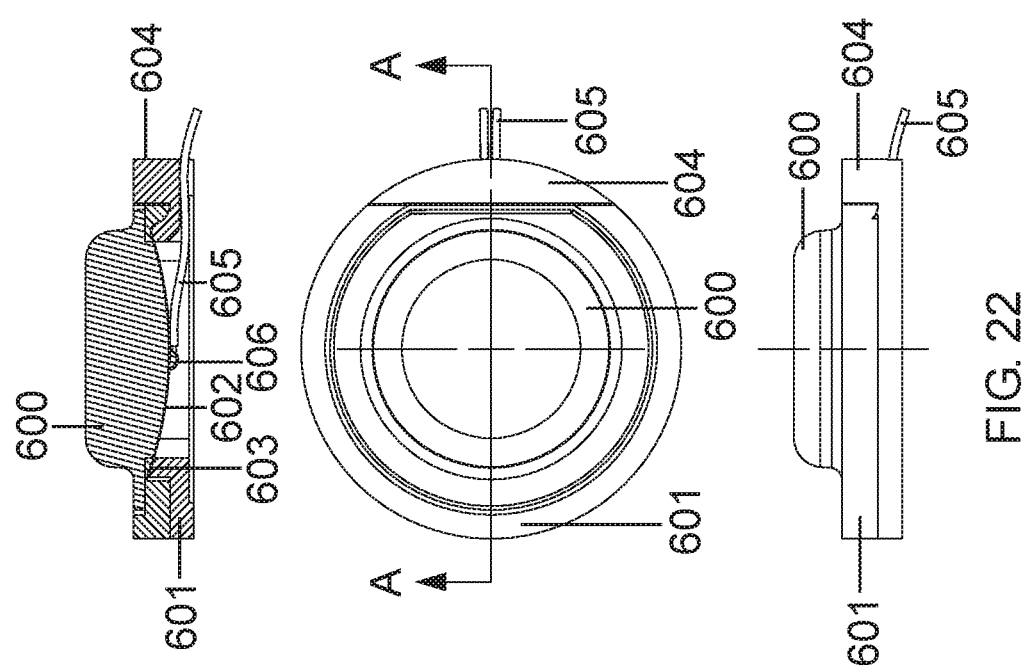
FIG. 22 depicts a sensor paid with a curved, concave piezo.

FIGS. 22 and 23 specifically depict a new piezo and mount. The piezo 602 is a concave piezo, made of metallic or polymeric materials. Curved cap 601 contains an outer rim, and an inner flange adjacent to a central opening having a similar size and shape to the piezo. The flange supports the piezo 602 which can be engaged with an adhesive 603.

In the broadest sense, the piezo sensors are disposed of within a pod. On one side of the piezo is placed a sensor pad, for example those of 1, 2, 17 and 19. The sensor pad is then pressed against the skin or clothing of a patient to listen to the underlying circulatory system. The sensor pad allows for transmission of energy waves, sound and vibrations, which are received by the piezo element. Gel or other impedance matching substance may be applied to the skin facing surface of the pad.

Figure 6:
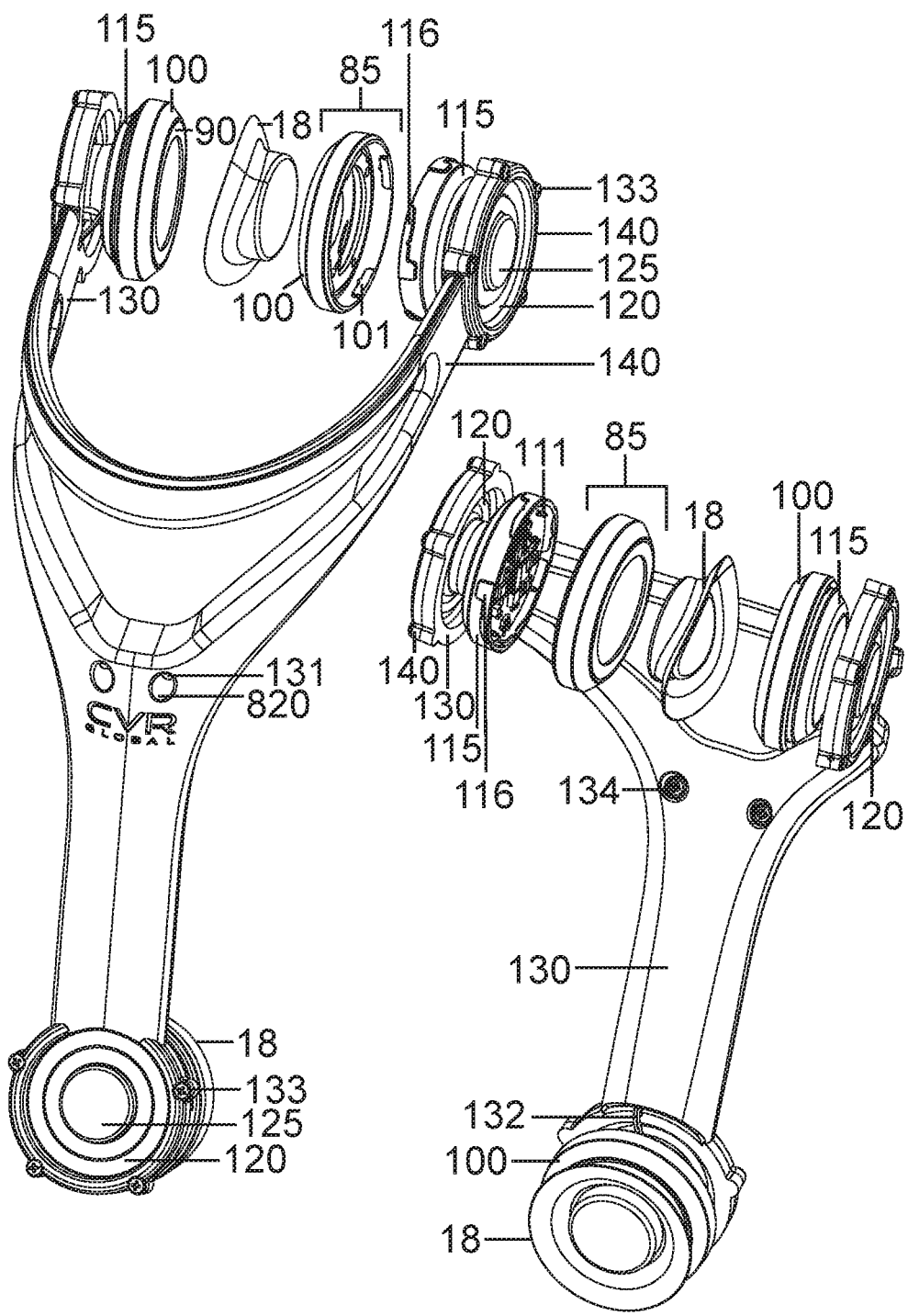
FIG. 6 depicts a partial exploded view of a sensor array and piezo pods.
Figure 11:
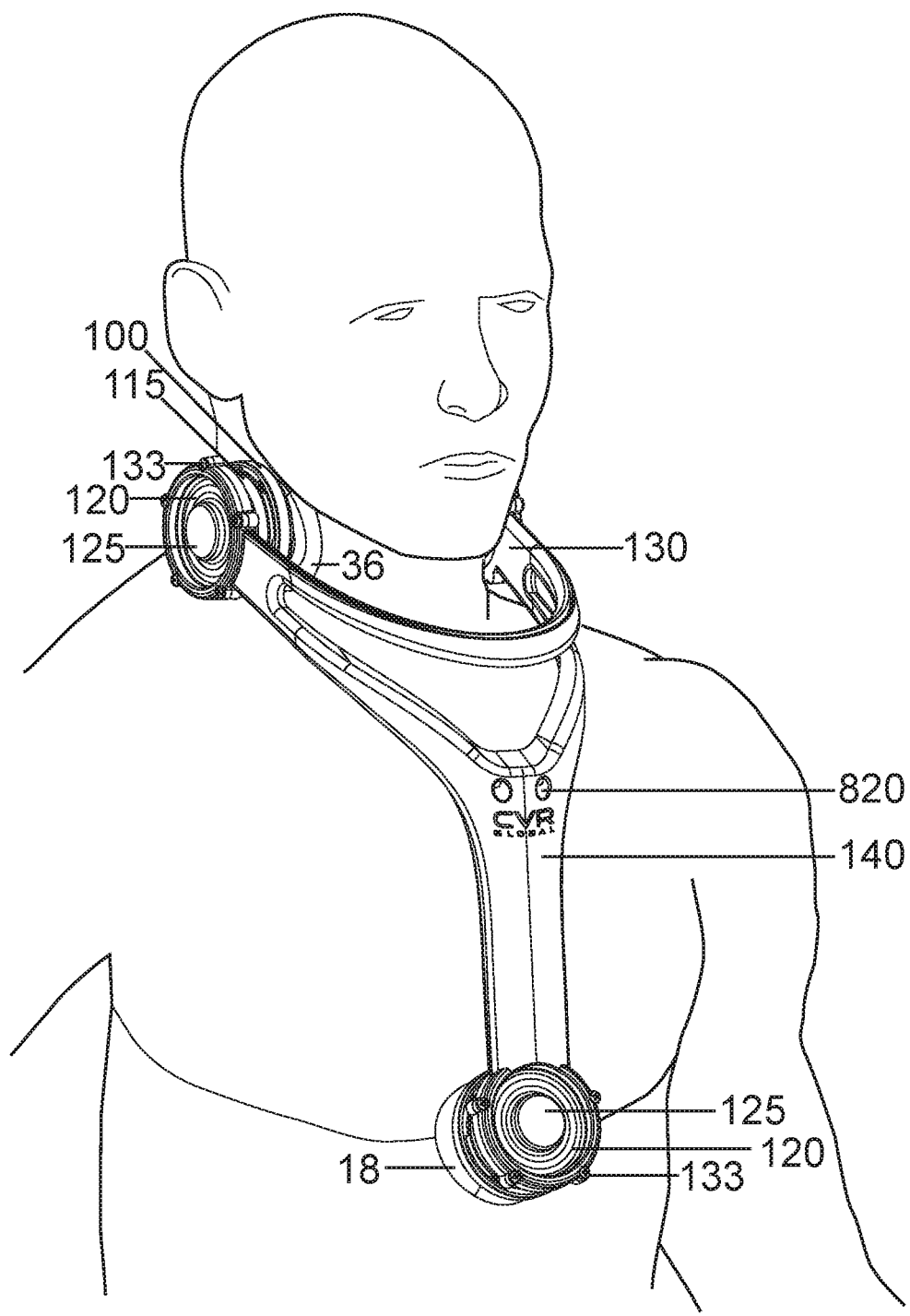
FIG. 11 depicts a sensor array on a person.

In view of FIG. 6, a sensor array is defined comprising a disposable sensor assembly 85, and a disposable sensor pad 18. These two features are replaced frequently, to prevent contamination and error. For example, the sensor can be placed on a patient as depicted in FIG. 11. The yoke 140, 130, and 3 is handheld by the patient during the test. Piezos wear over time and that damage can unfortunately occur from use. Because of the sensitive nature of the piezo, it is necessary to ensure that they are properly functioning before each use. Proper testing protocols utilize a program implemented through a computer, which generates a known set of sounds related to the sounds to be detected on the fluid flow vessel and matches the known played sound to the sounds detected and recorded in real-time by the sensor pods. Where the known sounds and detected sounds match, the sensor pod is confirmed as working to specification. Wherein the sensor pod is not functioning properly, the system will sound an alarm, which will indicate to the operator the need to replace the disposable component. Accordingly, the piezos must be designed to allow for easy replacement of the piezo, while ensuring that the device maintains operation and reliability during ordinary use.

There are several ways in which the piezoelectric elements can wear or be damaged including ordinary and standard use of the device. Ordinary wear may occur as the piezoelectric element wears from ordinary and standard use, and after about 10 to about 400 uses, the piezoelectric element breaks down so that the function and the electrical currents generated are different when comparing the first use to the $2^{nd}$, $5^{th}$, $10^{th}$, $25^{th}$, $50^{th}$, $75^{th}$, $100^{th}$, $200^{th}$, $300^{th}$, or $400^{th}$ use and all numbers in between. Accordingly, to ensure that accurate results are received by each of the units, it is imperative to replace the unit that has worn to maintain consistent results.

Additional wear or breakage can occur to the piezoelectric sensors by error or accident. For example, human error may lead to the array being dropped, or placed onto the base in a manner that breaks, bends, or otherwise damages the piezoelectric unit. Further damage may occur as clean sensor pads are attached and placed against the piezoelectric sensor for use on a patient.

To ensure sanitary use of the device, the sensor pads are replaced between each use of the device. However, because the sensor pads are placed directly onto the piezoelectric unit, there is risk that human error may damage the piezoelectric sensor, either by too much force, or simply through improper pressure applied to the piezo when installing or removing a sensor pad.

Ordinary wear or accidental damage is tested through routine quality control procedures performed in a self-diagnosis module. The sensor pods can be placed in a base or holding device that comprises a speaker embedded within the base which provides a predetermined sound that can be measured by each piezoelectric sensor. When the sensor device is activated for use, the sound, which can include both audible and inaudible sound waves, is played for between about 1 and about 20 seconds. During the time that the sound is playing, each of the piezoelectric sensors records the sound and a program then confirms that each of the three sensors is recording the appropriate sounds being played. If each of the three sensors detects the appropriate sounds, then the sensor device is ready for use. However, if one or more of the sensors detects sounds that do not match with the predicted sounds, the device will provide an alert, which may include lights, sounds, or other display elements, to alert the user of the device that one or more of the piezos needs to be replaced.

An optional display screen attached to the base can further display the device and identify the sensor pod containing the piezo that failed the QC test. Another manner for identifying the failed sensor is to have lights that correspond to working or failed tests either on the base or on the sensor array itself. Once the failed piezo is identified, the user can then replace one or more of the components, as described herein, and then perform the QC test again to ensure that the device is now ready for use.

Accordingly, in a preferred method, a piezo is replaced every 10 uses to ensure that there is no noticeable wear and tear on the piezo, and to prevent the possibility of erroneous data. Accordingly, the sensor device comprises a counter wherein the number of times that a test is run with each of the piezo is counted, so that the sensor device notifies a user that the piezo needs to be replaced, even if each of the piezos are working properly.

In other embodiments, the piezos can be replaced every 1, 2, 5, 10, 25, 50, 75 uses, 100 uses, 125 uses, 150 uses, about every 200 uses, or about every 400 uses or a number in-between. The particular number of uses for each piezo will be determined through additional use of the devices in normal practices. However, to ensure sanitary and consistent results, it is preferred that the piezos are changed after no more than 100 uses.

To facilitate easy changing of the disposable piezo assembly 85, the disposable piezo assembly 85 is able to easily attach to an underlying disposable sensor base 86, and to be replaced. For example, a simple threaded attachment mechanism allows the sensor pod to be removed from the sliding sensor pod base, which is attached to the sensor array. Alternatively quarter, or half-turn attachment means, magnetic attachment, and others as known to one of ordinary skill in the art are known.

FIG. 6 depicts a sensor array comprised of an inner array half 130 and an outer array half 140. The halves are secured together with threaded fasteners 134 and 133, though adhesives, snap fits, or plastic welding can be utilized for securing means. At the bottom of the array is a first sensor pod, depicting a locking cap 125 and a DBM 120 with a sensor pad 18 positioned on the obverse side, with a threaded fastener 133 securing said membrane in place. The DBM 120 is an elastomeric member, with or without articulating bellows geometry, containing an inner opening and an inner and outer flange, suitable to secure the DBM to an array, and to allow for the sensor pod to move freely on said array. The DBM 120 may also be attached to 130 or 140 via insert molding.

Near the vertex of the Y is a charging port, 820, and a PCB charging contact 131 disposed therein. This allows the array to be placed into a charging port and charge a central battery.

Attached to the array is a sensor pod, made up of the components of a locking cap 125, a DBM 120, a PCB processor board 110, a PCB housing 115, a piezo cap 100, a piezo 90, and a disposable piezo assembly 85. These features are further detailed below. A disposable sensor pad 18 can be affixed to the piezo 90 via adhesives or by the natural adhesion of the pad material. For example, the piezo cap 100 can be attached to the PCB housing 115 in several ways, including as in FIG. 1 with a quarter turn feature, comprising a recess 101 and a locking feature 116 having corresponding openings to the pins on the piezo cap 100. By securing these together, the spring pin 111 is engaged and provides electrical contact between the components to power the piezo 90 from an internal power source. Features 101 and 116 can be swapped, provided they are maintained as a matching pair, to allow for selective attachment and detachment of the disposable piezo assembly 85. A recess is provided in the top of the piezo cap 100 for mounting the piezo 90 via pressure sensitive adhesive 92. The recess contains a flange which supports the circumference of the piezo 90 within the piezo cap 100. This recess also allows the piezo to sit about flush with the top of the piezo cap 10, for placement of the sensor pad 18.

Figure 7:
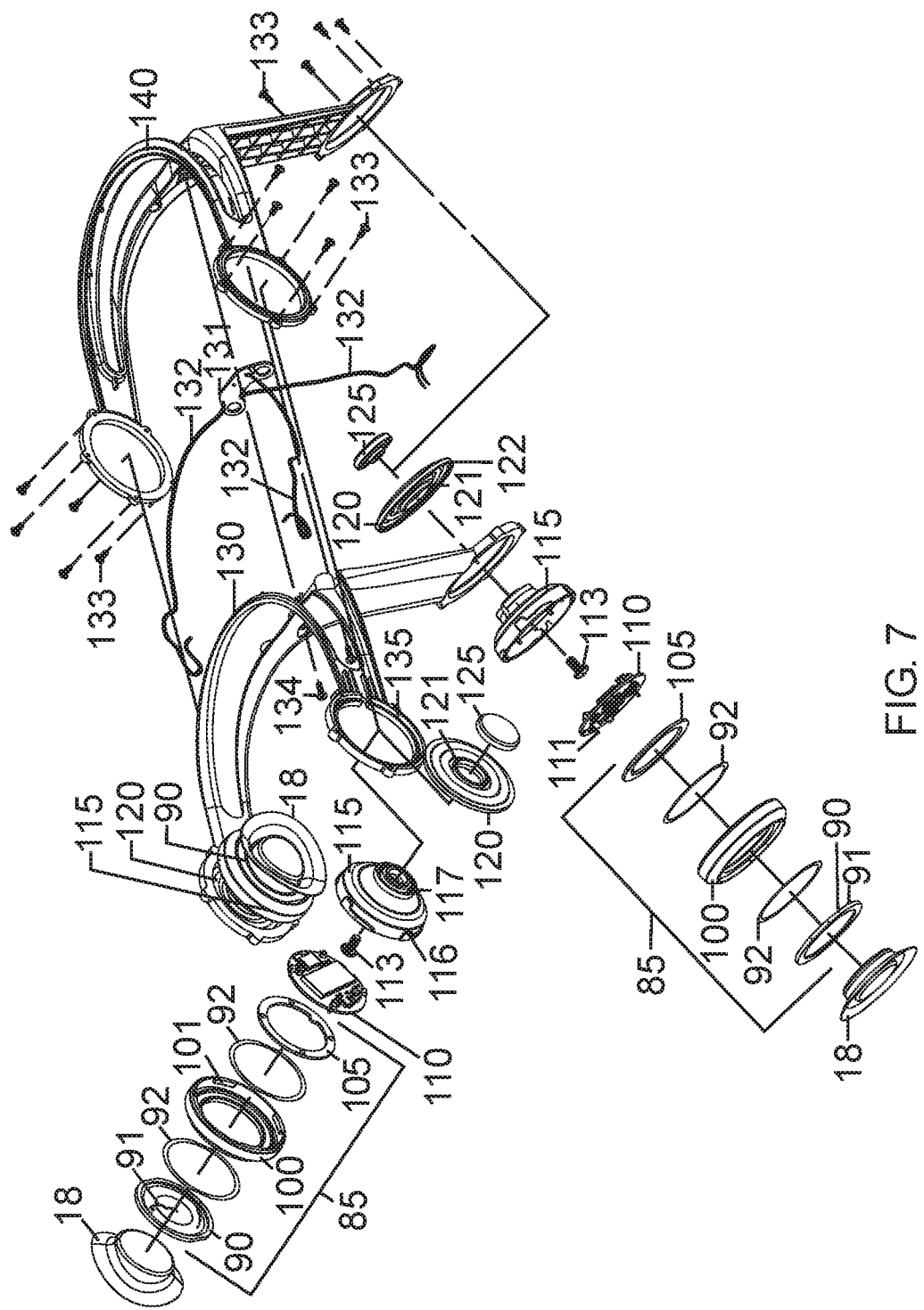
FIG. 7 depicts an exploded view of a sensor array and piezo pods.

FIG. 7 provides a further exploded view of FIG. 6. A disposable sensor pad 18 is provided to be attached to the disposable piezo assembly 85. The assembly 85 comprises a piezo wiring 91 which connects the piezo 90 to the PCB contact board 105. Two pressure sensitive adhesives 92 are provided, one connecting the piezo 90 to the piezo cap 100 and another adhesive 92 connecting the piezo cap 100 to the PCB contact board 105. These components make up the disposable assembly 85.

In one embodiment, this disposable assembly 85 is the smallest disposable component, which allows for quick and easy replacement of the piezo without replacement of any further components (except for the disposable sensor pad 18, which is replaced for every use). The disposable assembly 85 comprises a quarter turn locking feature 101 that corresponds to a paired feature 116 on the PCB housing 115. This allows for a small turn of the disposable assembly 85 to remove the component and replace. Additional attachment mechanisms can be easily exchanged, for example magnetic, threaded engagement, or simply a threaded fastener or two that can be engaged for replacement. Finger capable fasteners can use a full, half, or quarter twist to secure a fastener between two components. A person of skill in the art will recognize that numerous options exist for attaching and detaching such components and that attaching means incorporates these listed and additional options not described in detail herein.

The PCB housing contains a locking groove 117 that engages with and locks the elastomer DBM 120 to the PCB housing 115. In particular locking groove 117 engages locking key 121 between the locking cap 125 and the PCB housing 115. A locking cap 125 engages to a fastener 113 to secure the key 121. A second key 122, is also provided to lock the DBM 120 between the outer array housing 140 and the inner array housing 130. A further detail of these locking features are provided in FIG. 12.

While the disposable assembly 85 can be easily removed and replaced, it is also contemplated that the entire sensor pod can be removed and replaced easily. For example, removal of threaded fasteners 133 will allow for quick and easy replacement of the entirety of the pod, inclusive of the DBM 120. Furthermore, the DBM 120 can be held in place, and the locking cap 125 can reveal a threaded fastener 113 to replace the remaining components. In the Fig, the fastener 113 can be oriented in either direction to allow for quick replacement.

FIG. 7 further details components of the array including a PCB charging contact 131, connecting a wiring harness 132 to each of the piezo sensors 90. A battery, not depicted, can be positioned within the array handle to power the devices, or can be attached directly to an AC or DC power source with a wire.

Figure 8A:
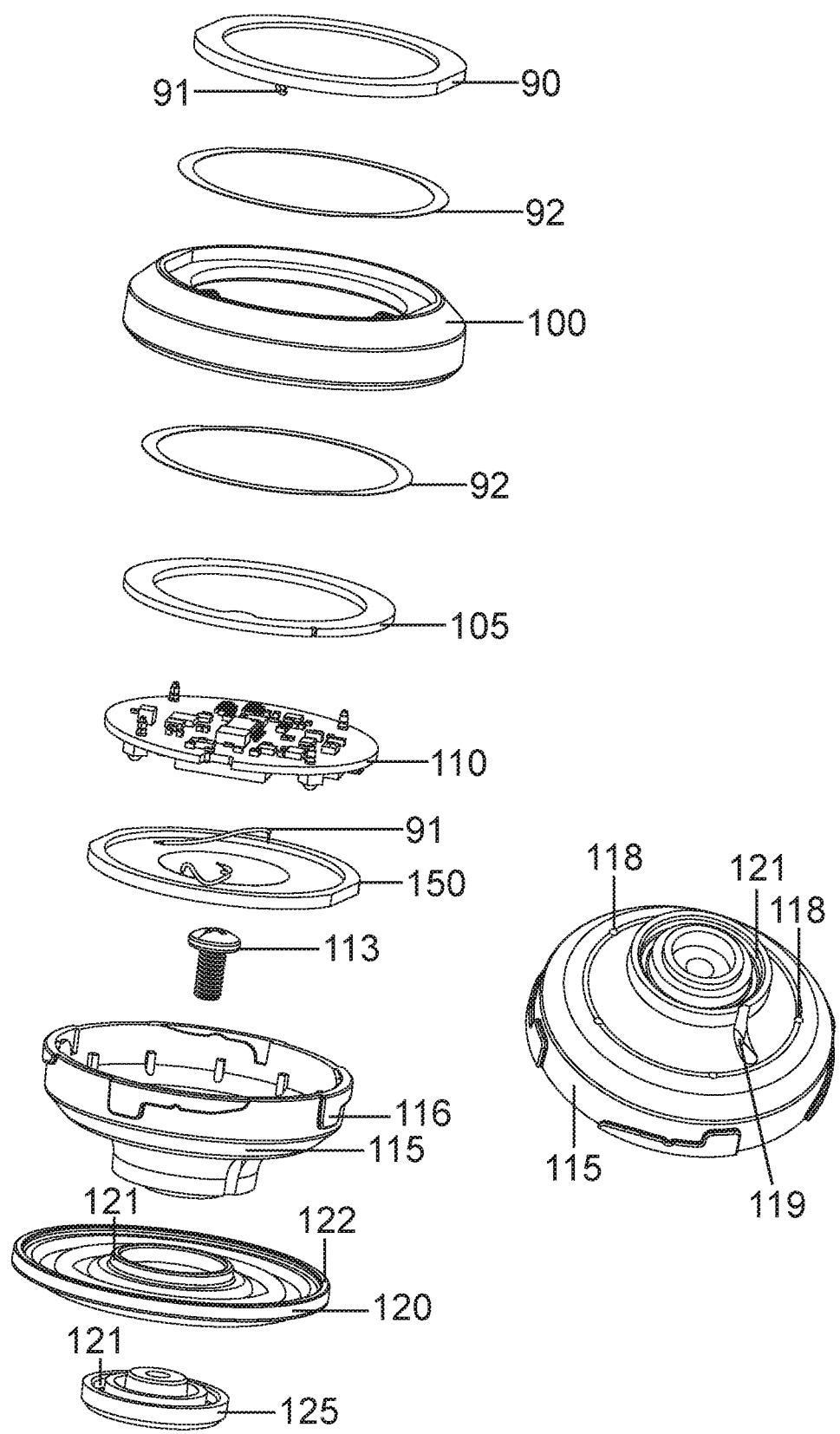
FIGS. 8A and 8B depict an exploded view of a piezo pod with bellows membrane.
Figure 8B:
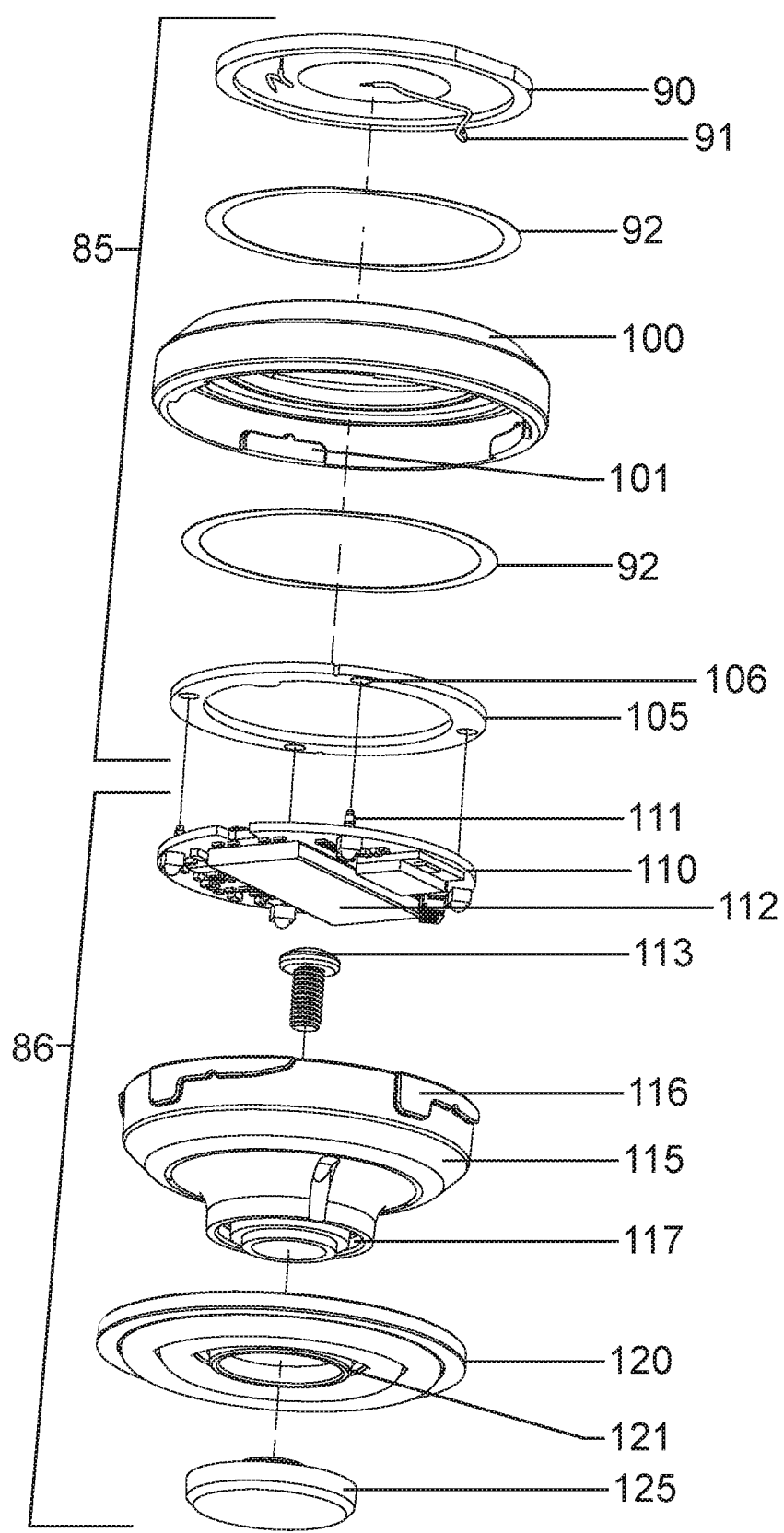

FIGS. 8A and 8B depict further exploded views of a sensor pod. FIG. 8A specifically defines a dual piezo mechanism, wherein a second piezo 150 is attached to the rear of the PCB processor board 110 to allow for noise cancelling. Briefly, though described above, FIG. 8A depicts a piezo 90 a pressure sensitive adhesive 92, a piezo cap 100. The adhesive 92 engages the flange of the cap 100, and said flange supports the piezo 90 at its circumference. A second pressure sensitive adhesive 92 is positioned inside of the piezo cap 100 and engages to the PCB contact board 105, which contacts a PCB processor board 110. A second piezo 150 is engaged on the rear of the PCB processor board and a wiring 91 attaches the piezos to the PCB processor board 110. A threaded fastener 113 secures the PCB housing. The detail of the locking features 121 and 122 are best seen in a later figure. Sound locking holes 118 are depicted as well as the entrance hole 119 for the wiring harness 132.

FIG. 8B depicts a single piezo 90, a piezo wire 91, the adhesive 92. These combine into the piezo cap 100, which contains a locking feature 101. The second adhesive strip 92 attaches to the PCB contact board. The spring pin 111 is seen positioned to contact the PCB contact 106. A battery 112 is attached to the PCB board 110. A screw 113 attaches the PCB housing to the locking cap 125, which secures the DBM 120. The disposable piezo assembly 85 is combined with the sensor base 86 to form a sensor pod. Each of the disposable piezo assembly 85 and the sensor base 86 are replaceable or disposable, as needed.

Figure 9:
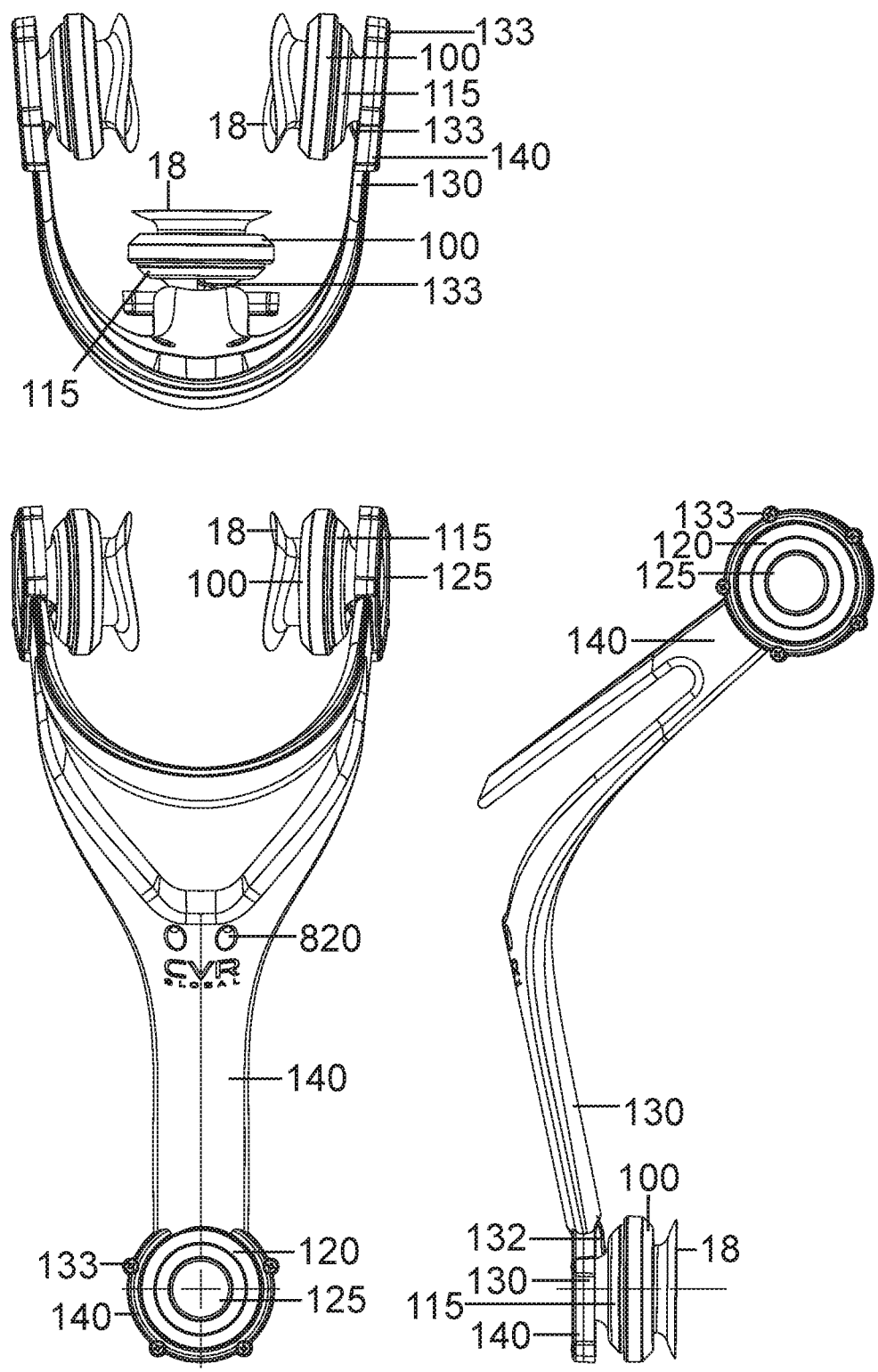
FIG. 9 depicts various views of a sensory array with piezo pods attached.

FIG. 9 depicts several views of an array, with an angled sensor pad 18 positioned on each of the different sensor pods.

Figure 10:
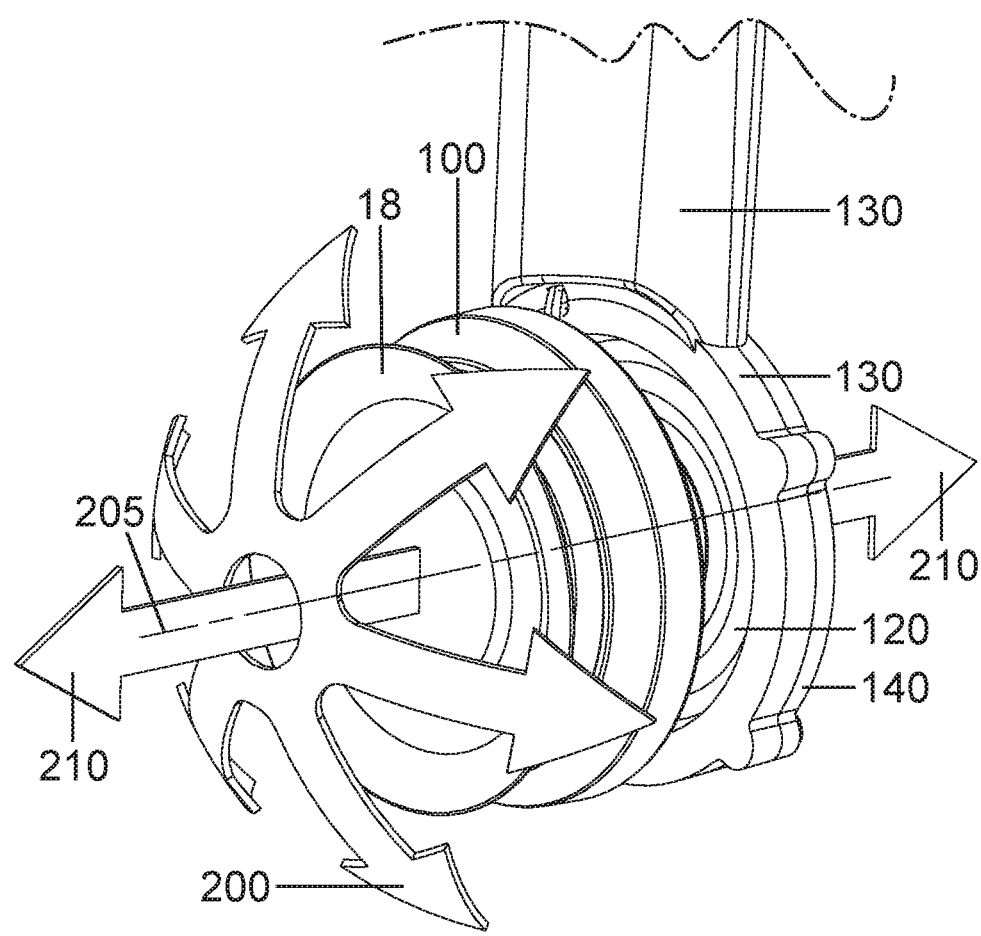
FIG. 10 depicts the movement of a bellows membrane on a piezo pod.

FIG. 10 depicts the possible movement of the DBM 120. The arrows 200 refer to spherical movement of the entire assembly, including the sensor pad 18, and the disposable piezo 85. The centerline 205 is provided, with all features moving in the direction of 210, both forward and backward, as necessary. In this manner, the DBM 120 allows for the entire feature of the sensor pad 18 and piezo 90 to press against a surface and extend away from the surface, but to return back to a central position after use. Furthermore, the spherical movement 200 allows for angular rotation to rotate and angle the sensor pad 18 to best fit against the skin surface of a patient, for example as depicted in FIG. 11. Here, a different sensor pad 36 is used against the skin surface on the neck, as compared to the sensor pad 18 at the torso. Appropriate pads, having different shapes can be used based on the needs of the particular patient.

Figure 12:
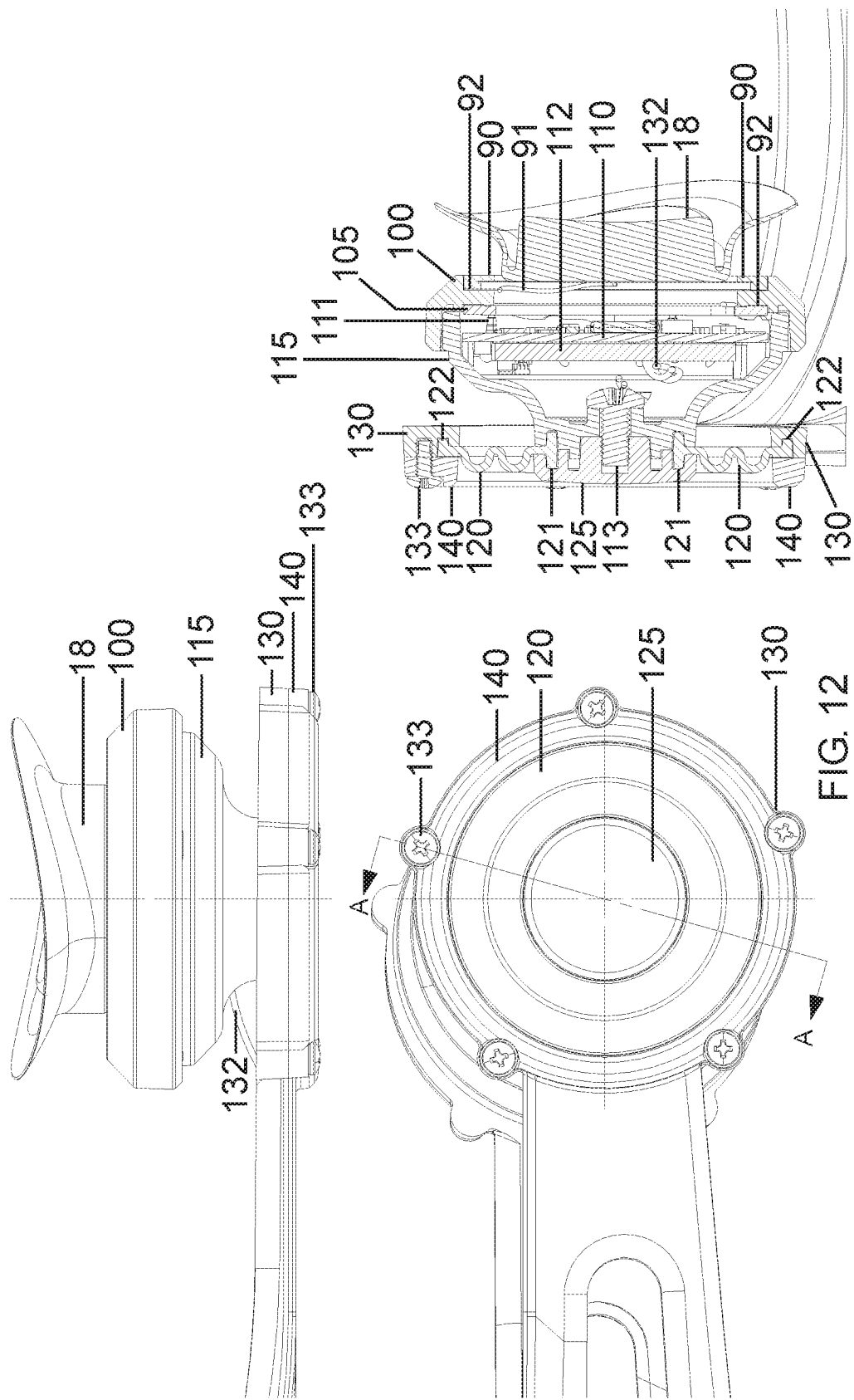
FIG. 12 depicts a side and sectional view of a bellows piezo pod.

FIG. 12 depicts a side profile and cross-sectional view through line A-A, of a sensor pod with DBM 120. The side profile shows a sensor pad 18 positioned above the piezo cap 100, PCB housing 115, the wiring harness 132 and the inner array 130 and outer array 140 connected with threaded fasteners 133. The cross-sectional view depicts a PCB housing 115 engaged to the Piezo cap 100, with the adhesive 92 securing the piezo 90 at the right hand side. The left hand side depicts the inner array 130 secured to the outer array 140 with a fastener 133. By compressing these together, the elastomer DBM 120 is compressed together. For example the locking feature 122 is depicted securing the edge of the membrane 120 between the inner array 130 and the outer array 140. The inner locking feature 121 is secured between the PCB housing 115 and the locking cap 125. A fastener 113 is provided therein. Each side is similar through the cross-sectional view.

The DBM 120 is a circular feature having an inner opening. At the outer edge of the DBM 120 is an outer flange 122. At the circumference of the inner opening, there is an inner flange 121. These flanges 122 and 121 are used to lock the DBM 120 into place between the array features 130 and 140, as well as between the locking cap 125 and the housing 115.

Therefore, the DBM 120 is an elastomeric material, capable of allowing the attached piezo to flex in any direction, as well as move away from the surface to be compressed. This allows for a consistent pressure to be applied to the skin surface by the sensor pad 18, based on the rigidity of the membrane 120.

Figure 13:
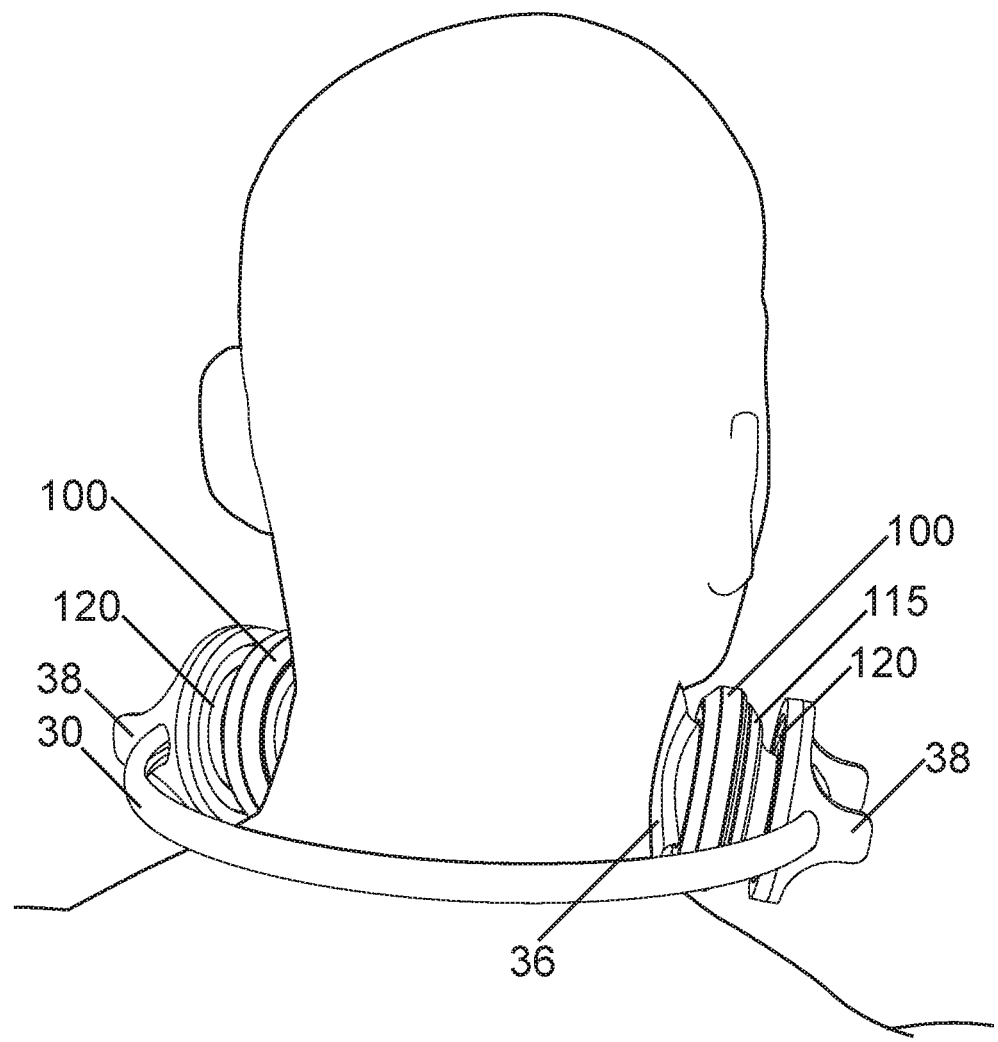
FIG. 13 depicts a rear neck sensor array and two attached slideable sensor pods.

FIG. 13 depicts a rear image of a neck array 30. Threaded on the neck array 30 is a piezo base 38 comprising openings to allow for movement along the neck array 30. Attached to the piezo base 30 is a DBM 120 as depicted in part of FIG. 12, with the difference being features 130 and 140 are exchanged for the components of the piezo base 38. The neck array 30 is a track-like structure, about which the sensor pods can slide on openings in the piezo base 38. The neck array 30 is generally "C" shaped, and when the sensor pods are at the end of the track, are oriented for placement on the carotid artery. However, the sensor pods can be centrally aligned, thus being side-by-side and placed together on an area of interest.

Figure 14:
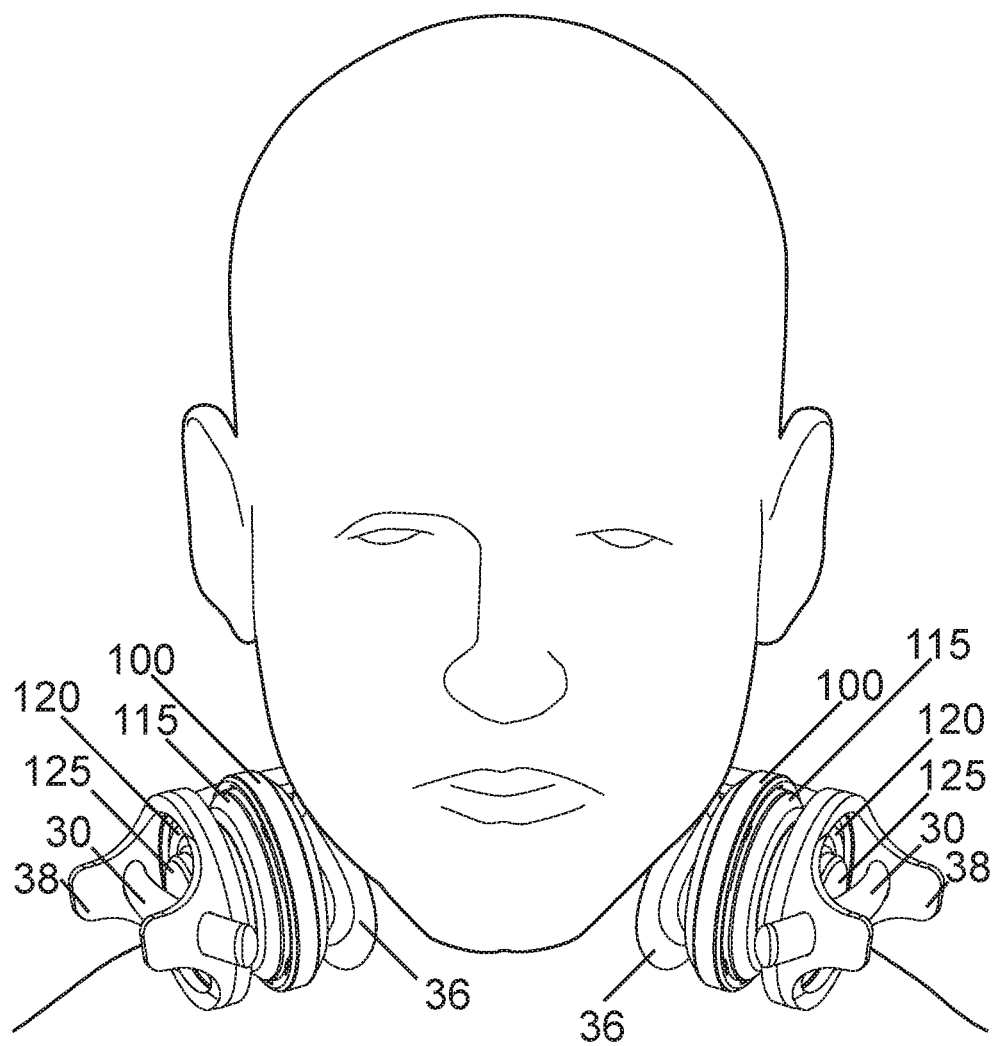
FIG. 14 depicts a front view of a rear neck sensor array and two attached slideable sensor pods.
Figure 15:
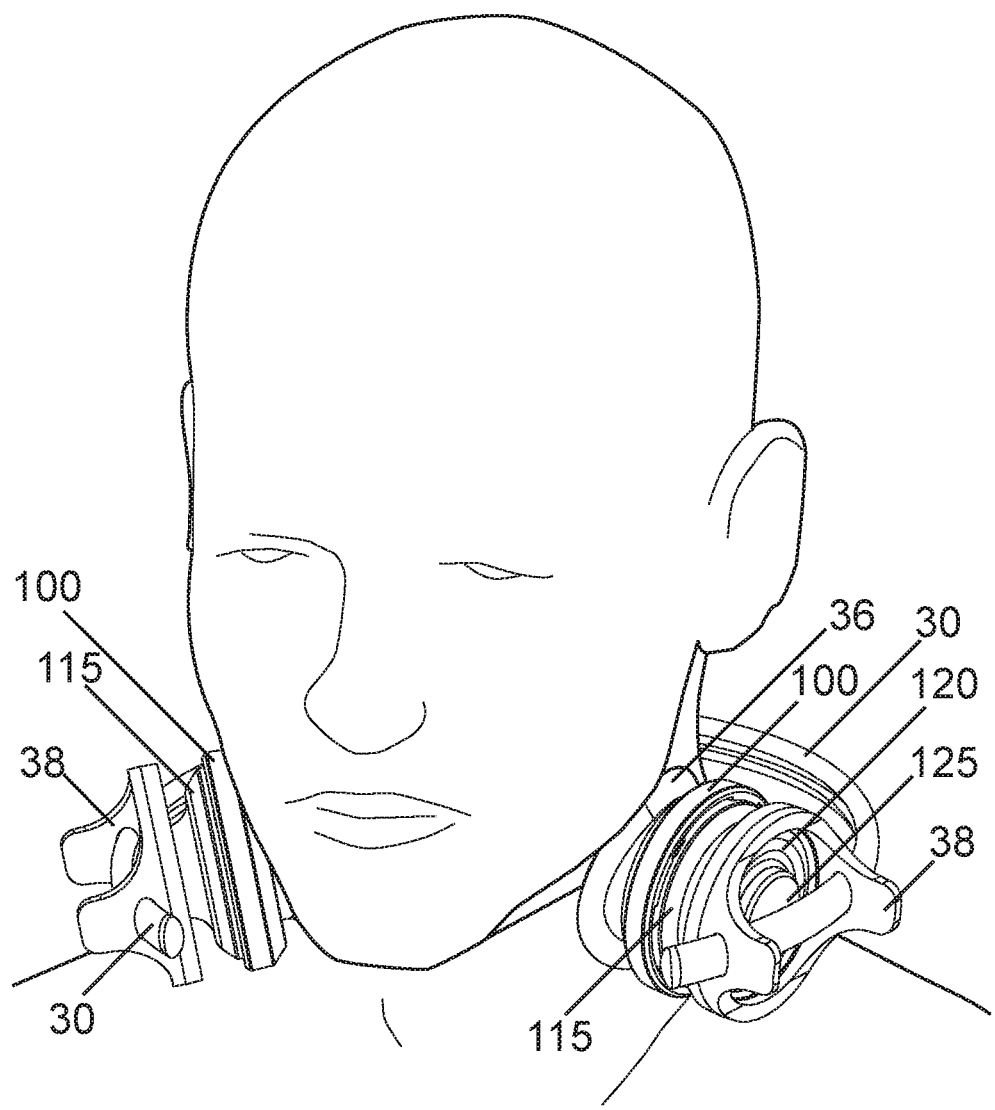
FIG. 15 depicts an alternative view of FIGS. 8 and 9.

FIG. 14 depicts a front view of the neck array 30, which more particularly depicts the piezo cap 100, the sensor pad 36, the PCB housing 115, the DBM 120, the locking cap 125. FIG. 15 provides an alternative view of FIGS. 13 and 14.

Figure 16:
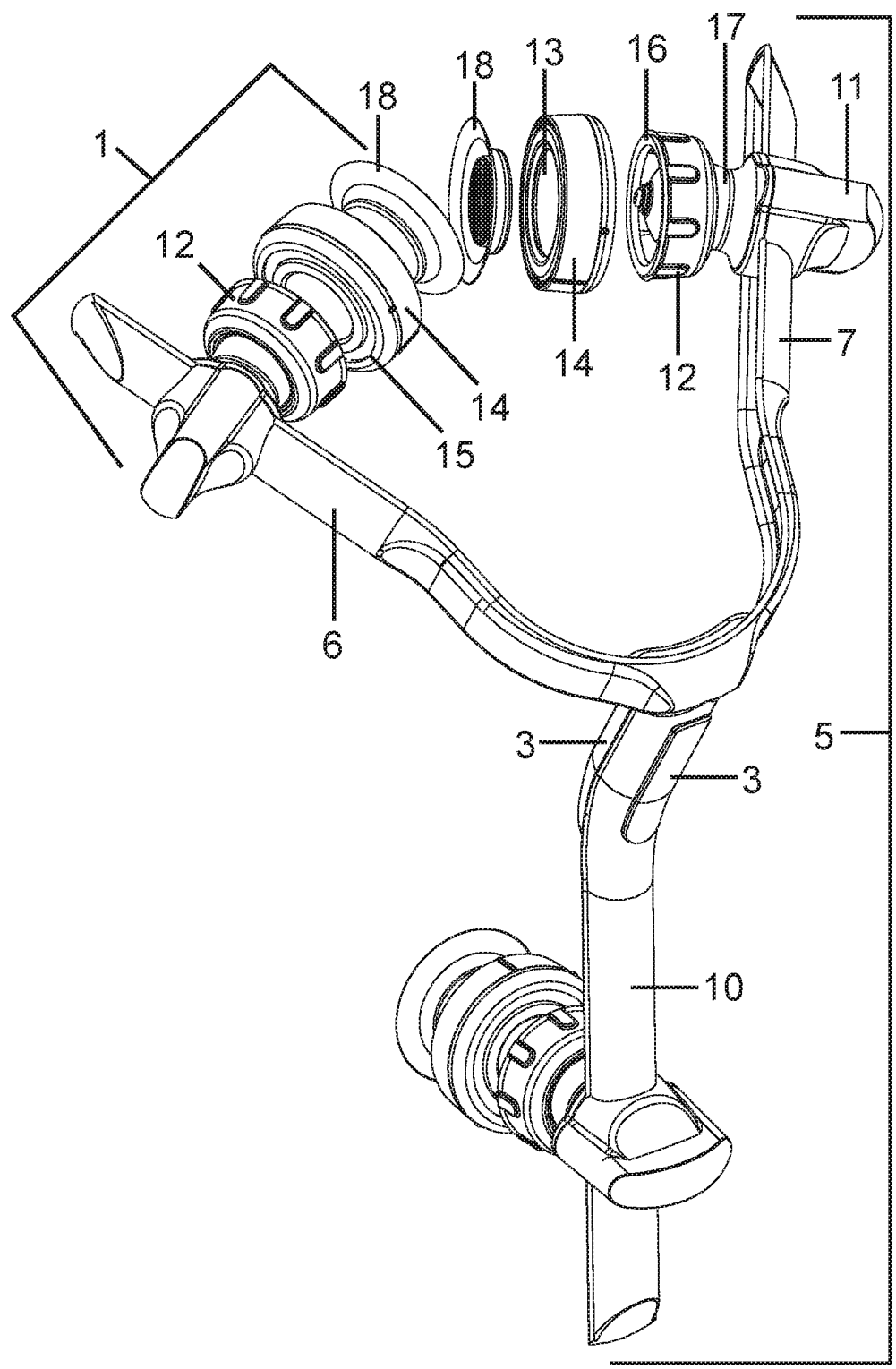
FIG. 16 depict an alternative sensor array and sensor pods secured on the array, with a partial exploded view of certain disposable components.

FIG. 16 depicts a variation of an array 5, having a stem 10, a left arm 6 and a right arm 7. Like the neck array 30, this embodiment of an array, comprises a pod sled 11, which allows the sensor pods 1 to move along the arms 6 and 7 or the neck 10, to allow for fit of these sensor pods 1 on a patient. A rear pod mount 12 comprises attachment means 16 which secures to the piezo cap 14. For example, the attachment means 16 may be a quarter thread, pin and recess. Alternative is a paired threaded fastener, a set of magnets, threaded fasteners having an opening in one end and threads in the other. A piezo 13 is depicted at one end, and the sensor pad 18 can be placed on said piezo. Rotation of the rear pod mount 12 will remove the piezo cap 14 and included piezo 13. Alternatively, the pod sled 11 can be rotated in a quarter, half, or full turn to separate from the sled ball 17, and remove the entire part of the sensor pod 1 or be attached with mechanical fasteners 415. Accordingly, easy removal is possible for either just the disposable piezo component 13, or for the entirety of the sensor pod 1, by removal of the pod sled 11.

In an ideal world, every patient would be the same shape and size, and modification of the structure would not be required. However, in practice, men, women, and children have significantly different shapes and sizes due to the amount of body mass, muscle, breast tissue, fat deposits, etc. Specifically, changes in body mass and shape between the neck and the torso create issues where the array must be modified to position one or more sensors in appropriate positions for acoustic sensing.

Therefore, as used on human patients, a difficulty in such devices is that people come in all shapes and sizes and that the array must be easily modified to fit these different shapes and sizes. One option would be to utilize different sized, fixed position sensing elements, due to the fragile nature of the sensing elements. However, constant movement and replacement of the sensing elements from one device to another would likely result in more damage to the sensing elements and increase the risk for the need for frequent replacement of these elements. Therefore, an array with rails, both the neck and "Y" versions, provides the necessary stability and flexibility provides a great advantage in the array for use on patients.

A particular feature of the sensor pods when affixed to an array is that they are adjustable and can be configured to account for the anatomical differences between individuals while remaining sufficiently rigid to support the sensing elements. Such flexibility can be seen in the depiction of FIG. 10 or in the angled pod, in FIG. 17.

Figure 17:
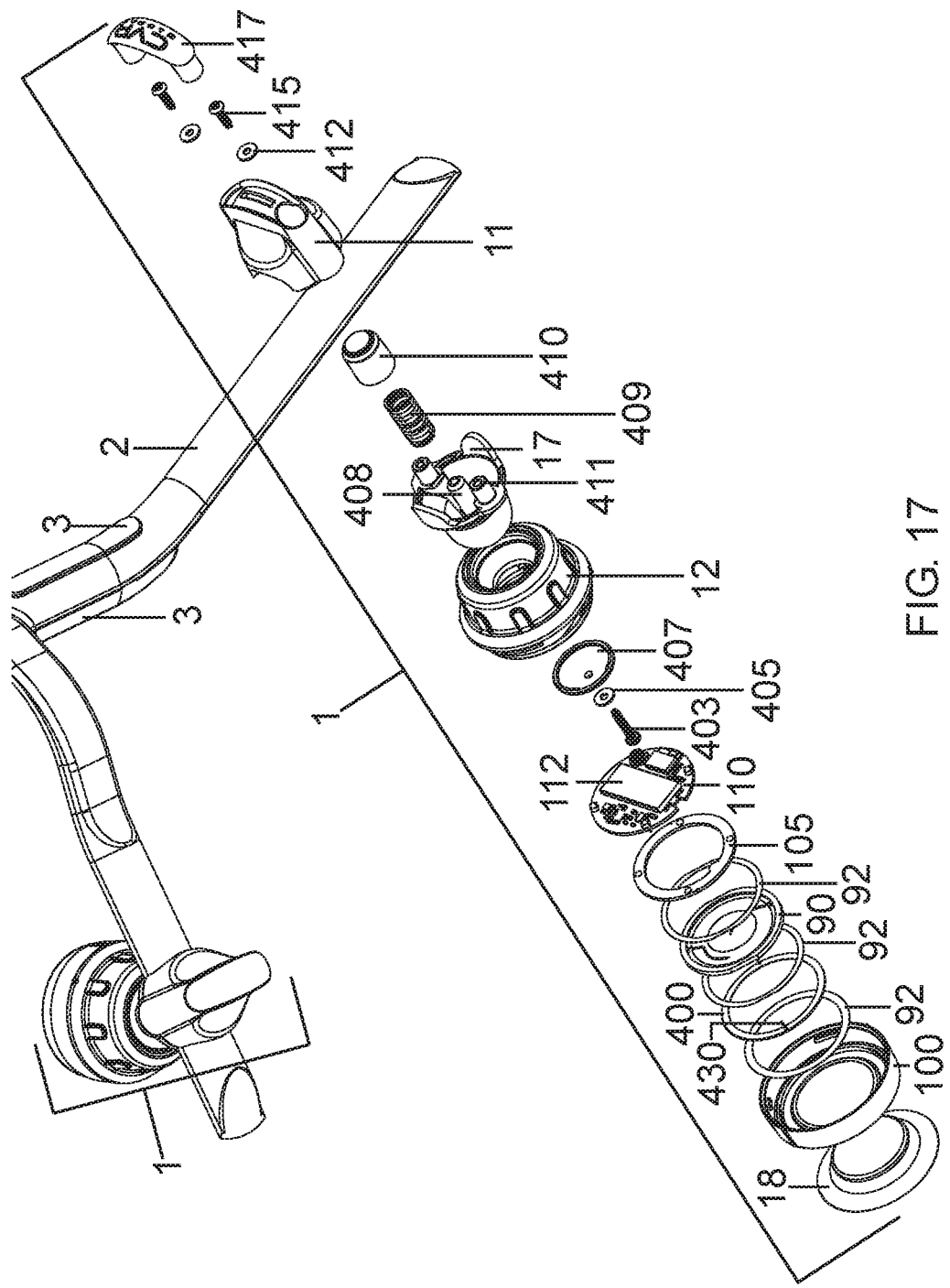
FIG. 17 depicts an exploded view of a sensor pod having sliding means on an array.

The exploded view of FIG. 17 details a variation of a sensor pod 1, showing the components that make up the sensor pod 1 able to slide along the array. The sensor pad 18 attaches to the piezo 90 via adhesives or the natural adhesion of the material. Within the piezo cap 100, receiving charging coil 400 attaches to inside of 100 with a pressure sensitive adhesive 92. Piezo 90 attaches with pressure sensitive 92 to receiving charging coil 400. PCB contact board 105 attaches via pressure sensitive adhesive 92 to piezo 90. The receiving charging coil 400 makes electrical contact with the PCB contact board 105 with a soldered or crimped connection along wires 430. A PCB processor board 110 is then compressed adjacent into 12 and makes electrical connection via spring pins 111 to PCB contact board 105. The sensor pad 18 fits within the piezo cap 100, which is attached to a pin board 400 with a pressure adhesive 92. Another adhesive connects the board to the piezo 90, and another adhesive connects this to the PCB contact board 105. A fastener 403 with a washer 405 compress with a friction washer 407 into the knuckle 12. A sled ball 17 allows rotation of the piezo when mounted, held, in part, by the friction of the knuckle 12 and the friction washer 407. A spring 409 compresses against spring cap 410 and sled ball 17 when pod sled 11 is assembled to sled ball 17 via washers 412 and threaded fasteners 415, creating frictional pressure against the inside surface of array arm 2. This allows for very easy positioning of the pod assembly 1, anywhere along array arms without actuating any mechanical buttons. Fasteners 415 can be excluded for attachment means, such as quarter-turn, half-turn, full-turn threaded attachment, magnetic, or other similar attachment means, to allow for easy removal of the sensor pod. Alternatively, the sensor pods can simply slide off of the end of the senor, and a new one replaced by sliding it into place. The spring 409 holds the sensor pod into place during use.

Figure 18:
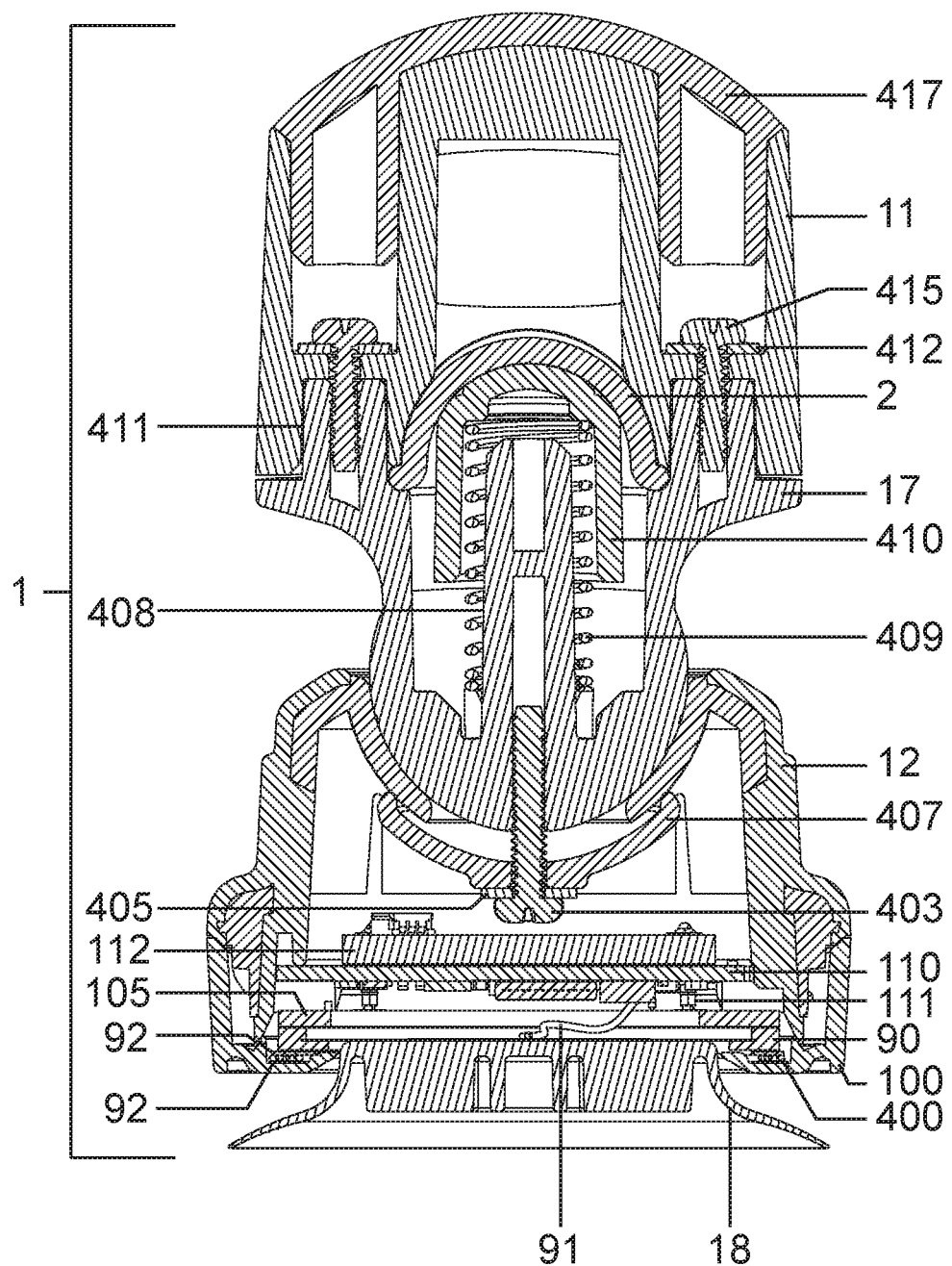
FIG. 18 depicts a cross-sectional view of a slideable sensor pod.

FIG. 18 depicts a cross-sectional view of FIG. 17.

Figure 19:
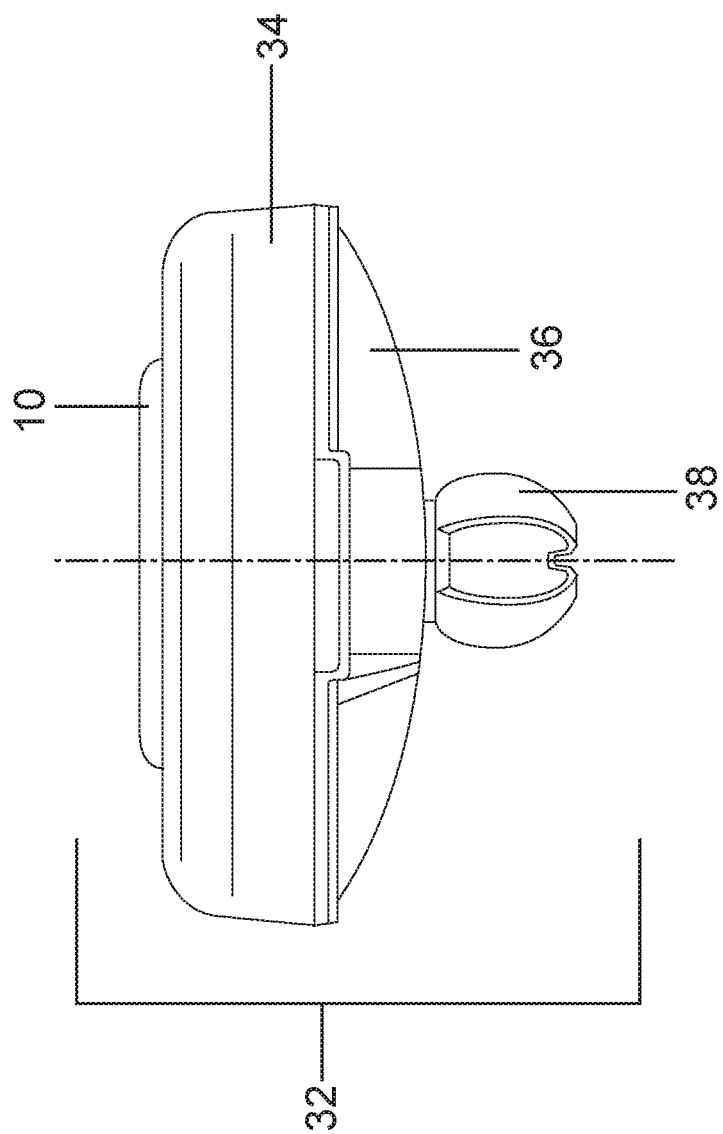
FIG. 19 depicts a disposable sensor pod with pin mount.

FIG. 19 depicts a sensor pod having a pin mount 38. This pin mount can engage to a ball mounting system, to allow for rotation of the sensor pod. A corresponding ball recess can be provided to allow for such attachment means and rotation. The fastener acts as a ball and socket, allowing rotational movement.

Figure 20:
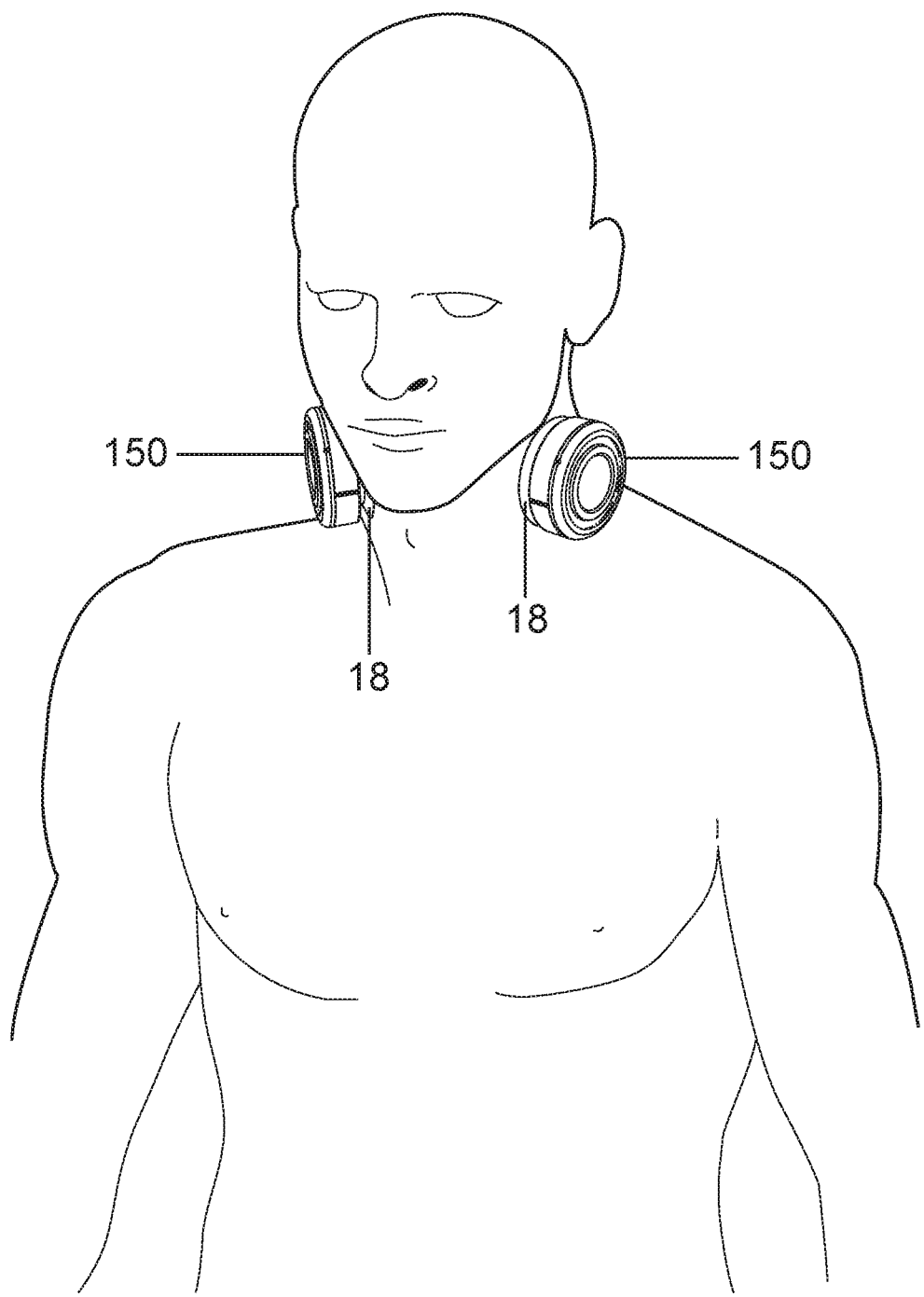
FIG. 20 is a view of two piezos without an array.
Figure 21:
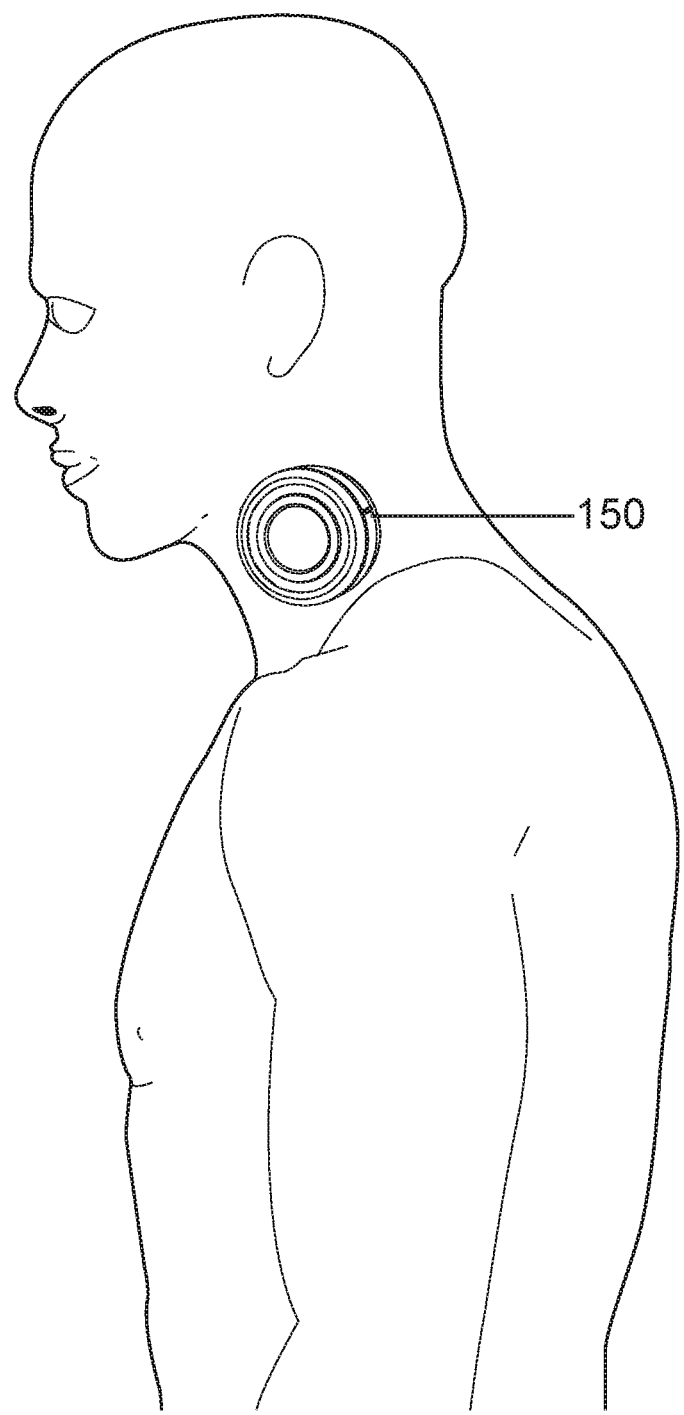
FIG. 21 is a side view of a piezo without an array.

FIGS. 20 and 21 depict a piezo pair that does not utilize an array. Accordingly, the piezo 150 relies upon an adhesive surface on a sensor pad 18 to allow the piezo to stick to the skin surface. In certain embodiments, it is advantageous to perform a test with one piezo at a time, with the patient laying in a position to allow for the piezo to rest with gravity. Thus, the adhesive does not need to be so strong but rather merely sufficient to hold the piezo into a relatively stable position. This may be useful for situations where an array is impracticable, whether due to the dimensions of the patient, surgical procedures, or the like, that would restrict access of an array. Furthermore, by eliminating the array, a further source of noise may be eliminated from the data sample.

FIGS. 22 and 23 depict a gel pad with cylindrical surface 600 that contacts with the piezo film 602. The upper frame 601 supports the piezo film 602, and engages with an adhesive 603 to the lower frame 604. A wiring harness 605 and solder or welds 606 connect the wiring harness to the piezo film 602. The lower frame 604 has a concave surface, and the piezo film 602 engages with this curvature resulting in a piezo having a concave surface. The concave surface allows for increased reception of both high and low frequencies, thereby increasing sensitivity in certain instances, wherein peaks may be identified at these margins.

FIG. 22 particularly depicts the cross sectional view and side view of the film piezo 602, while FIG. 23 depicts the exploded view.

A curved film piezo can be exchanged for any of the piezos in embodiments described herein. For example, the lower frame 604 may comprise a relevant attachment means, and further comprise a PCB contact point to allow for direct exchange with prior examples and figures.

Figure 24:
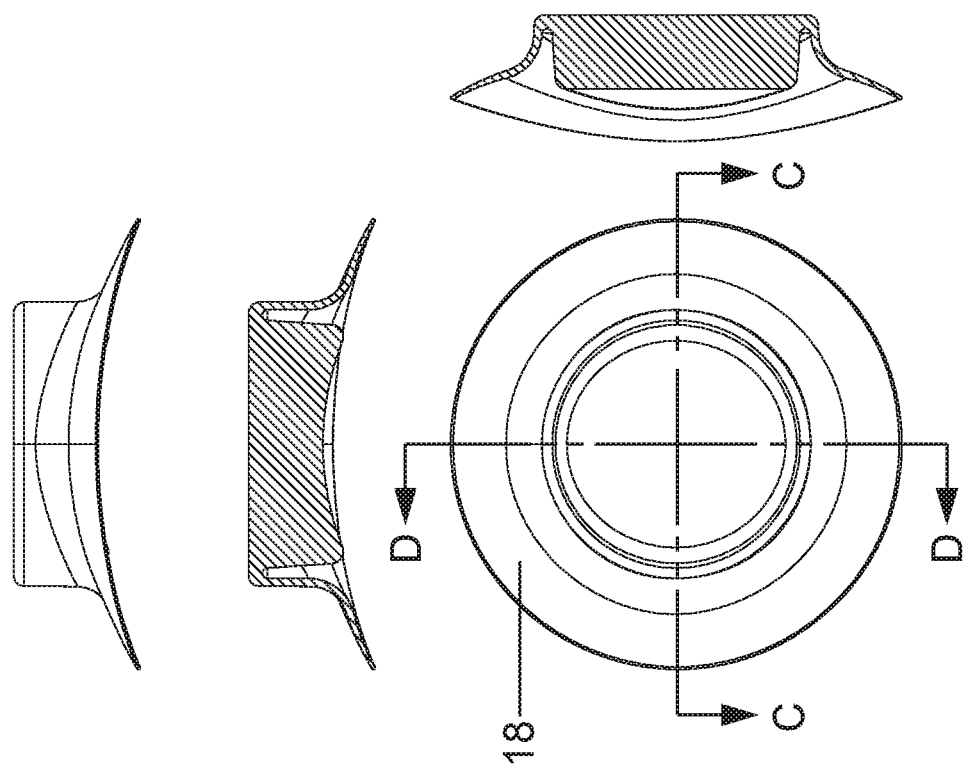
FIG. 24 depicts non-symmetrical sensor pads.
Figure 24:
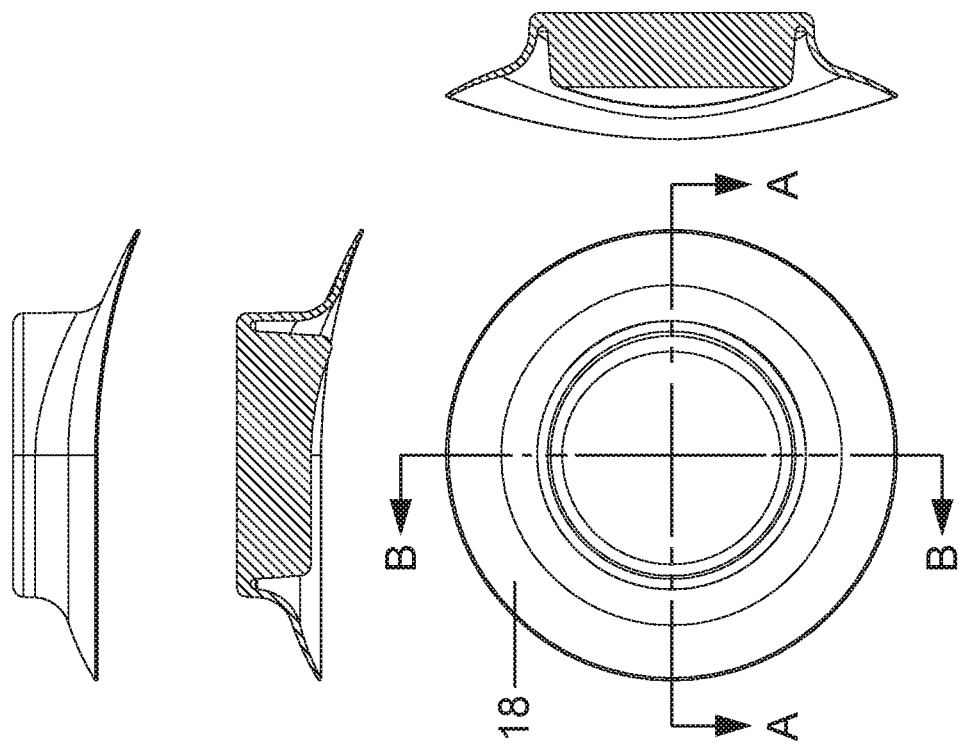

FIG. 24 depicts two different sensor pads 18 for use in an array with a piezo sensor. The sensor pads are angled at the skin facing surface, such that on the left hand side, the curvature on the bottom right engages to an angled structure to ensure a good acoustic fit. By contrast, the sensor pad on the right hand side of the page comprises a dual concave structure, to fit around a structure that is rounded. In each case, there is a proper fit, and so the sensor pod must be able to rotate to allow the sensor to be properly fit against the skin to achieve a proper acoustic contact for data collection. Cross-sectional views of the left and right sensor pads are depicted for clarity.

The sensor pods including both 85 and 86 components, are replaced, as necessary to allow for proper functioning of the piezo sensor. These replacements are performed as necessary, but at least every 10, 25, 50, 75, 100, 150, or 200 tests. When the sensor base 86 is replaced, the disposable piezo assembly 85 is also replaced. By contrast, in each test, sensor pads 18 are replaced.

In certain preferred embodiments, the sensor pads 18 can be secured onto the piezoelectric unit via an adhesive, such as one of several common low tack adhesives for providing for a temporary securing of the sensor pad to the piezo element. Other embodiments may utilize a gel or other water or solvent based material that may secure the sensor pads without the need for an additional adhesive material. In further embodiments, the sensor pad fits into the sensor pod and secures onto the piezo without the need for any adhesive.

A particular feature of the sensor pads described in the embodiments herein is the fact that the top face shape (that contacts the patient), and the bottom face shape (that contacts the piezo) are made so that when the top face contacts the patient and thus applies pressure to the sensor pad and through to the bottom face, the piezo does not flex when pressure is applied to the sensor pad. This is important to ensure consistency and accuracy of the piezo device. Therefore, the sensor pad, in certain embodiments, is designed such that the piezo does not flex when pressure is applied to the sensor pad. In a further preferred embodiment, the piezo flexes less than about 0.1%, 0.5%, 1.0%, 5.0%, 20%, and 25% and all percentages in between. Accordingly, in certain embodiments, the amount of flex is greater than zero (i.e. rigid and does not flex), but the amount of flex is minimized to maintain accuracy of the piezoelectric unit.

It is also preferred that the sensor pads create a proper impedance matching with a patient. Accordingly, the sensor pad is designed to have a slight tackiness which ensures a proper impedance matching with the patient, which then successfully transfers sounds through to the piezo element so that the piezo can properly detect vibrations and noise signals from the patient.

Therefore, in order to maintain both sterility of the medical device and proper function of the medical device, it is necessary to provide replaceable components. The entire device is a complex system comprising a display, a base unit, an array, a sensor base, a disposable piezo assembly, and a sensor pad. Each of the last four are disposable. The array itself can be disposed of after a number of uses, likely between 100-1000 uses. The array may lose elasticity to ensure proper fit on a patient, gain cracks, or simply lose stability. Each of these may increase variability and thus replacement is warranted.

Figure 25:
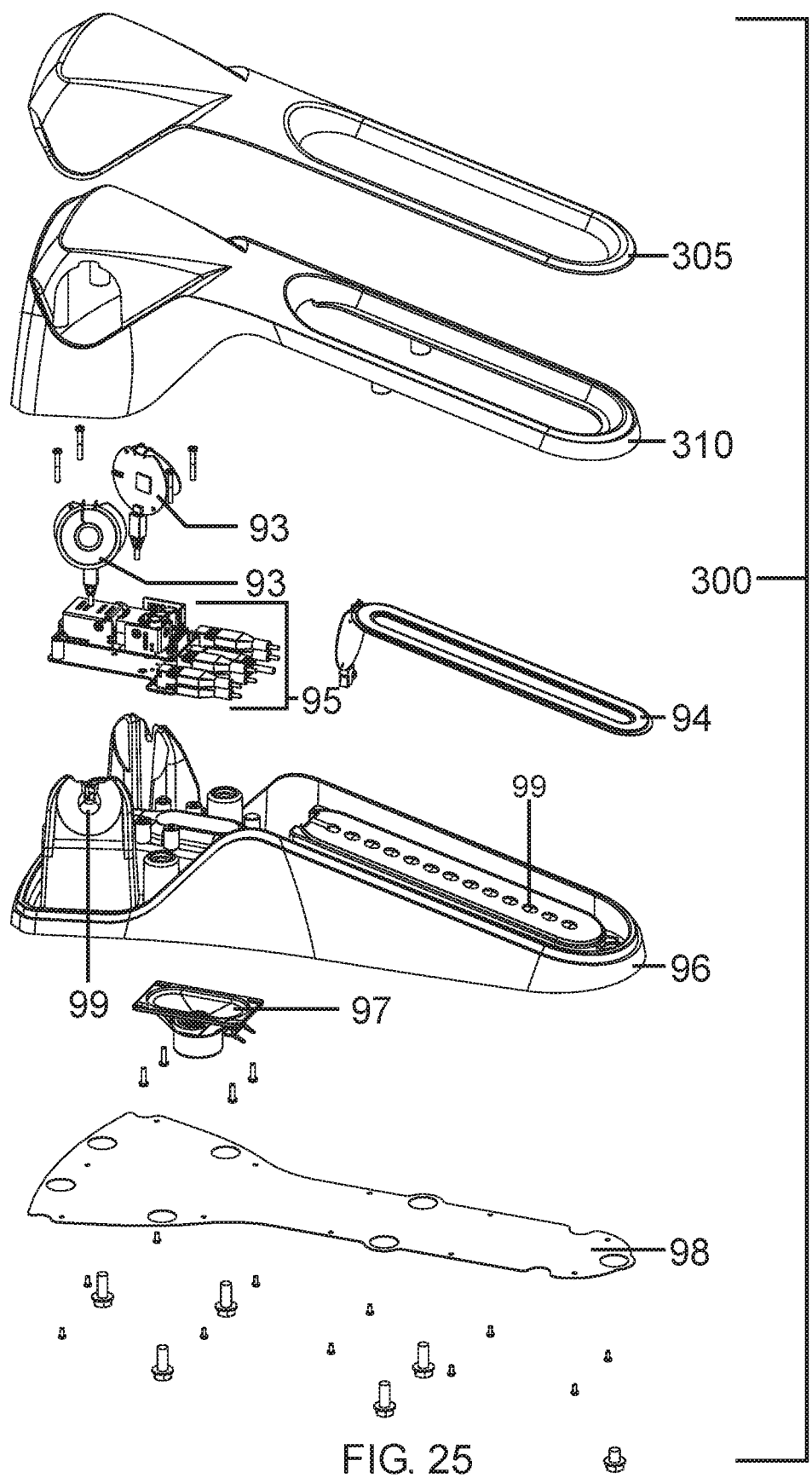
FIG. 25 depicts a base.

The sensor base as depicted in FIG. 25, comprises attachment means for the sensor pod to the array, and comprises electronics for connecting the sensor itself, typically a piezo, to the device. The base, using certain elastomeric materials to allow for movement of the sensor pod, will wear with time, necessitating replacement for minimizing variability.

The disposable piezo assembly is intended for more frequent replacement than the base or the array, as the piezo is susceptible to wear or damage. Accordingly, frequent changes, such as between every use and every 10, 25, 50, or 100 uses is necessary for accurate results.

The device is a complex system comprising multiple components, each working together to ensure that accurate results are obtained. Disposable components ensure that the system works properly, every time, and that it generates accurate and reliable data.

A kit is envisioned with the system, wherein a plurality of sensor pads are provided, a plurality of disposable piezo assemblies are provided, at least two sensor base assemblies, and at least two arrays. Said kit can be used with a system comprising the base and a display, as well as necessary software and hardware for energizing and running the device through its necessary protocols.

Quality Control Methodologies and Devices

Now that we have a device that is clean and has readily replaceable components, we need to ensure that the device is properly functioning. Accordingly, we describe certain methods and embodiments that provide for self-diagnostic tests, active diagnostic tests, and guidance for properly positioning a sensor on a patient.

The quality control protocols embodiments provide for a process or method for determining if a listening device, such as a piezoelectric device, or microphone, is properly functioning. This is a self-diagnostic quality control feature. A second test is an active quality control procedure, which is performed with sensors on a patient. The two tests can be used alone, each being sufficient to confirm that the sensor is working properly, or can be used together, to both ensure proper function and also proper placement of the sensors on a patient. When performed together, the tests are performed sequentially, first the self-diagnostic test and then the active diagnostic test on the patient.

Figure 26:
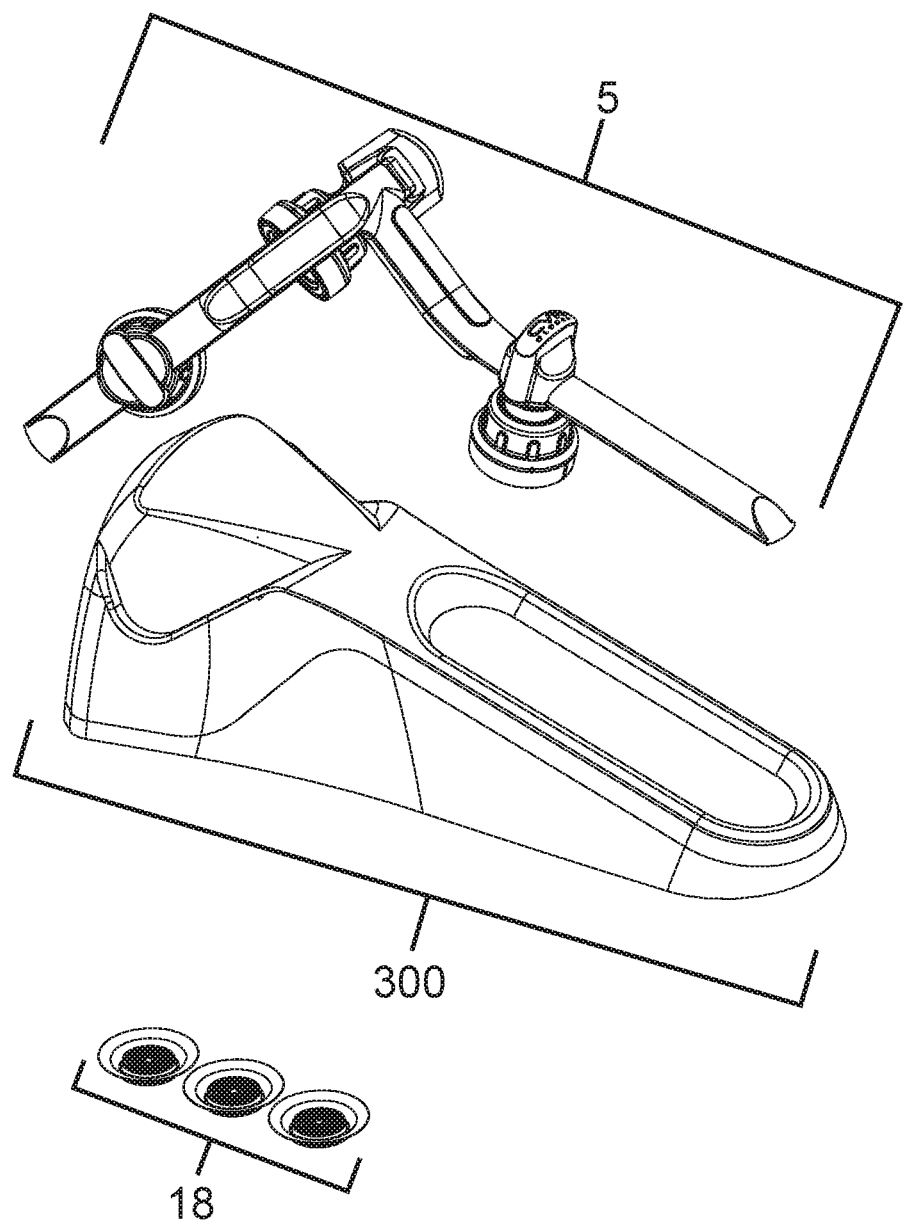
FIG. 26 array on a base

Accordingly, in preferred embodiments, methods exist for determining the proper function of the sensitive piezoelectric components. FIG. 26 depicts a first embodiment comprising an array 5 positioned over a base 300. The array 5, is but one example of a configuration of, as pictured here, three listening pods. Embodiments of sensory pods, as depicted in greater detail in FIGS. 16 and 7 depict a sensor pod attached to an array. FIG. 7, in particular, depicts a piezo sensor 90, which is the primary component that is being tested for quality control in these features.

FIG. 25 details a base 300 that provides for storage, charging, and calibration for the array 5. The base 300 comprises a base enclosure top 310, a base enclosure bottom 96, and a bottom closure plate 98. A decorative elastomeric TPE over-mold 305 can be provided to protect the base 300 and the array 5. The transmit wireless charging coils 93, 94 are arranged to power the optional respective wireless charging coils of the sensor pods 1. Also arranged in the base 300 is a calibration speaker 97. The electronic module 95 powers optional transmit wireless charging coils 93, 94, when utilized with an array having a corresponding charging feature. In other embodiments, a base can directly charge several batteries or a single battery with a mechanical connection, as depicted in FIG. 7, 131, as is known to a person of ordinary skill in the art. In several embodiments, the electronics module generates a calibration and verification signal to be reproduced by the calibration speaker 97. The base enclosure bottom 96 has one or more sound holes 99 arranged therein. The sound may resonate thru 305, eliminating a hole thru the enclosure, preventing the intrusion of cleaning liquids, dust, dirt, hair, etc. into the enclosure. The base can be secured together with fasteners, as depicted, with adhesives, plastic welding, or other similar fastening mechanisms.

In one embodiment, disposed of within the base 300, and specifically adjacent to the cradle for each of the sensor pods 1, is a respective speaker 97. A computer is coupled to the base 300 for communication via a USB connection, Bluetooth, near field communication, RS-232, or the like. The computer couples to the speaker 97, and when the SDD (Stenosis Detection Device) is activated, a program is executed by the computer system so that it performs a diagnostic and quality control test on each of the sensor pods 1.

The diagnostic and quality control procedure comprises a program that plays a known set of sounds generally corresponding to sounds that will be detected and recorded when measuring sounds on the body of a patient. These sounds include low and high frequency sounds, typically low amplitude. Once the sounds are played, the sensor pods 1 detect the sounds and convert the sound to a digital signal that is plotted and compared to a predetermined plot of the sounds that were played. Alternatively, an analog signal is generated and compared with the predetermined plot. Each of the sensor pods 1 is independently tested to determine if it meets an acceptable standard. In one embodiment, and error message is generated if the sensor pod output is not within 10 percent of the predetermined plot at a given data point. Other standards can be used to determine an error condition exists. A range of 1 to 50 percent at each data point can be used to determine if the sensor pod 1 is not functioning properly. Alternatively, the overall plot can be analyzed, instead of a point-by-point analysis, to determine if a sensor pod 1 is functioning properly. Typically, a sensor should be within 25% of a predetermined frequency.

If any sensor pod is not detecting an appropriate sound, then the system will notify the user of an error. In most instances, the error means that a particular sensor pod has exceeded its useful lifetime and is due for replacement. These devices theoretically have a lifespan of several hundred uses under ideal conditions. However, in a medical office, the continuous placing of the array 5 on to a patient, and detecting and recording real sounds, may result in distortion after even a few uses. Accordingly, the system is able to determine whether the detected sounds are simply drift that is a slight change in the detected sounds, or whether there is an error or fault in one of the sensors. If there is only a slight drift, the system can calibrate each unit so that the measured noises from the system are consistent through use.

If the measured sounds are greater than a tolerance of more than 10%, or more than 25% as defined for the occasion, the system notifies the user through images on a display, lights on the sensor pod, audible messages, or other manner to communicate the error, and identifies which sensor pod is faulty. A user can then quickly replace the faulty sensor pod or the disposable piezo assembly 85, and re-run the quality and calibration control program.

After the sensor pod is replaced and the quality control program is re-run, and the replacement sensor pod is confirmed to be working properly, the system will alert that it is ready for placing on a patient. Each of the sensor pods can be appropriately placed onto the patient.

FIG. 16 details an embodiment of a listening device, comprising a yoke 5 having three sensing pods 1. The yoke 5 secures the three sensing pods 1, and by holding the yoke 5 at the neck 3, the sensing pods 1 can be placed against a patient's body, thereby positioning the sensor pods adjacent to the carotid arteries and the sternum. A concern arises, however, where the sensors are not in the correct location on the body, wherein a weak or improper signal is detected by the sensor pods, or when one of the sensing pods is damaged or broken in the process of moving the yoke from the base 300 to the body. This poses a challenge for the operator, as a broken sensing element would provide no signal, and wherein weak signal would not give reliable results. Furthermore, there is obvious concern for a patient, as improper or unreliable results can have significant deleterious effects. As described herein, the device, a system, and methods of use of the device and system, provide for mechanisms to assist with positioning of the device on the body.

Figure 28:
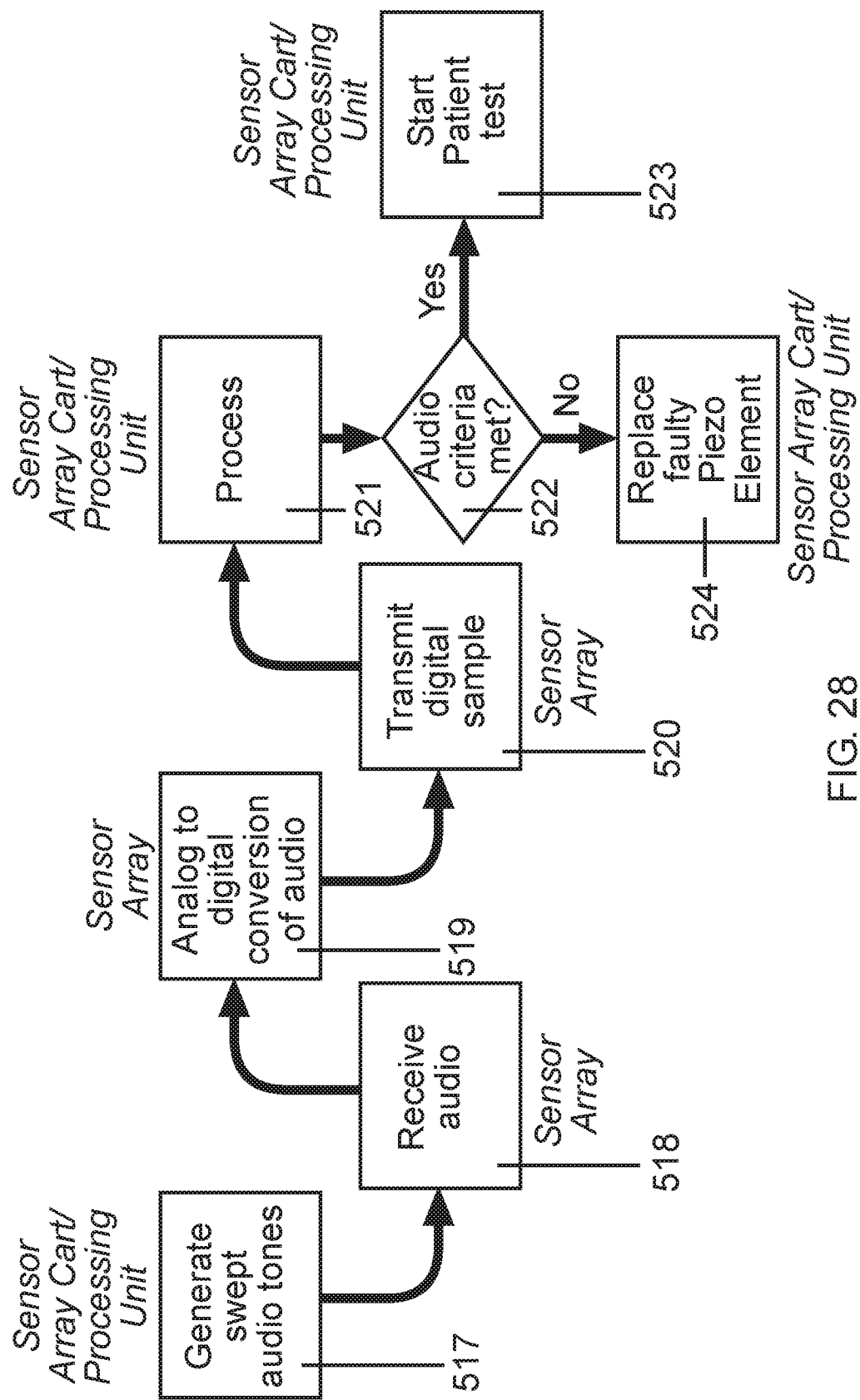
FIG. 28 details a flow-chart of a quality control process.

The diagnostic and quality control procedure is depicted in a flow-chart of FIG. 28. The process includes several steps as defined generally in the flow-chart of steps 517-523. A first step 517 comprises a program that plays a known set of sounds corresponding to sounds that will be detected and recorded when measuring sounds on the body of a patient. The piezos 90 detect the audio 518, which is then converted from analog to digital 519. The digital sample is transmitted 520 to a processing unit for processing 521. A criteria challenge 522 is defined, with the criteria met 523, thus starting a patient test, or not met 524, which requires the replacement of a faulty piezo 90, through replacement of one or more components as defined herein, and restarting the test again at 517 once the piezo is replaced.

When performing the test in step 517, the sounds include low and high frequency sounds, typically at low amplitude corresponding to the range of sounds to be detected by the SDD device. Once the sounds are played, the sensor pods detect the sounds and convert the sound to digital 519. The criteria step 522 compares the digital sounds received to the actual sounds played. For example, a comparison can be made between amplitude and frequency, and overlaid to compare the two samples. Each of the sensor pods is independently determined to meet an acceptable standard, or tolerance for example within 50%, 25%, 10%, 5%, or within about 1% of the sounds based on the determined Hz and, optionally, the amplitude of the detected sounds. Simply comparison software can make these comparisons between the two sounds.

If any sensor pod is not detecting an appropriate sound, then the system will notify the user of an error. In most instances, the error means that the particular sensor pod is due for replacement. While these devices may theoretically have a lifespan of several hundred uses under perfect conditions, the reality of a medical office and placing a device on or adjacent to a patient and detecting and recording real sounds may cause distortion after even a few uses. Accordingly, the system is able to detect and determine whether the sounds detected are simply drift that is a slight change in the detected sounds, or whether there is an error or fault in one of the sensors, thus requiring replacement. If there is only a slight drift, the system can calibrate each unit so that the measured noises from the system are consistent through use. An appropriate program on the system can make these changes to the data based on the actual versus detected sounds, through a simple calibration program. Accordingly, the played tones provide for the ability to both detect and calibrate the device before every use.

If the measured sounds differ by more than the acceptable tolerance, the system engages the user through images on the display, lights on the sensor pod, audible messages, or other means for communicating error, and wherein the particular sensor pod that is faulty is identified. A user can then quickly replace the faulty sensor pod or disposable piezo assembly 85, and re-run the quality control program. An exploded view of a sensor pod is depicted in FIG. 5, wherein a portion of the components depicted therein can be appropriately placed in a single replaceable and disposable component for ease of use. This disposable piezo assembly 85 can be secured to the rest of the sensor pod via ordinary connection means such as a swivel mount, bayonet, threaded fastener, snaps, quarter-turn, magnetic, hook and loop, or other known attachment means.

For example, FIG. 7 as described above, depicts an outer array half 140, which connects to an inner array half 130. A PCB charger contact 131 provides for an electrical contact between a contact in the base 300 and the array. The wiring harness 132 connects to the PCB processor board in each of the attached sensor pods. So, for example, here there are depicted three sensor pods. However, in embodiments having one, two, or more than three sensor pods, fewer or additional connections would be needed. Furthermore, certain embodiments may utilize a sensor pod having multiple piezo elements. Accordingly, a wire from harness 132 will be necessary for each piezo.

FIG. 7 further depicts an exploded view of a sensor pod, with the entirety of 90 through 125 being a complete sensor pod. By contrast feature 85 depicts a disposable piezo assembly. The disposable piezo assembly 85 comprises a piezo 90, a piezo wiring 91, which connects the piezo 90 to the PCB contact board 105. A piezo cap 100 is surrounded on each side by a pressure sensitive adhesive 92, this pressure sensitive adhesive 92 secures the piezo 90 to the piezo cap 100 and to the PCB contact board 105, on the other side with the second pressure sensitive adhesive 92. These components, can be normally configured in a disposable arrangement, wherein the quarter turn locking feature 101 can be used to screw on and off the disposable 85 by connection to the quarter turn locking pin 116. The quarter turn feature can be exchanged for other locking or attaching features, such as magnetic attachment, compressions/friction, one or more threaded fasteners, and the like. Known attachment means are known to a person of ordinary skill in the art.

When the disposable piezo assembly 85 is attached, it contacts the PCB Processor board 110, which assembles into a pocket in 115, and is captured by 85. In this manner, when a quality control test is performed, and a sensor is identified as faulty, the attachment means can be withdrawn and the disposable piezo assembly 85 can be removed and a new disposable piezo assembly 85 attached and the test re-run.

In certain embodiments, it is advantageous to have the entire sensor pod replaced, not just the top disposable component. For example, the PCB board 110 may in some instances wear or be damaged. Alternatively, the diaphragm bellows membrane 120 may need replacement, or simply replacement is warranted because of contamination concerns. Accordingly, the entire piezo assembly can be replaced, by removing threaded fasteners 133 or by removing locking cap 125.

The diaphragm bellows membrane 120 locks with certain features, to ensure that it can freely flex and compress to allow for the fit of the piezo against the body. The diaphragm bellows membrane 120 fits feature 121 into a locking groove 117, which traps locking feature 121 between locking cap 125 and the PCB housing 115. Locking feature 122 secures the diaphragm bellows membrane 120 between the inner array halve 130 and the outer array halve 140. This creates a flexible "drum head".

For each use of the piezo, a sensor pad 18 is also utilized for sanitary conditions and to ensure a quality sound contact to the piezo 90. The sensor pod 1 of FIG. 3 can be replaced by sliding off the track or removing the track base 11, and replacement by sliding on a new pod, or attaching the new pod over the track.

After either replacement of the disposable component 85 or replacement of the entire sensor pod, the quality control program is re-run and the replacement sensor pod is confirmed to be working properly, the system will alert that it is ready for placing on a patient. Each of the sensor pods can be appropriately placed onto the patient, as depicted in FIG. 10.

As depicted in FIG. 11, when the carotid artery is tested, at least one sensor pod is placed adjacent to either the left or right carotid artery. Optionally, a sensor can be placed adjacent to the heart. The sensor pads 18 are placed on the skin of the patient at the carotids. In certain embodiments, the heart sensor, if utilized, can be placed over the clothes of a patient, as it is detecting heart rate, which is sufficiently loud to not need to be directly on the skin. However, for more precise applications, a skin to skin application is needed. Indeed, in certain embodiments, a sensor array comprises only one or only two sensor pods, and no pod is placed adjacent to the heart.

As with the quality control procedure on the base unit, once the sensor pods are placed on the patient, the operator can engage the device to begin detection and recording on the patient. Because the sounds that are being detected and recorded are known within a certain range of sounds, that is, the sounds are generally known to a certain frequency and amplitude, and a further quality control test is performed for a duration of between 1 and 30 seconds. This test provides a quality control diagnostic to ensure that the sensor pods are detecting proper sounds from the patient, and thus confirms two pieces of information: first the proper placement of the sensor pods on the patient; and second that the sensor has not failed in the time between initial quality control tests and placement on the patient.

Since there are at least two and likely three sensor pods, each pod communicates with the computer identifying the detected sounds, which can be recorded by the system and compared in real time to a predicted sound. Accordingly, the sensor pod at the heart will predict a certain sound and the sensor pod(s) at the carotid arteries another sound. If one or more sensors does not detect the predicted sounds, a signal will engage to identify the sensor that is not properly detecting the predicted sound. This signal will alert the operator that the sensor pod needs to be adjusted to a different position to properly detect the sounds for the particular test.

Figure 31:
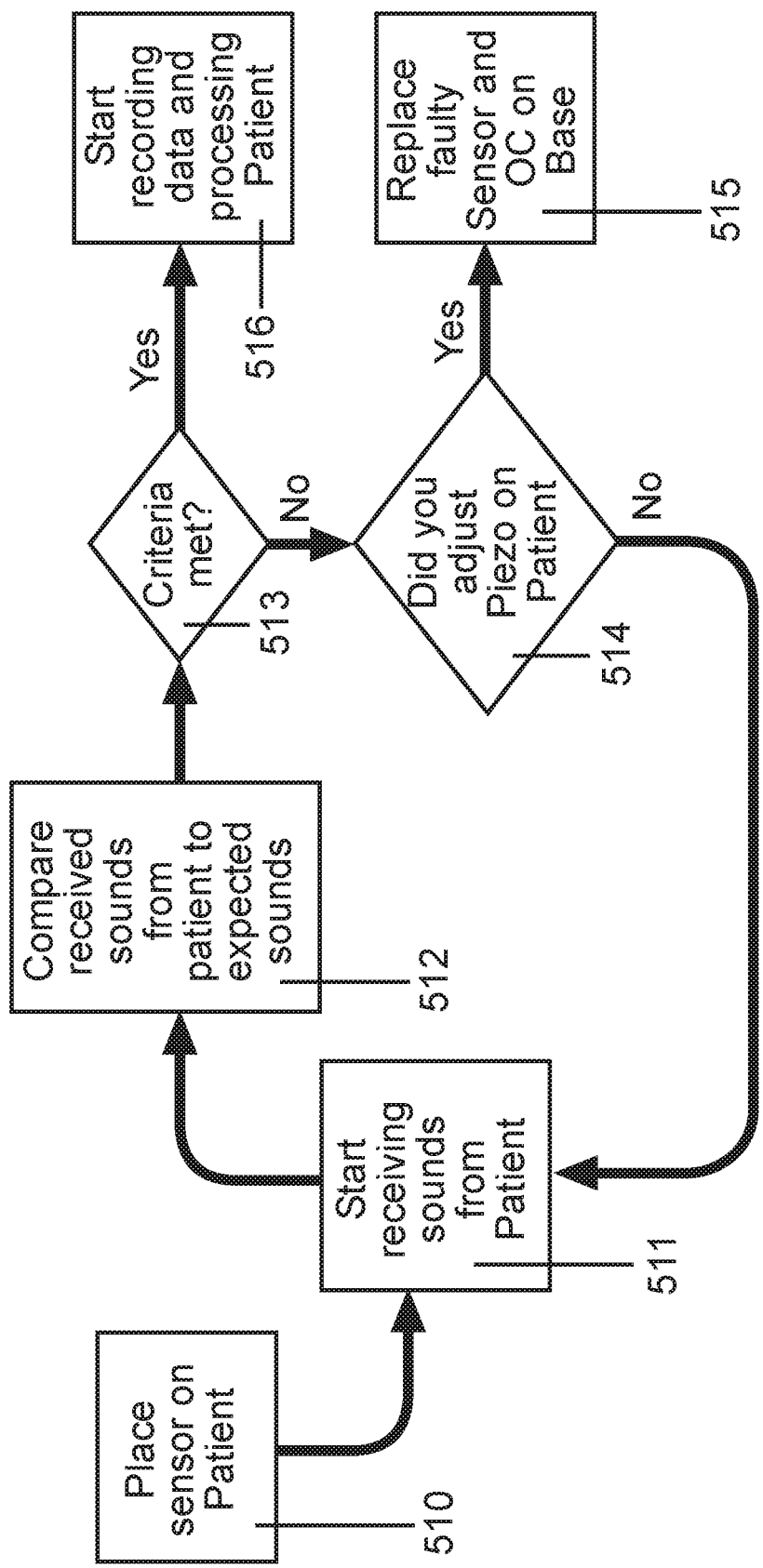
FIG. 31 details a flow-chart of an active quality control procedure.

FIG. 31 provides a representative flow chart of an embodiment of this active quality control process. First, the sensor is placed on the patient 510. The piezos then start receiving sounds from the patient 511. The received sounds are then compared to expected sounds from the patient 512. The comparison identifies an expected frequency at each piezo. For example, we expect to hear the heart beat at about 1 Hz. Accordingly, if this sound is received by the piezos, within 25%, 10%, 5%, or 1% of the expected frequency, then we know that the devices are properly positioned over the carotid arteries. Alternatively, we can look for a frequency between 60 and 260 Hz, which corresponds to the large ring vortices at the carotid artery. This corresponds to the expected stenosis at the carotid artery. Intensity is patient relative. Accordingly, when intensity is utilized as a parameter, an expected value may be assumed, but the system can simply identify relative intensity that is by re-positioning a sensor, the intensity may be increased or decreased from the prior position, with an increase in intensity being an improved position. Accordingly, an indicator on a display, volume of sound being played through the speaker, rate of flashing of a light on the sensor, sensor array, or the base, or a set of indicator lights, with more lights showing greater intensity and fewer lights showing lower intensity. Those of skill in the art will recognize there are numerous ways to indicate a change of intensity.

If the criteria is met, 513, then we proceed to start recording the data and processing the patient 516. However, if the criteria is not met, we need to first adjust the piezo on the patient 514. Adjustments can be just a few centimeters, or more as necessary, in order to get the piezo closer to the artery of interest. After adjustment the device again receives sounds from the patient 511 and compares the sounds to the expected sounds 512 to determine if the criteria is met.

In certain instances, after movement and adjustment of the device, the piezo is still not finding the proper sounds. This can be due to continued improper placement or failure. Accordingly, it is best to replace the piezo 515 and start another quality control procedure as outlined above on the base.

The embodiments of the system utilize variations of quality control programs for initial setup testing of the sensor pods and then for quality control testing of the proper position on the patient. A variety of alarms, indicators, or signals can be utilized in each of the quality control programs to ensure that the issue is detected and corrected.

Figure 29:
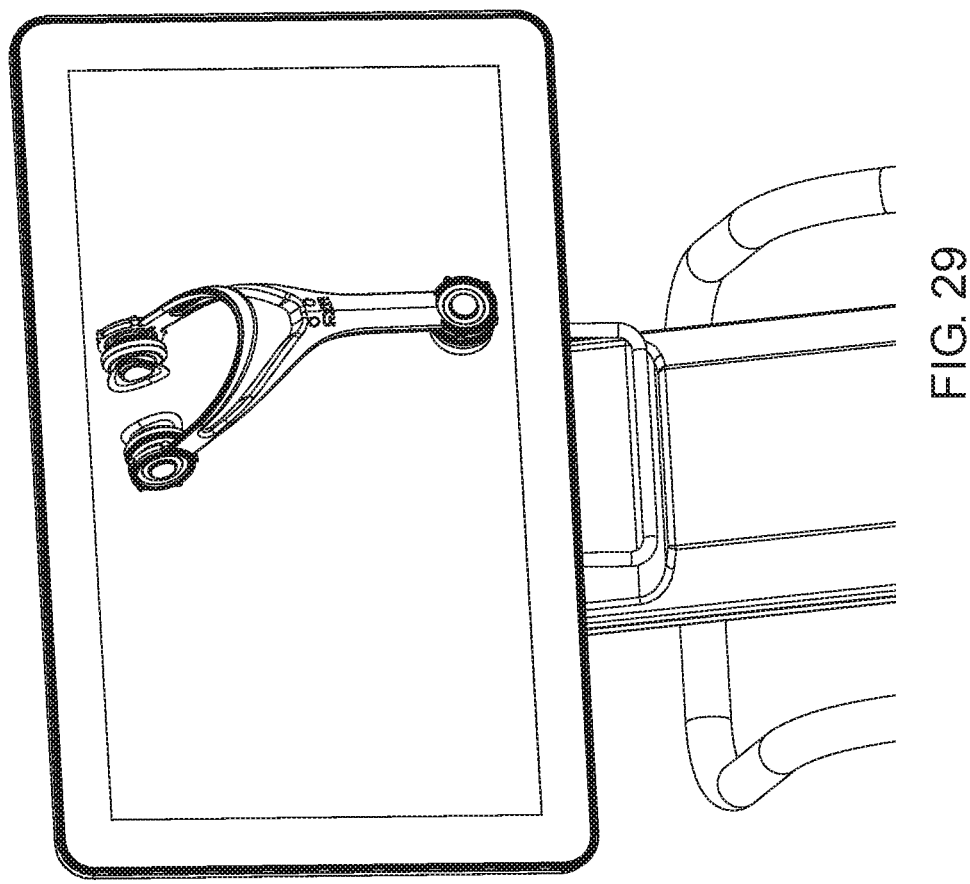
FIG. 29 details a sample GUI.

For the initial quality control program, when the sensor pods are still in the base unit cradle, it is appropriate to indicate a fault with a computer Graphical User Interface (GUI) as depicted in FIG. 29. An image of the specific array and number of sensor pods is indicated on a screen. The system can recognize the number of sensors based on data received and will indicate proper function or improper function of each. For example, the GUI may indicate with a green color at each sensor that it is functioning properly, or a red light when improperly functioning and requiring replacement. Alternatively, an arrow or words may indicate replacement or proper function for each sensor. Instructions to replace a sensor will be indicated on the screen with a step-by-step directions, based on the particular type of connection mechanism. After replacement, the quality control program can be re-run to confirm proper function.

Figure 27:
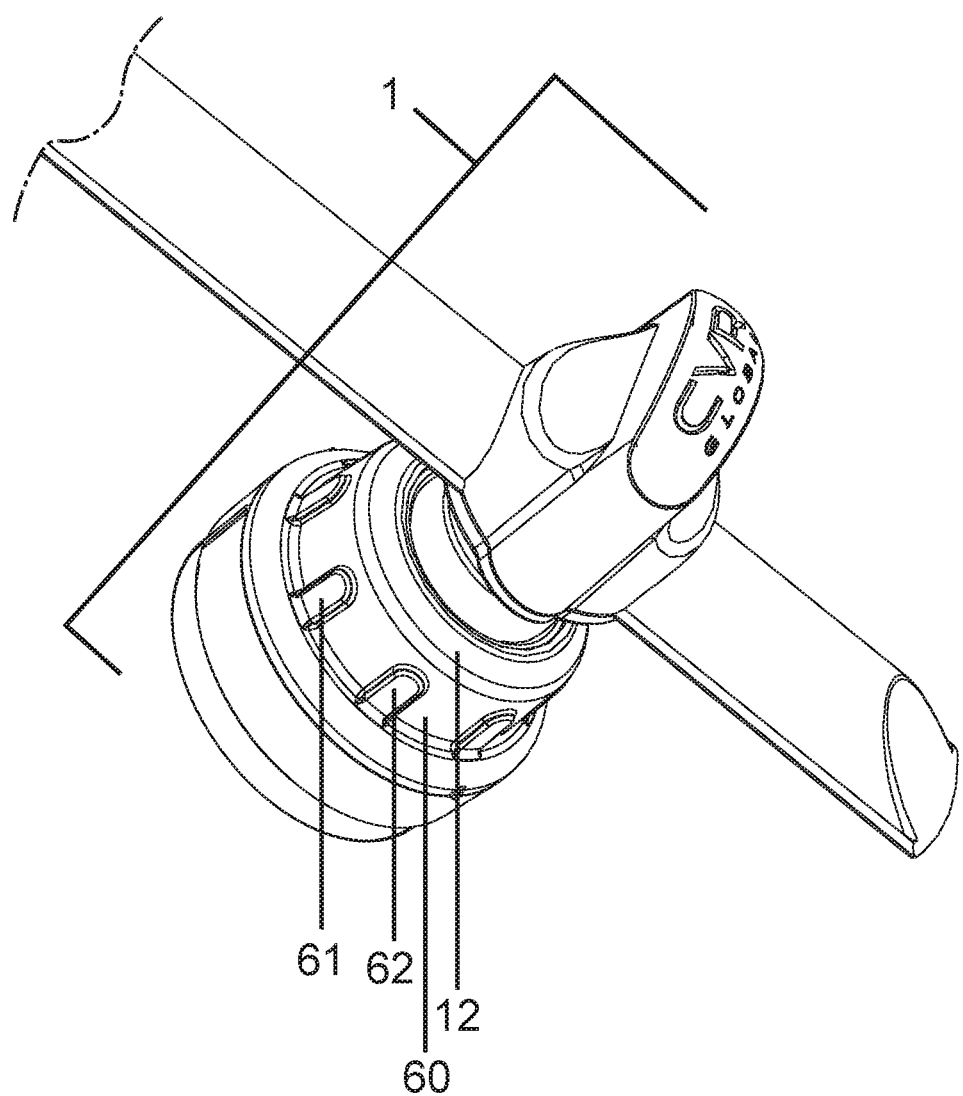
FIG. 27 depicts an example of a sensor pod having attached indicators.

In other embodiments, a colored light system, such as a green or red light based on green being good, and red signaling an error with the sensor pod can be directly placed on the sensor pods (see FIG. 27). Indeed, FIG. 27 depicts an first indicator light 61 and a second indicator light 62 illuminating through a clear, TPE, overmold material 60. These can be illuminated based on the pass or fail of a particular process. A third or additional lights are depicted, but not labelled, and can be further utilized as described herein.

Figure 30:
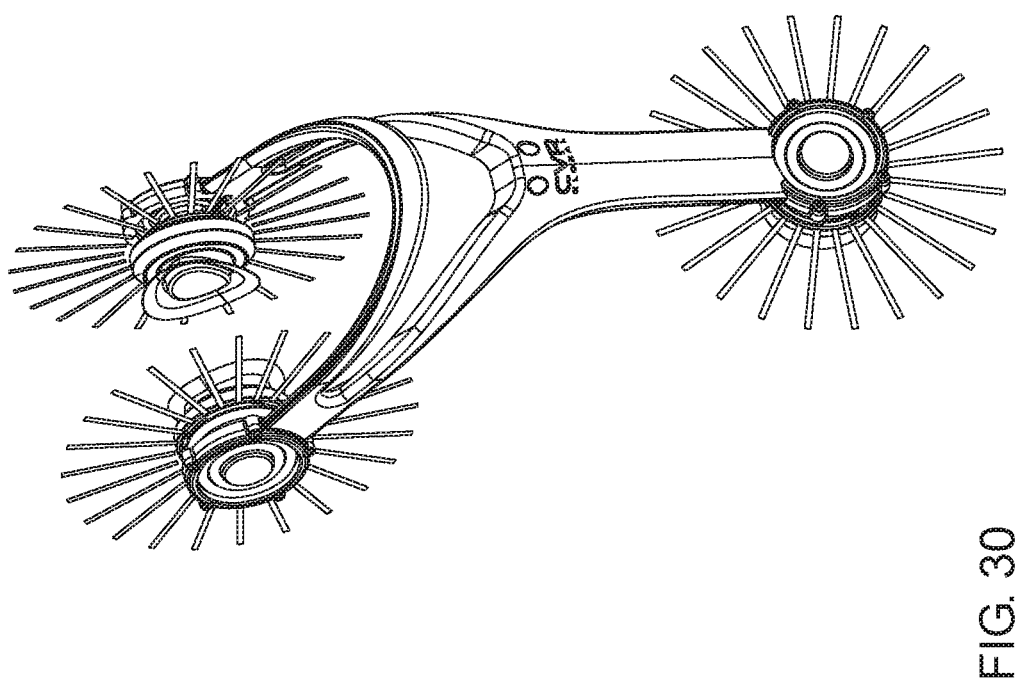
FIG. 30 details an example of light indicators indicating after a test.

FIG. 30 depicts a plurality of lights will indicate based on the self-diagnostic phase of the test. Color changing LED lights, or simply alternating LED lights, or an equivalent, can be used to provide easy indication with different colored lights, shown through clear or translucent plastic housing. These lights can be placed on the base unit itself. In other embodiments, or in addition to these lighting systems, an audible alarm may signal from the SDD device to warn of an error. Furthermore, the display unit may further provide for a display indicating which of the sensor pods needs to be replaced.

The lights of FIG. 27 and FIG. 30 can also be used during the active diagnostic phase. For example a set of three lights can be used, green indicating proper sounds received and proper placement and red for improper placement or failure, i.e. not meeting one or both criteria. However, a yellow light may be further included for several reasons. First, the yellow light may hold steady or flash to indicate that the self-diagnostic or active diagnostic phase is being performed. The yellow light may stay illuminated, or joined with a green or with a red, if, for example one of the criteria are not met. This would indicate that the sensor is functioning but that it is improperly placed. For example, the intensity is not sufficient, or the frequency improper, would suggest that the device is not in the proper locating for high quality data. The device can be adjusted on the patient and the active diagnostic phase continues until either a green light is indicated for all sensors or a single red light is indicated on one sensor.

In certain embodiments, a button on the device or on the base is pressed to perform the active diagnostic phase. However, in preferred embodiments, once the self-diagnostic test is complete, the active diagnostic phase immediately starts. The active diagnostic phase will continue, until either all sensors indicate green or one indicates red. Typically, this will last up to 30 seconds, at which time a red light will indicate to re-start the test, or to replace a sensor.

If one sensor remains yellow or yellow with green/red, during the active diagnostic step, the lights, visual, and or audible alarms can further assist in positioning the device properly on a patient. For example, the light remaining yellow will turn to yellow and green, if the signal is better, or from yellow to yellow and red, if the signal is worse. Accordingly, the sensor can be moved in a proper direction towards the yellow/green until just a green light is indicated. Furthermore the GUI can be utilized in the same manner, with an indicator on the screen suggesting the direction to move the sensor. Ultimately, if a sensor pod does not detect the proper sounds from the patient, then one or more alarms will register and the operator will know that one or more sensor pods need to be replaced on the patient. In certain embodiments, the visual screen, a visual identifier will flash to aid the operator in placing the sensor pod in the proper location.

In further embodiments, where a sensor pod is identifying an improper sound or not detecting a sound, a visual alarm may be generated, such as a red light, which indicates improper position or a sensor failure. The SDD can detect and compare the sounds in real-time, so the operator can then slowly move the sensor pod to a different location and wait a few seconds to see if the light turns from red to green, indicating a proper position. The operator can continue to move the sensor pod on the patient until it is indicated on either the sensor pod, on the array, or on the SDD device display that the position is correct.

If the operator is unable to determine a proper location on the patient after 30 seconds, the SDD will alarm with a visual or audio signal to perform a base unit quality control procedure again to ensure that the sensor pods are all functioning correctly, or to simply replace the sensor that indicated failure. After replacement or if the sensor pods are determined to be functioning correctly, the operator can again restart the process of placing the sensor pods on the patient.

Accordingly, a preferred embodiment for determining proper placement of sensor pods on a patient comprises a stenosis detection system comprising a base unit having a cradle, at least two sensor pods, a display and at least one alarm mechanism; wherein while the sensor pods are engaged in the base unit cradle a self-diagnostic quality control procedure is performed to confirm that the sensor pods are properly functioning. After confirmation of the proper function of each of the sensor pods, the devices can be placed onto a patient wherein an active quality control procedure is performed. The active quality control program is run for between 1 and 30 seconds wherein each sensor pod is communicating with the compute of the detection system in real-time to ensure that each of the sensor pods is measuring the appropriate sounds. Wherein the system provides for an audio or visual notification that the active quality control program is met, or wherein the system identifies one or more sensor pods that are improperly placed. Wherein the system then provides an alarm to any sensor pod that is not properly placed. Wherein a visual or audio mechanism is provided to provide real-time feedback as to the proper position for each sensor pod, and wherein one example provides for a red light for improper position and green light for a proper position. Certain embodiments utilize a yellow light to indicate that one or more of the self-diagnostic test or active diagnostic test are proceeding.

Other audio or visual alarms or mechanism may be further included in the system so as to aid in the placement of the sensor pods on a patient.

In preferred embodiments, the active quality control step on the patient provides for immediate real-time feedback to the correct placement of each sensor pod to ensure fast and reliable positioning of the sensor pods, and also to confirm fast, precise, and accurate detection and determination of stenosis on the patient.

The method comprises: Performing a first base unit quality control test; confirming that each of the sensor pods is properly functioning; placing sensor pods on a patient; performing a second quality control test, wherein the sensor pods detect sound in real-time and compare said sound to a predicted sound; and indicating with an alarm whether the sensor pod is properly placed on the patient by comparing the detected sound in real-time to a predicted sound based on historical data.

In a preferred embodiment the system uses a computer to run software to implement the features as described in the embodiments herein. Accordingly, the computer is connected to the array and/or to the sensor pods via a connection means either wired or wireless, as is known to one of ordinary skill in the art. The software comprises the various quality control procedures, as well as appropriate code to provide alarms and to notify of the need for replacement or modification. Further features include the ability to calibrate the system in view of a quality control test.

Therefore, preferred embodiments of the disclosure comprise a method of confirming the proper position of a medical device upon a patient comprising: performing a first quality control procedure to ensure functioning of the sensor pods, comprising playing a predetermined set of sounds and comparing the predetermined sounds to the detected sounds; performing a second quality control procedure while detecting sounds from a patient wherein the test compares the detected sounds to sounds that are ordinarily present in detection of the particular artery or vessel of interest; and triggering an alarm wherein the detected sound does not meet the predicted sound, or triggering an approval if the detected sound confirms with the predicted sound.

Noise Attenuating Strategies

A major hurdle in creating a device that conforms to the necessary levels of accuracy is to ensure that the data received for each test is of the highest quality. By performing the prior quality control procedures, the devices are known to be functioning properly. However, it is necessary to now utilize passive and active noise attenuating strategies, as well as computer implemented de-noising strategies to generate clean and clear data. Accordingly, we need to eliminate noise from the data sample in any number of ways, so that the resulting data is clean and clear for quantification of stenosis.

The noises that we are particularly measuring are subtle large ring vortexes. These vortexes are created as wall pressure fluctuations distal to a constriction (stenosis) in rigid or elastic pipes, or in arteries, reveal the presence of low-frequency maxima. These fluctuations are found to be associated with large-scale, medium-scale, or small-scale vortices (also called "eddies" if small), that are strong in the region distal to the constriction (called "stenosis" when in an artery).

Normal blood flow in a heathy patient causes certain sounds which are detectable by our device. Patients which have stenosis in the carotid arteries will often have another 2 or 3 additional sounds that can be picked up by our device. Depending on the amount of stenosis and how many stenosed areas the sound will change. The carotid artery has a branch which feeds two main areas in the head. One main branch going to the brain and the other branch going to the face. The area that we test for is where the carotid artery branches into these two areas. Thus depending if there is stenosis in one branch or two can lead to multiple sounds being picked up. Because these sounds/vibrations are at such a low level it is vital to make sure as much external noise is eliminated as possible. Even small noises in the 20-3000 Hz range can overwhelm the noises we are looking for making noise elimination critical.

With regard to flow and the noises created therein, some of the fluid-flow energy enters into the vortex motions distal to a constriction, which then results in an increase in the wall pressure amplitude, above that of turbulence alone, at the lower frequency end of the wall pressure power spectrum. These maxima are nearly Gaussian-shaped bell curves situated atop a broad, nearly flat spectrum at low frequencies that is due to turbulence within the pipe or artery. The maxima are always found at lower frequencies than the so-called "break" frequency characteristic of the turbulence spectrum where the latter changes quite abruptly from nearly flat to steep declining in intensity (when the logarithm of signal intensity is plotted versus a logarithmic frequency scale).

Interestingly, measuring these maxima and plotting the power spectrum provides for a visual image of stenosis in an artery. Indeed, we have determined that by plotting the power spectrum on the y axis and amplitude on the x-axis, we can effectively determine the percentage of stenosis in the carotid arteries of a patient.

These maxima (generally two in number) are the main features in the frequency power spectrum at low frequencies generated by the wall pressure fluctuations when there is a constriction as compared to the situation of no constriction yet fully developed turbulence. In order to analyze this data, we have developed devices and invented several methodologies and processes that reduce or eliminate extraneous noise from the data samples, to enable further spectrum analysis downfield.

The device eliminates noise in several ways. One by using sound barriers/dampening material to eliminate external noise as much as possible as well as noise caused by the patient moving; i.e. passive noise cancelling. We also eliminate or cancel ambient noise with active noise cancelling strategies, whether generating opposing waves or subtracting ambient noise; finally, we de-noise the received data by methodologies related to data processing using Wavelet, Welch's and Burg's methods. Ultimately, we plot peaks on a PSD and calculate stenosis of an area of interest in the arterial circulatory system through comparing these peaks on the PSD.

Passive Noise Cancelling Strategies and Methodologies

A first set of strategies includes mechanical strategies to eliminate or reduce noise. We can also consider these strategies to be passive noise cancelling strategies.

For example, in preferred embodiments, the yoke 5, as depicted in FIG. 5D is made of a plastic or a polymer. Construction of a yoke with as few components as possible is intended, as additional components create joints that may cause ambient noise to the system. We typically use unibody constructed devices, molded into a form, or devices having an inner and outer portion, thereby allowing some materials to be compressed within said device, and for insertion of wires, batteries, processors, memory, and the like, into the array. In embodiments where multi-body construction is used, it is preferable that mechanisms are in place to ensure proper stability and to prevent unnecessary vibrations and sound due to the construction. This can be achieved through appropriate materials and fixing mechanisms, including the use of dampening materials when connecting two or more components together on the yoke 1. The yoke 5 may further optionally include sound cancelling materials disposed of in or on the yoke 5. This provides that movement of the yoke 5 or of the patient while the yoke 5 is on the patient, will prevent unnecessary noises that may disrupt the sound received by the piezos.

Figure 32:
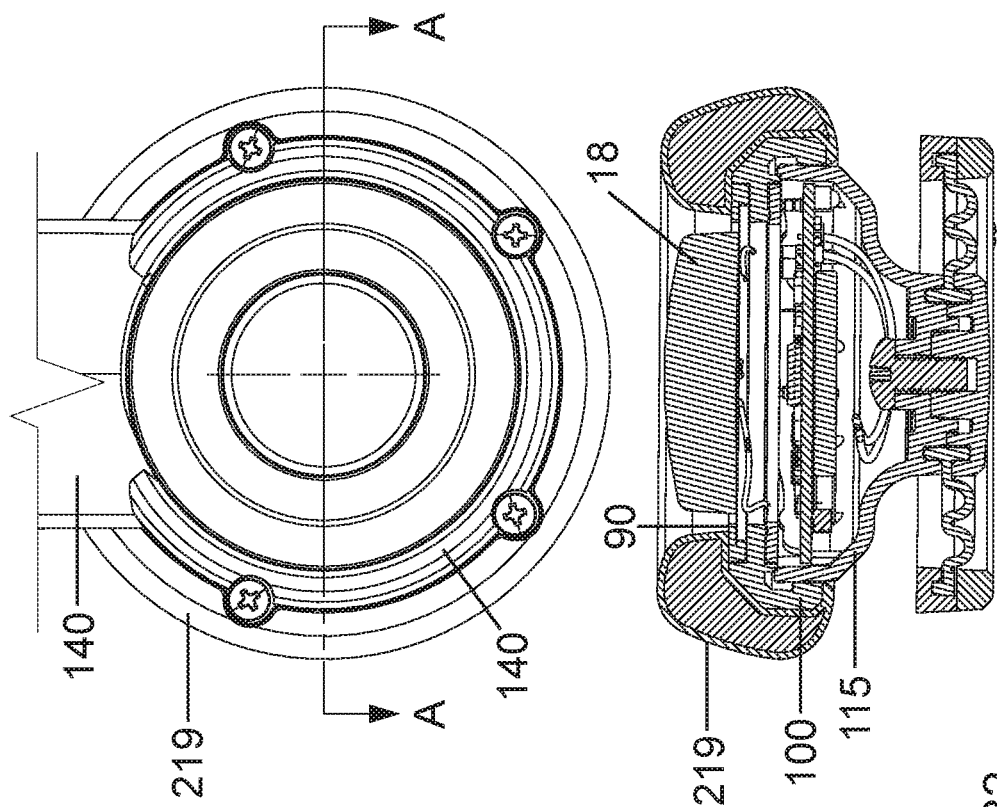
FIG. 32 depicts a passive cancellation device with "over-the-ear" like construction, to block ambient noise from the sensor.
Figure 32:
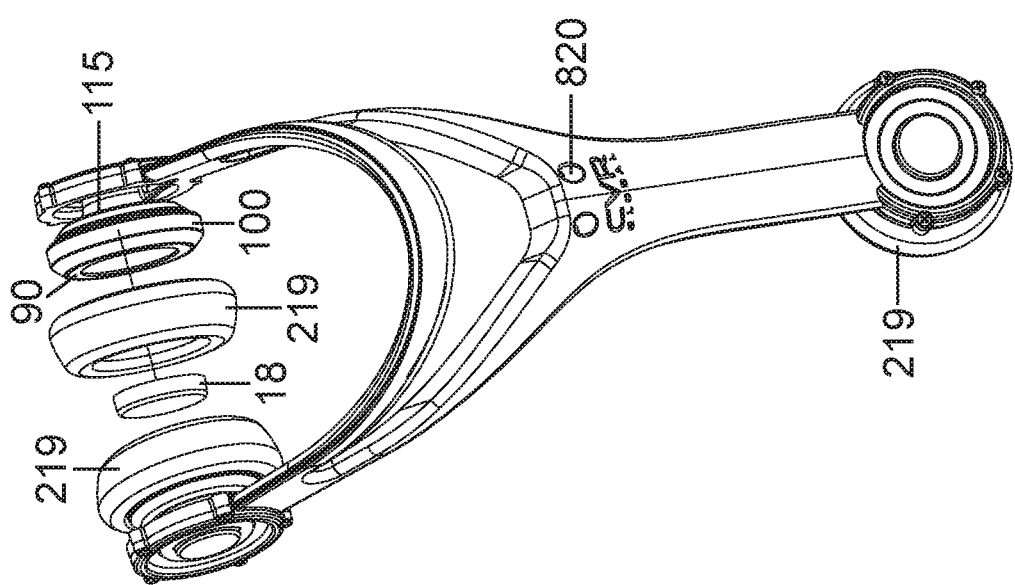

FIGS. 24 and 32 depict disposable sensor pads 18. These pads 18 serve as the first line of active noise canceling, where the pads 18 have a durometer and shape to allow for secure contact with the skin of a patient, which blocks some ambient noise from entry to the piezo sensor 90. The sensor pad 18 is placed on the piezo 90 and positioned such that a flat side of the pad is in contact with the piezo 90 and the obverse side is in contact with the skin of the patient. Particular designs, such as those in FIG. 24 are angled on the skin facing side to create a good seal against the skin. The sensor pads are angled at the skin facing surface, such that on the left hand side, the curvature on the bottom right engages to an angled structure to ensure a good acoustic fit. By contrast, the sensor pad on the right hand side of the page comprises a dual concave structure, to fit around a structure that is rounded. In each case, there is a proper fit, and so the sensor pod must be able to rotate to allow the sensor to be properly fit against the skin to achieve a proper acoustic contact for data collection. Cross-sectional views of the left and right sensor pads are depicted for clarity. The sensor pads 18 further direct sound and vibrations from the patient's skin to the piezo and results in sound and data that eliminates some noise from the signal.

In further embodiments, it is advantageous to utilize gel on the skin of a patient that assists in forming a temporary seal between the pad and the skin of the patient. Certain oil and water based gels or liquids are useful in assisting with the seal.

FIG. 32 adds a further feature, which is an external noise attenuating material 219 that compresses around the sensor pad 18. The external noise attenuating material 219 is like an "over-the-ear" headphone, which blocks ambient noise from the ear. In the similar manner, the external noise attenuating material 219 surrounds the sensor pad 18 and blocks some of the ambient noise.

The sensor pod itself, therefore, must also attenuate and block out some of the ambient noise. This can be achieved through several features that are depicted in detail above in FIG. 8B, however it is again relevant for our purposes here.

FIG. 8B depicts an exploded view of a sensor pod, beginning with the piezo 90 which is attached to the sensor cap 100 with an adhesive 92. The piezo 90 fits within a recess at the top of the sensor or piezo cap 100, and sits on a flange on the opening in piezo cap 100. The piezo cap 100 is made of a plastic material having a density to attenuate and reduce penetration of sound waves. Accordingly, sound will travel from a sensor pad 18 placed onto the top surface of the piezo 90, but will be limited from the bottom surface or from the side of the piezo, due to the construction of the sensor cap 100 and the remaining components. Higher density materials have greater sound attenuating properties, so appropriate density plastics can be selected around the piezo 90 to reduce ambient noises.

A second adhesive 92 connects to the Printed Circuit Board 105, and several PCB contacts 106 contact the spring pins 111 on the PCB processor board 110 to make electronic connections. A processing unit 112 is defined on the bottom of the PCB processor board and comprises a battery, memory, and a processor. Alternatively, a battery may be centrally located, and the processing unit may be centrally located. The Piezo cap 100 contains a groove 101 to receive a quarter-turn locking feature 116 that is located on the PCB housing 115. This housing, like the PCB cap 100 attenuates and reduces ambient noise penetration to the piezo 90. A screw 113 secures the PCB housing 115 to a diaphragm bellows membrane 120, which allows movement of the entire sensor pod in directions in the lateral and longitudinal axis. Accordingly, when a device is placed against a surface, the sensor pod will be able to move away from the surface, or laterally to create a better fit towards the skin of the patient. Furthermore, this diaphragm bellows membrane 120, being non-rigid, will reduce the transfer of vibration and movement from a person holding a device containing the sensor pod, such as an array. A locking mechanism 121 secures the inner portion of the diaphragm bellows membrane 120 between the locking groove 117 and the locking cap 125.

Accordingly, an embodiment of the disclosure comprises passive noise cancellation strategies comprising a sensor pod (features 85 and 86 together) comprising a disposable piezo cap 85, having a piezo 90, a Piezo cap 100 having noise attenuating properties, and a PCB house assembly 86 having a PCB board 110, a diaphragm bellows membrane 120, and a PCB housing 115. A locking feature on the PCB housing 115 connects to the Piezo cap 100 to secure them together. The rear of the PCB house assembly 86 comprises a diaphragm bellows membrane 120 that allows for movement of the components to isolate them from ambient noise and vibrations. The device may further comprise a noise attenuating material 219 disposed of around the sensor pad 18 to passively waves from the piezo sensor 90.

Figure 35:
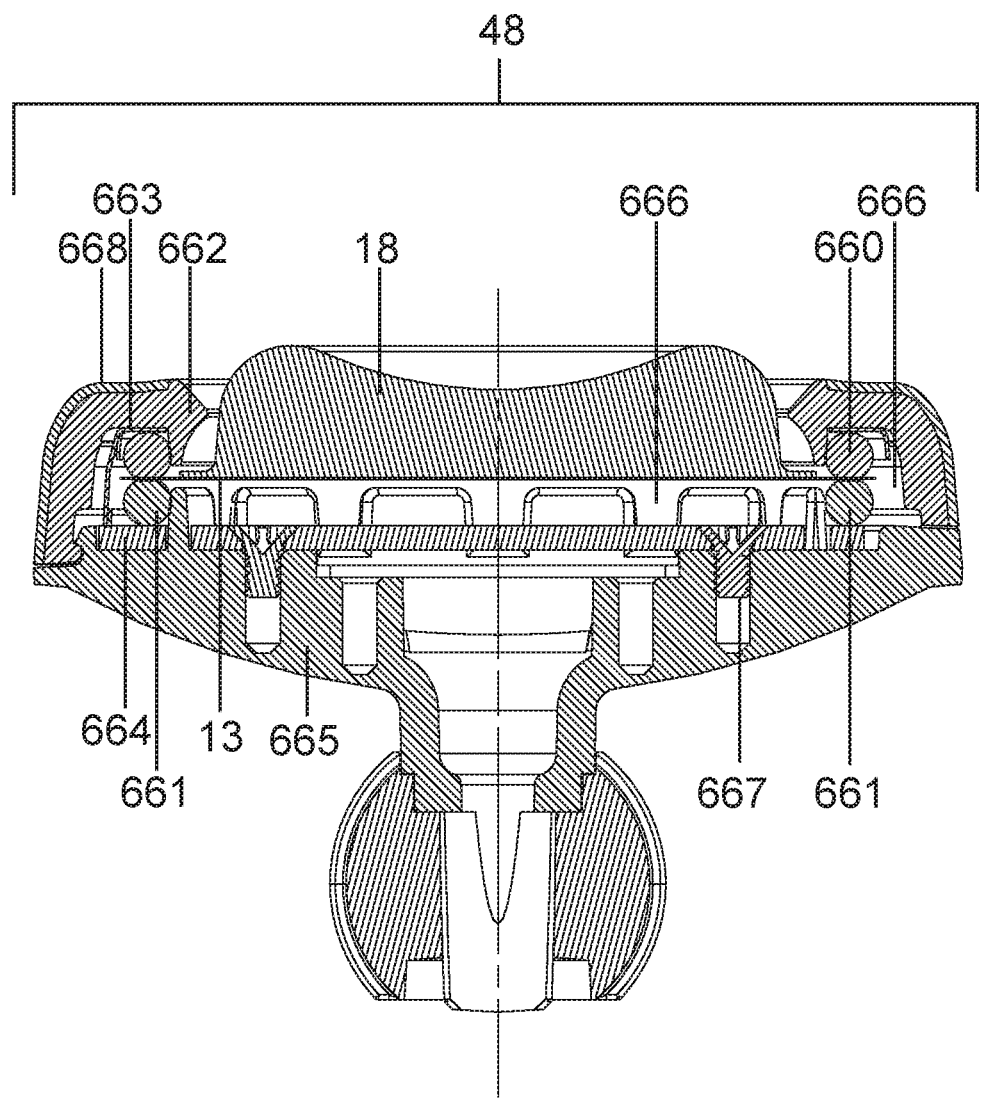
FIG. 35 depicts a sensor pod assembly with sound attenuating materials.

FIG. 35 further details a sample piezo utilizing sound attenuating materials. The sensor pad 18 is positioned on the sensor 13, with attenuating materials 661, 662, 663, 664, 665, 666, 667, and 668 surrounding the sensor 13. By use of these materials, we can surround the sensor 13 with attenuating materials and reduce the ambient noise that is received at the sensor. Appropriate low and high density materials can be use, sound baffling materials and the like.

Active Noise Cancelling Strategies and Methodologies

Figure 33A:
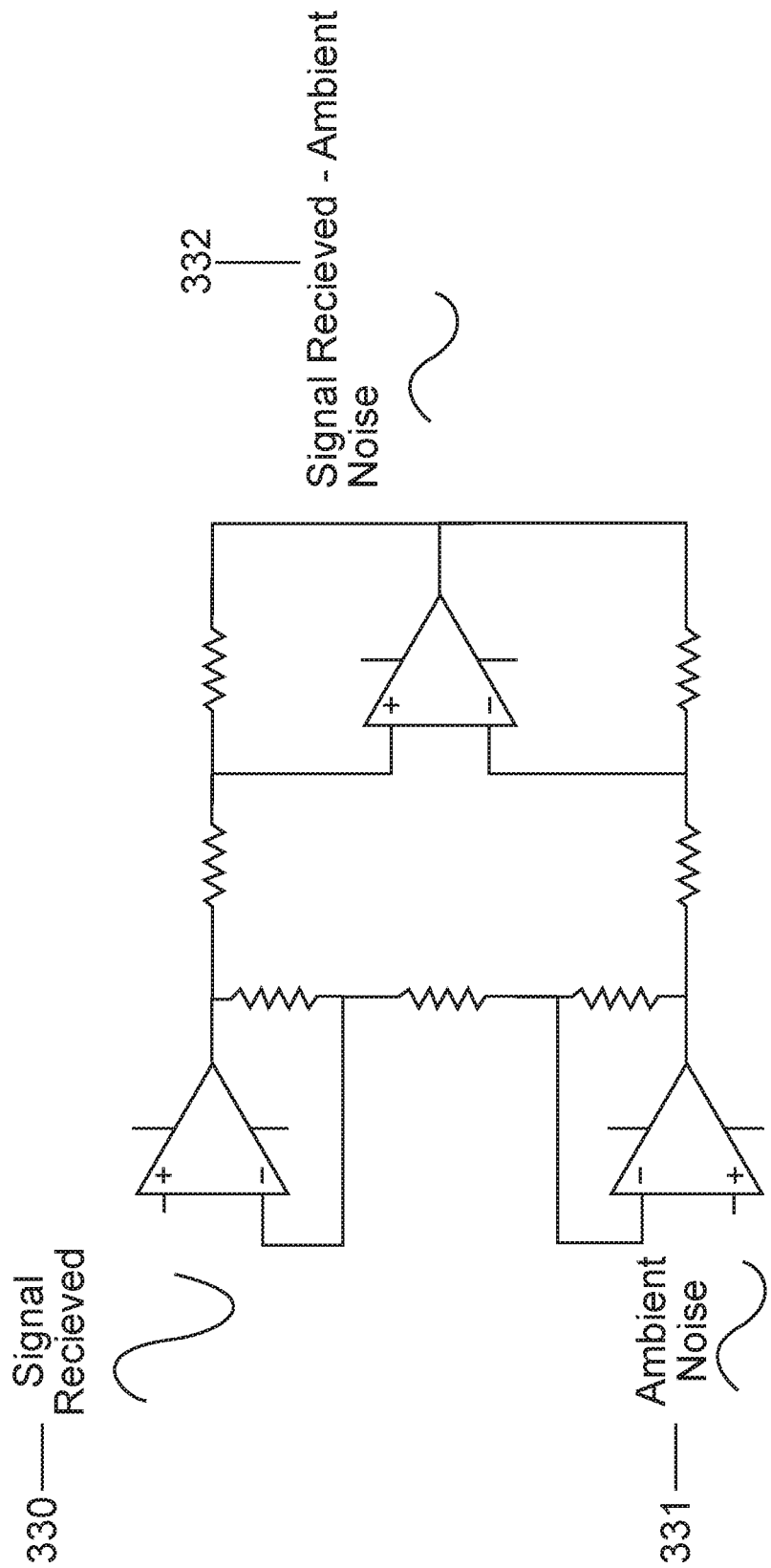
FIG. 33A depicts an electronic view of subtracting ambient noise from a received signal.
Figure 33B:
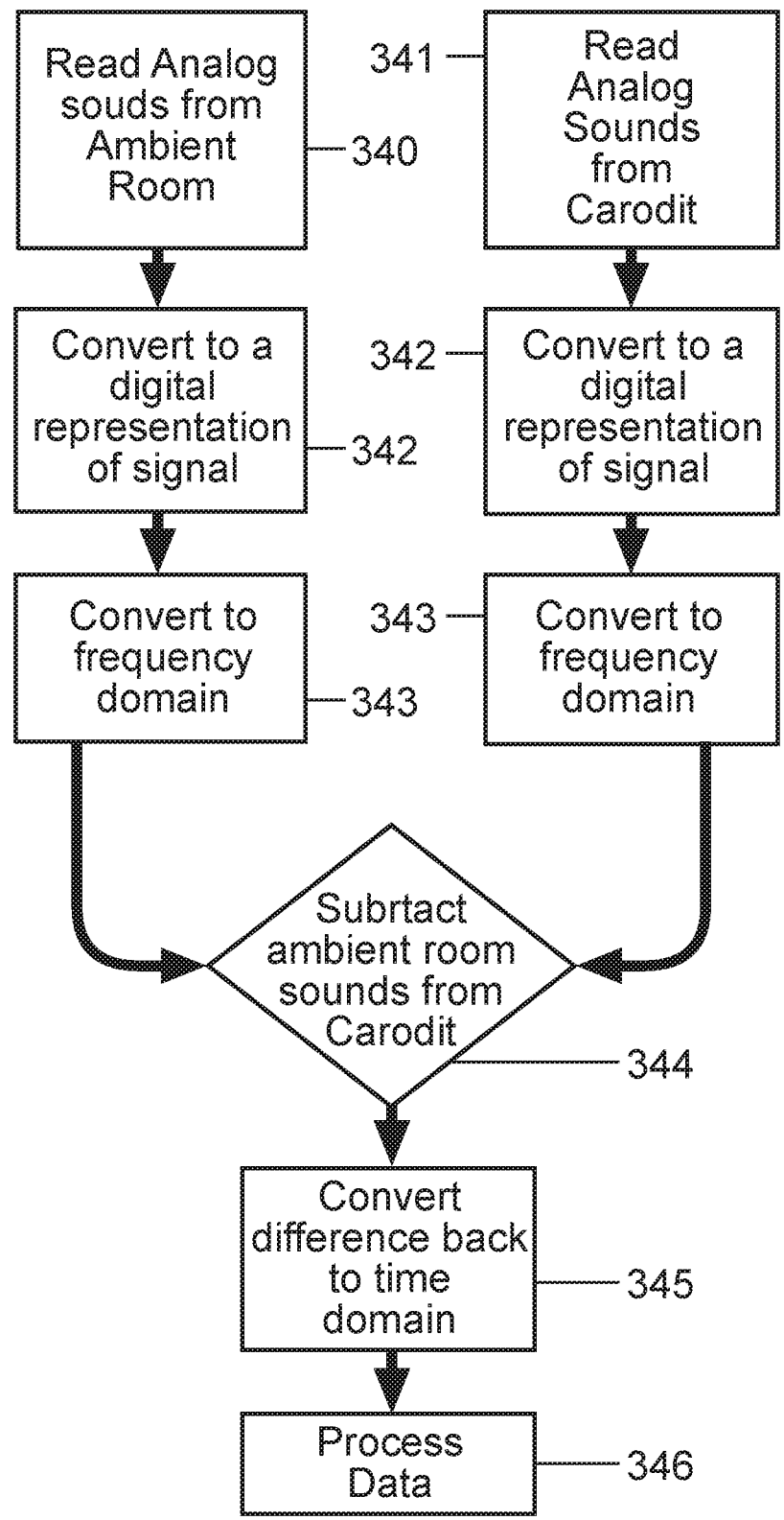
FIG. 33B depicts a flow-chart of subtraction of ambient noise from a signal.
Figure 33C:
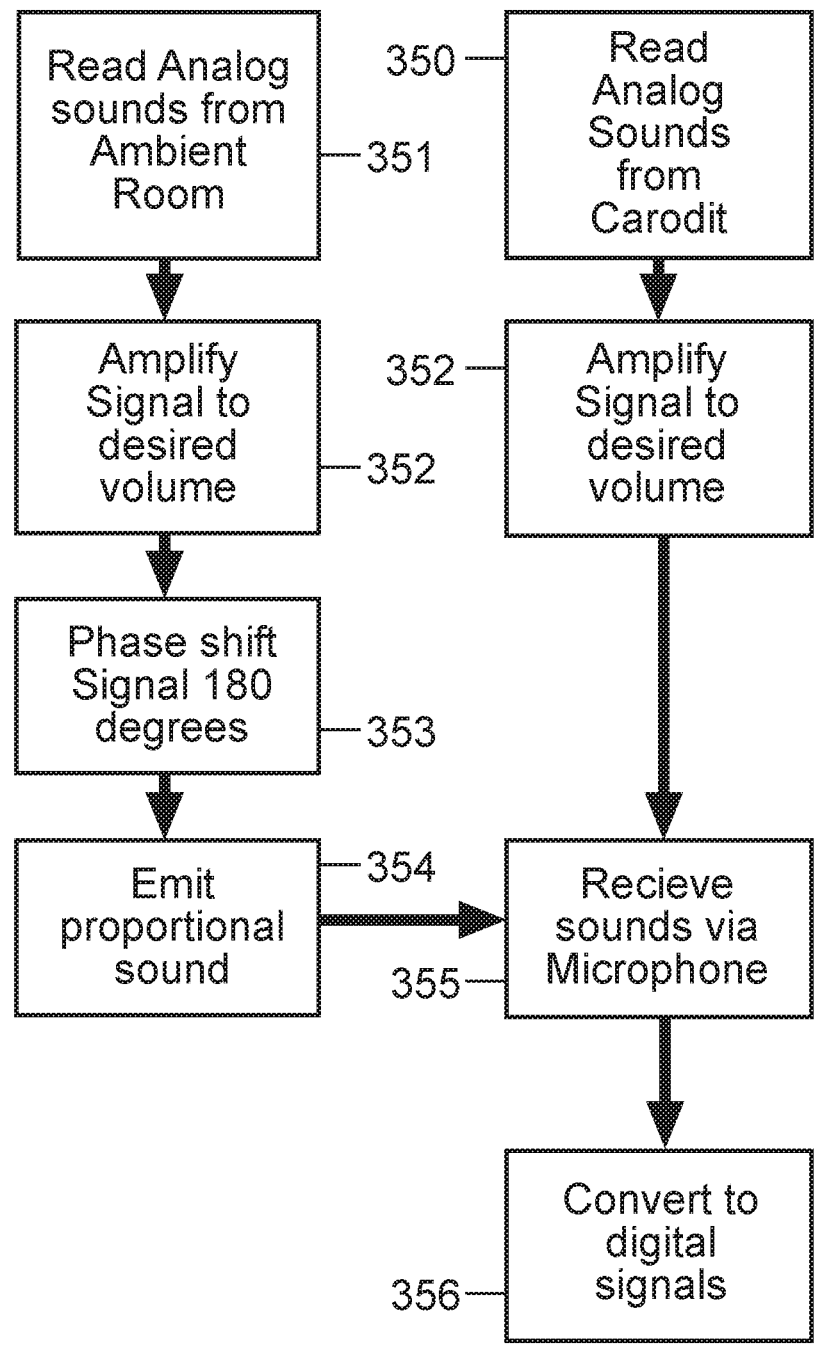
FIG. 33C depicts a flow-chart of an active noise cancellation process.
Figure 39:
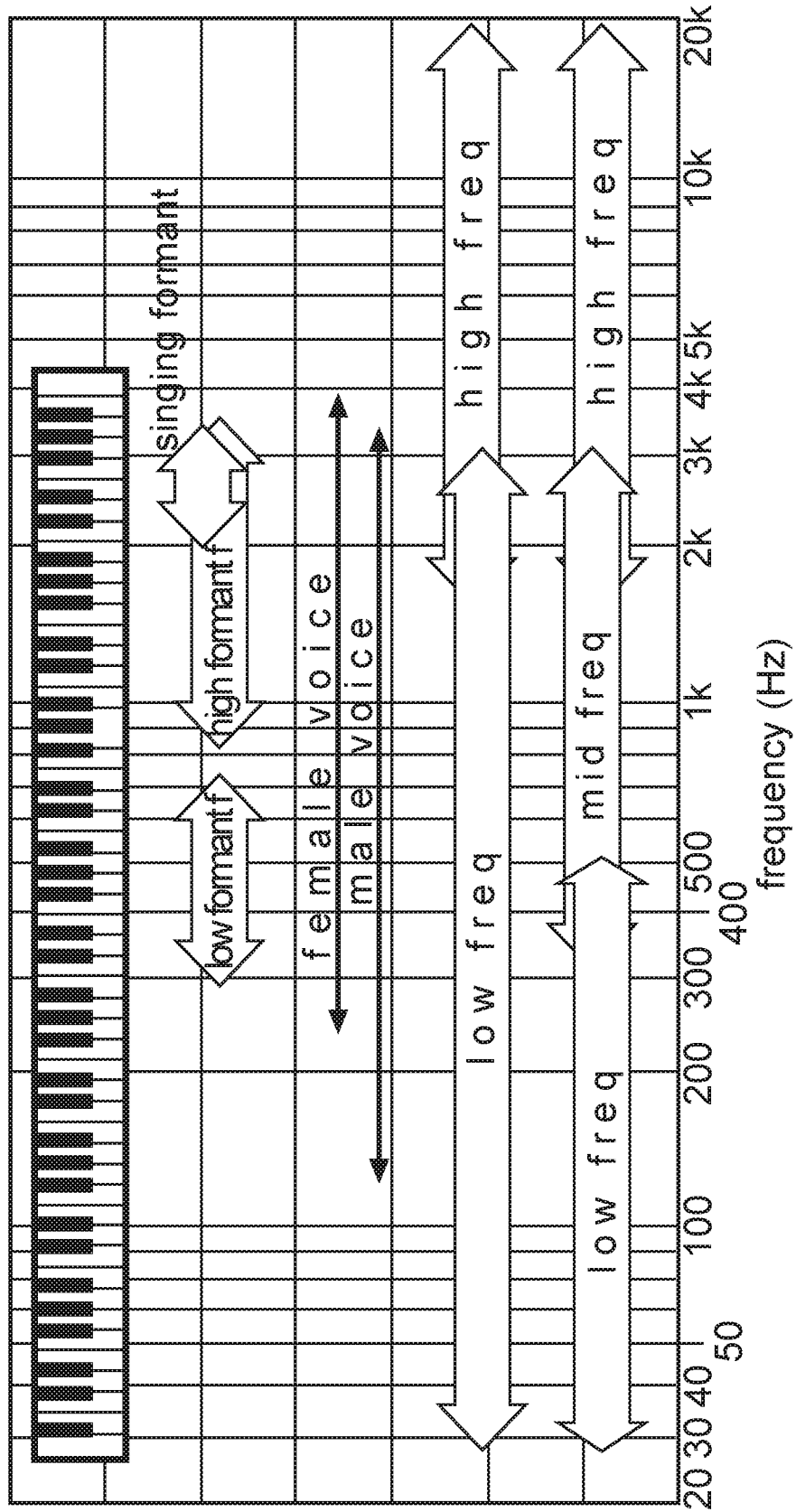
FIG. 39 depicts a chart showing a frequency chart.

In addition to the passive noise cancelling features of the sensor pod assembly, a further strategy for reducing noise to the piezo includes active cancellation of noise, such as found in the frequency chart of FIG. 39. Active noise cancellation can be produced through several different strategies. A first strategy utilizes a second microphone or piezoelectric device to measure ambient noise. For example, in FIGS. 34A-E, different variations of this strategy are provided. An overview of these strategies is depicted in flow charts of FIGS. 33A, 33B, and 33C FIG. 33A depicts an electronic diagram depicting a signal received 330, ambient noise 331 and a subtraction 332, wherein the ambient noise 331 is literally removed from the received signal 330 to generate the subtracted signal 332. FIG. 33B provides a further flow-chart of this concept. For example, box 340 defines reading the analog sounds from the ambient room, converting these to digital 342, converting to a frequency domain 343. In parallel, the analog signals are received from the carotid artery 341, or another artery of the circulatory system, converted to digital 342, converted to frequency domain 343, and then the ambient room sounds are subtracted from the sounds from the artery 344. The different in sound is then converted back to time domain 345, and the data is processed 346 to calculate occlusion or stenosis of the artery being reviewed.

Figure 36:
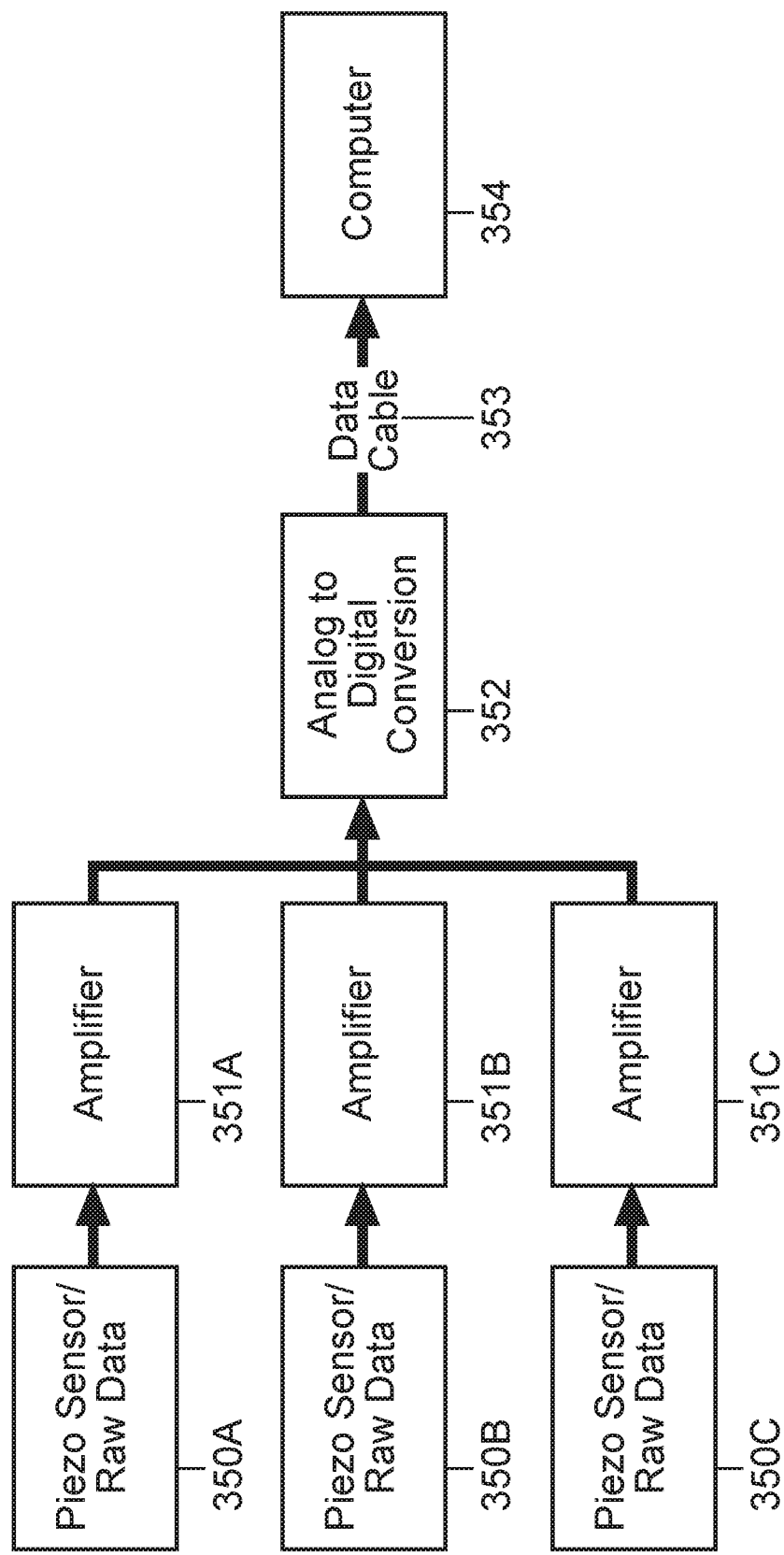
FIGS. 36, 37 and 38 depicts a flow-chart data collection, with 36 wired, 37 wireless from a single module, and 38 wireless from multiple modules.

FIG. 36 depicts an active cancellation flow chart. A sensor reads analog sounds from and ambient room 351. Parallel sensor reads analog sounds from the carotid artery 350. Each sound is amplified to a desired volume in 352. Signal from the ambient room 351 is phase shifted 180 degrees 353, and the phase shifted sound 353 is emitted 354. Sounds are received by a microphone 355 and converted to digital signals. This effectively removes the ambient sound 351 from the digital signal processed from the carotid 350.

Figure 37:
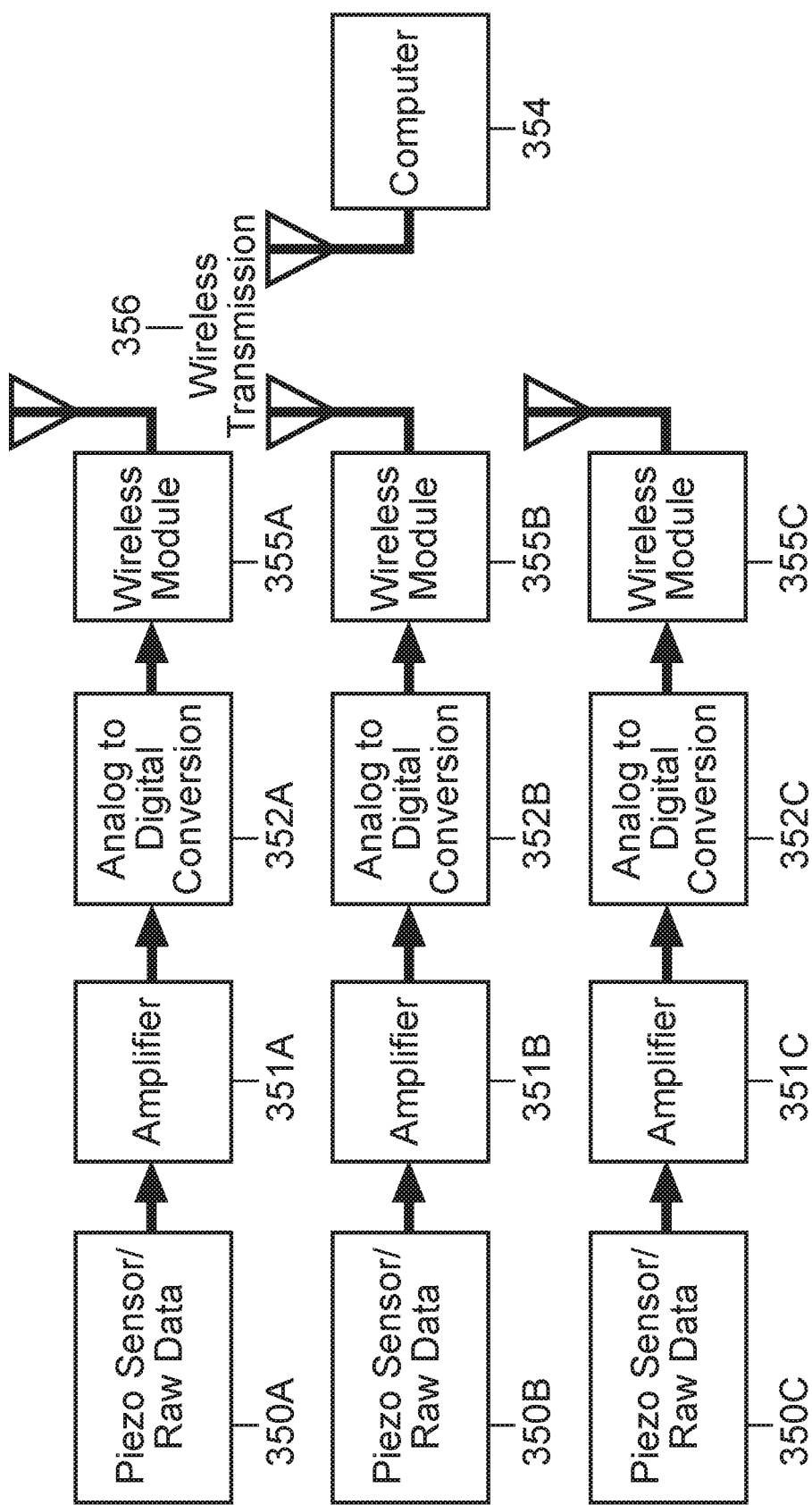

FIG. 37 depicts a chart using wireless modules, features 350A-C, 351A-C, 352A-C, 355A-C. Wireless transmission 365 sends signals to the computer 354.

Figure 34A:
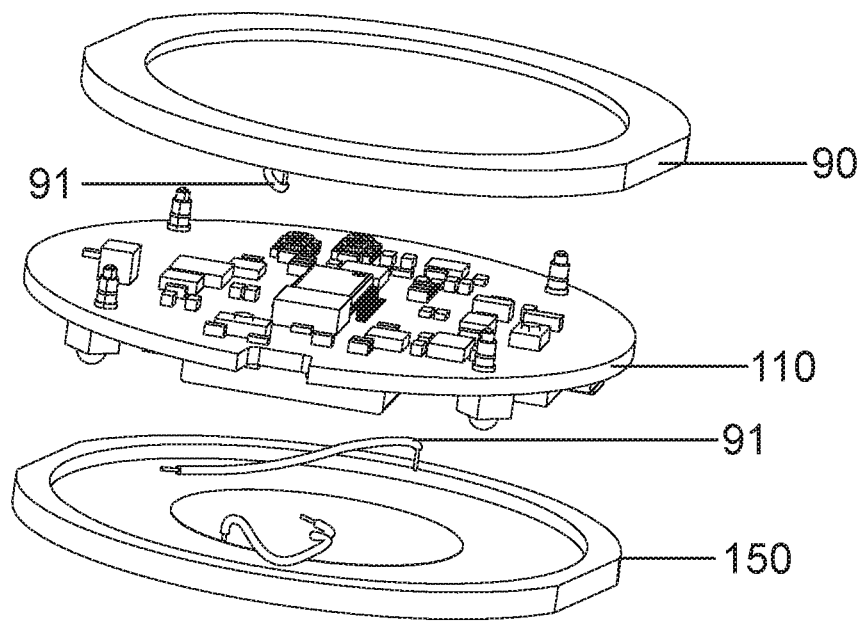
FIG. 34A depicting a double piezo assembly.

FIG. 34A depicts a paired piezoelectric device, having a first piezo 90, a board 110, positioned between the first piezo 90 and a second piezo 150. The first piezo 90 would engage to a disposable pad 18 and be placed against the skin of the patient. The sounds from the patient would be detected through the disposable pad 18 and by the first piezo 90. The first piezo 90 would also pick up ambient noise, as well as noise and harmonics from power lines, in the 60 Hz frequency. The purpose of the second piezo 150 is to detect these same ambient noises as the first piezo 90, but to not detect (or to detect at a much lower intensity) the sounds from the arterial circulatory system being investigated. The sounds from the second piezo 150 can then be compared to the sounds from the first piezo 90 to identify and eliminate background sounds from those from the arterial circulatory system. The subtraction process is depicted in flow-charts of FIGS. 33A-33C.

FIG. 8A depicts a further exploded view of FIG. 34A, and includes additional components. The piezo 90 engages to the piezo cap 100 with an adhesive 92 on a flange in the piezo cap 100. An adhesive 92 attaches the PCB contact board to the PCB board 110. Below the PCB board, is a second piezo 150, with is attached to the PCB board with a wiring harness 91. Both piezos can be contacted with a PCB board 105, and contact pins, as depicted in FIG. 8A. The second piezo 150, being isolated by the PCB board 110 then detects ambient sounds and not the sounds from the patient.

Cancellation and subtraction of sound can be accomplished in two ways. First, the sounds from the second piezo can be inversed and literally subtracted from the first piezo. Second, the sounds can be eliminated in analog by sending in a negative background signal which eliminates the sound. The prior art details several noise cancelling headphones, which use an external microphone to detect sound. This sound is then processed by a computing system with the device, and identifies and generates an out of phase sound, being out of phase by 180 degrees. This, when combined with the external sound, effectively cancels out the sounds that are received. Either method is functional, though the subtraction method may be preferable in certain embodiments.

Figure 34B:
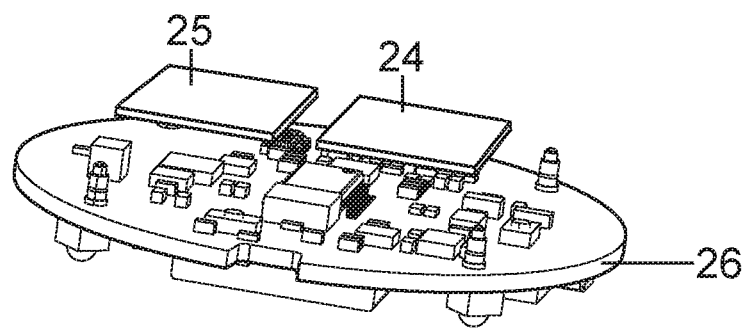
FIG. 34B depicting a parallel piezo assembly.
Figure 34C:
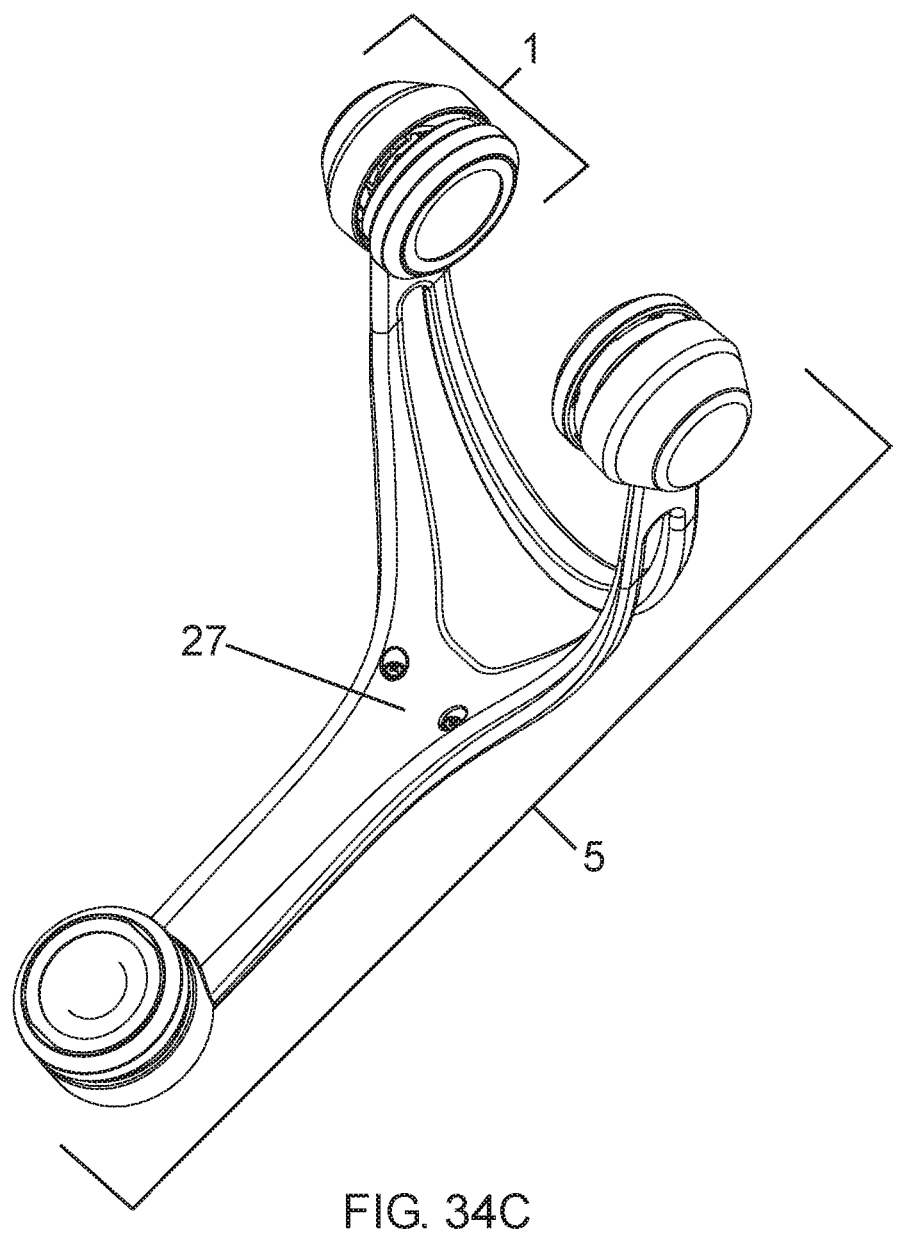
FIG. 34C depicting a microphone on an array.

FIGS. 34B, 34C, 34D, and 34E each detail a slightly different strategy for identifying ambient sounds for active cancellation. For example. FIG. 34B depicts a parallel piezo setup, comprising a base chip 26 and a first piezo 24 and a second piezo 25, arranged in parallel. This setup will allow for detection of stenosis along a linear path and determining of position of an occlusion between the two piezo sensors. This occurs as each piezo will detect the same sounds, but receive them at slightly different times. This allows for positional identification of the underlying blockage. Furthermore, one piezo may be contacted with the sensor pad 18 and a second not, thus allowing for subtraction strategies.

FIG. 34B depicts an array 5 comprising three sensor pods 1, and a microphone 27 on the body of the array. In this manner, the microphone 27 can pick up ambient sounds, but will be separated from the sounds of the arterial circulatory system that is being investigated. The microphone 27 can be any ordinary microphone or can be a copy of the piezo that is each of the sensor pods 1 so that the sounds can be closely matched.

Figure 34D:
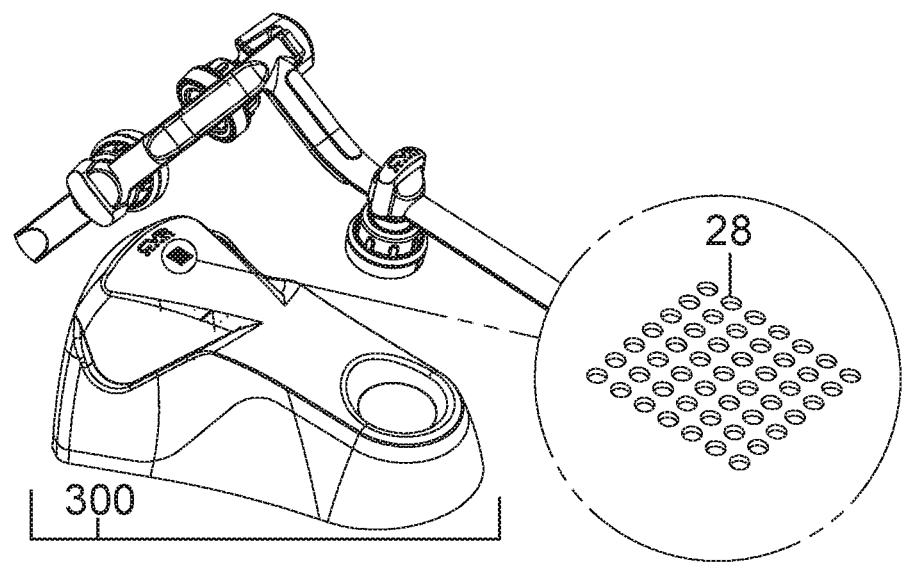
FIG. 34D depicting a microphone on a base.
Figure 34E:
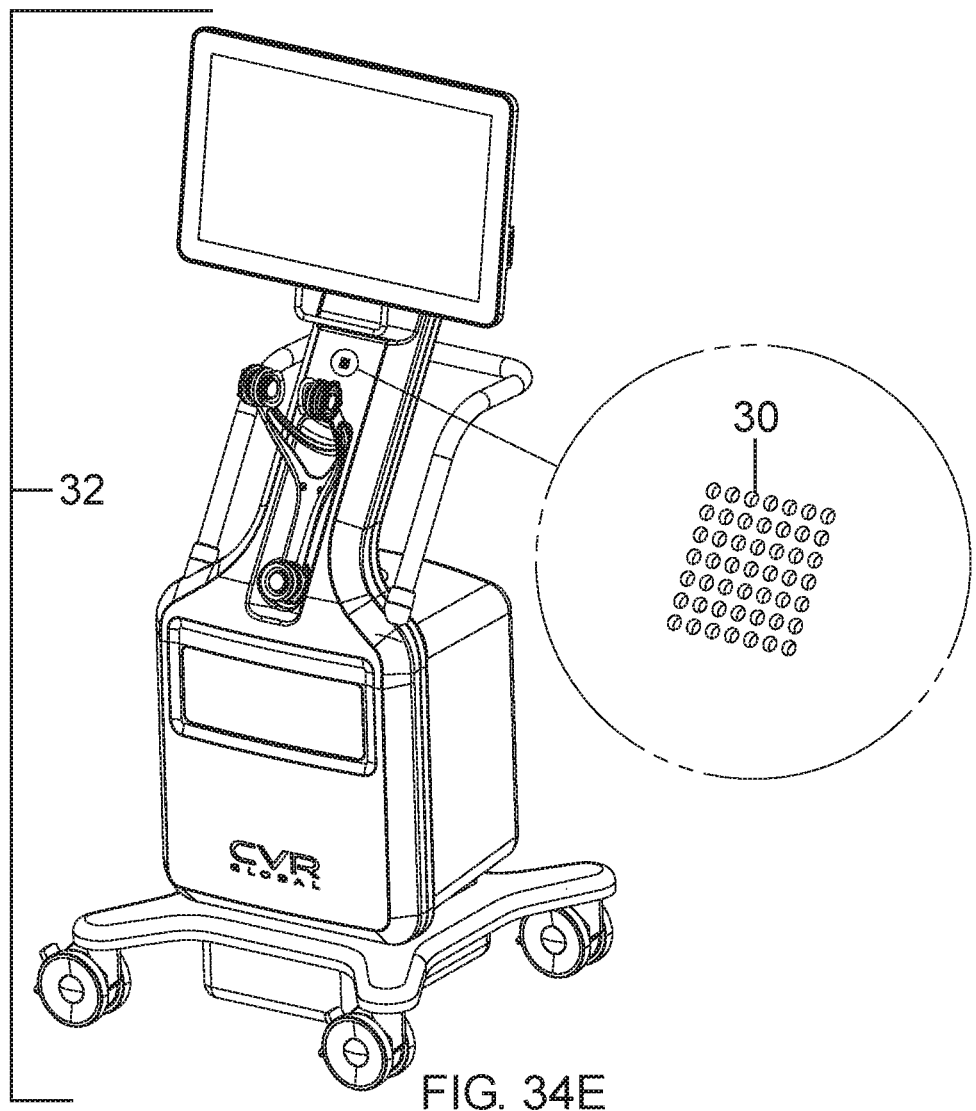
FIG. 34E depicting a microphone on a cart.

FIG. 34D depicts a microphone or piezo 28 depicted on a base 300. FIG. 34E depicts a microphone 30 or piezo on a cart 32 device.

A particular method comprises a method of reducing noise to a sensor comprising: engaging a first sensor to a patient and a second sensor to ambient air, adjacent to said first sensor; detecting noises from said patient and simultaneously detecting noises from ambient air with said second sensor; subtracting the noise from said second sensor from the data from said first sensor, which will remove the ambient noise from the data from the first sensor.

A particular method utilizes a phase change detected from a sensor to modify the sounds received at an adjacent sensor; a first sensor placed on a patient to detect sounds from the patient; a second sensor placed adjacent to said first sensor but shielded from the sounds of the patient; performing a phase change on the sounds received in said second sensor and emitting a proportional sound in said phase change.

Analysis Based Noise Filtration Methods

Active and passive cancellation can provide for a dramatic reduction in the amount of noise that ends up in a set of collected data. However, even with these background strategies to reduce and eliminate noise, detection of low frequency sounds can often be understood as looking at sounds that are "in the weeds." Accordingly, further processing may be necessary, in certain embodiments, to collect data, amplify the data and perform certain analysis using a computer to clarify the data for best analysis.

Spectrum analysis, also referred to as frequency domain analysis or Power Spectral Density ("PSD") estimation, is the technical process of decomposing a complex signal into simpler parts. As described above, many physical processes are best described as a sum of many individual frequency components. Any process that quantifies the various amounts (e.g. amplitudes, powers, intensities, or phases), versus frequency can be called spectrum analysis.

Spectrum analysis can be performed on the entire signal. Alternatively, a signal can be broken into short segments (sometimes called frames), and spectrum analysis may be applied to these individual segments. Periodic functions (such as sin(t) are particularly well-suited for this subdivision when t (time) includes several cycles. General mathematical techniques for analyzing non-periodic functions fall into the category of Fourier analysis.

The Fourier transform of a function produces a frequency spectrum which contains all of the information about the original signal, but in a different form. This means that the original function can be completely reconstructed (synthesized) by an inverse Fourier transform. For perfect reconstruction, the spectrum analyzer must preserve both the amplitude and phase of each frequency component. These two pieces of information can be represented as a 2-dimensional vector, as a complex number, or as magnitude (amplitude) and phase in polar coordinates (i.e., as a phasor). A common technique in signal processing is to consider the squared amplitude, or power. In this case the resulting plot is referred to as a power spectrum.

In practice, nearly all software and electronic devices that generate frequency spectra apply a Fast Fourier Transform ("FFT"), which is a specific mathematical approximation to the full integral solution. Formally stated, the FFT is a method for computing the discrete Fourier transform of a sampled signal.

Because of reversibility, the FFT is called a representation of the function, in terms of frequency instead of time; thus, it is a frequency domain representation. Linear operations that could be performed in the time domain have counterparts that can often be performed more easily in the frequency domain. Frequency analysis also simplifies the understanding and interpretation of the effects of various time-domain operations, both linear and non-linear. For instance, only non-linear or time-variant operations can create new frequencies in the frequency spectrum.

The Fourier transform of a stochastic (random) waveform (noise) is also random. Some kind of averaging is required in order to create a clear picture of the underlying frequency content (frequency distribution). Typically, the data is divided into time-segments of a chosen duration, where time is long enough to include several cycles of typical frequencies, and transforms are performed on each one. Then the magnitude or (usually) squared-magnitude components of the transforms are summed into an average transform. This is a very common operation performed on digitally sampled time-domain data, using the discrete Fourier transform. This type of processing is called Welch's method or Entropy Maximum (Burg) method. These methods are known and understood by a person of ordinary skill in the art. When the result is flat, it is commonly referred to as white noise. However, such processing techniques often reveal spectral content even among data which appear noisy in the time domain.

Accordingly, by taking a piezoelectric unit, capable of measuring sounds and vibrations at low amplitude and within a particular frequency range, we can measure the wall pressure fluctuations due to stenosis. Accordingly, the sensitive piezoelectric devices combined with amplifiers are placed onto the skin above the carotid artery and the piezoelectric device detects these sounds. The detected sounds are then passed through analog to digital converters before reaching a computer in which further amplification and an analysis of the signal occurs.

In the case of the arterial circulatory system, the piezo is placed on the skin above the artery in the region of a suspected stenosis. In the case of a carotid artery the placement would be on the neck, slightly below the ear. The particular placement of the piezo and the location of the stenosis is suggested by Fredberg and Borisyuk. Indeed, in an artery, between the stenosis and the region where turbulence has significantly decayed, the intensities can be rather large, where the wall can be subjected to large fluctuating stresses imposed by the turbulent blood flow. [Fredberg 1974] The distance over which this occurs is estimated to be about 12D downstream, where D is the normal diameter of the carotid artery. Borisyuk [2010]. For a typical internal carotid D of 0.5 cm, that distance would be of the order of several cm.

Detection of vortices generated due to flow in the carotid artery produce low intensity sounds that are related to development of stenosis in an artery. These low intensity sounds are sometimes difficult to detect and to pull out of the mass of noise being generated by the body. Accordingly, a highly specialized detection device using piezo devices for arteries that are near the surface. In the relevant frequency range of 20 Hz to about 3000 Hz the wavelengths are long compare to other lengths, such as artery length or thickness of tissue between the artery and the skin. In this case the surface is still within the "near field" of a wave (much closer than one wavelength), in which case the tissue acts as an incompressible medium. The energy in the near field of a wave is attached to the source and cannot propagate away. Thus there is no net energy flux out from the source. Because near-field pressure fluctuations cannot propagate away, they are generally called "pseudo-sound".

Borisyuk [2010] has been able to relate the shape of the power spectrum at the surface to the vortex structures in the blood flow distal to a constriction. He divides the region distal to a constriction into three: Region I. The flow separation region, in which a jet flow of higher velocity, in the center, acts separately from the slower flow outside the jet. Region II. The flow reattachment region. The two regions, I and II, constitute the "most disturbed flow region". The length of the first two regions, I plus II, based upon extensive calculations, Borisyuk estimates to be less than 7D, where D is the normal diameter of the artery. Here, stenosis may be detected in several different arteries in the arterial circulatory system. For example, detection may be directed towards detecting stenosis in the Internal Carotid Artery (ICA) in an adult, in which D is approximately 0.7 cm but the internal carotid is typically 0.5 cm. Therefore, the total length of the regions spoken of, I and II, would be at most about 3.5 cm. Region III is the region of flow stabilization where flow develops into the less turbulent flow farther upstream. This region extends from at most, 7D to 12D, or in the case of the ICA, at most from about 3.5 cm to about 6 cm.

Conservation of fluid requires that $v=V (D/d)^2$. Let lower case v be the flow velocity inside the constriction and capital V the flow velocity past the constriction. Let d be the diameter of the flow inside the constriction. Borisyuk suggests estimates of two characteristic ring vortex frequencies. The first, f1, of vortices inside the jet, with typical size d; the second, f2, of vortices between the jet and the outer wall, with typical size, D.

Accordingly, Borisyuk provides for a broad disclosure that certain structures in the blood generate flow patterns. Based on these flow patterns, and separated into three regions, Borisyuk estimates characteristics of vortex frequencies. However, these estimations provide only a rough estimate as to a vortex structure.

Accordingly, our method for determining stenosis consists in connecting the frequencies associated with largest intensities in the spectral domain to three frequencies, f1 thru f2 in order to obtain estimates of percentage stenosis of the artery, $(1-d/D)\times100$.

The method has been implemented in a computer language we convert to binary, encrypted to be packaged as one whole product, software and hardware. The particular software used to run the data analysis can be determined by a person of ordinary skill in the art.

A particular embodiment comprises the following steps: A sensor device is placed on a patient and data is sampled from the patient and the sound/vibrations are converted from analog to digital. The data is streamed from the device with both of the sensors in one data stream. We break the data stream down into two streams, one for the left sensor and one for the right. We then begin the Wavelet analysis which takes out noise. After the Wavelet removes the noise a power spectral density analysis is done and we are given a power spectral density (PSD). This tells us what frequency noise is found within the data and how strong/powerful the noise is. Because the PSD gives transient noise smoothing the PSD must be done to correctly identify the strongest peaks within the data. After smoothing is done peaks are determined and based on the where the peaks are will determine the amount of stenosis or whether no stenosis is present. If there is one peak, No stenosis is present. If there are two or more peaks the patient has some stenosis present.

Wavelets have been frequently used in digital signal processing and are often known as small waves. A wavelet is a real-valued integral function $\psi$: $R \to R$ satisfying $Z\psi(t)$ dt=0. For practical applications, it has n vanishing moments: $Z\ t\ p\psi(t)\ dt=0$, p=0, 1, . . . , n−1. Consider the following family of dilations and translations of the wavelet function $\psi$ defined by $\psi jk(t)=2-j/2\psi(2-j\ t-k)$, j, k=0, ±1, ±2. The terms j and 2j are called the octave and the scale, respectively. By construction, this family consists of orthogonal basis functions in the sense that for a given time series or observed signal or simply data y(t), it can be written as the sum of these basis functions in a unique way: $y(t)=X\ j\ X\ k\ djk\psi jk(t)$, where djk is the discrete wavelet transform (DWT) of y(t) given by $djk=Z\ y(t)\psi jk(t)\ dt$, j, k=0, ±1, ±2. In practice, data is decomposed into its rough approximation at the chosen resolution level J (signal of interest) and details on a finite number of resolution levels j(≤J). The latter will be considered as noise. Denoising is equivalent to removing the details to allow for improved fit and prediction of peaks in a PSD plot.

Figure 38:
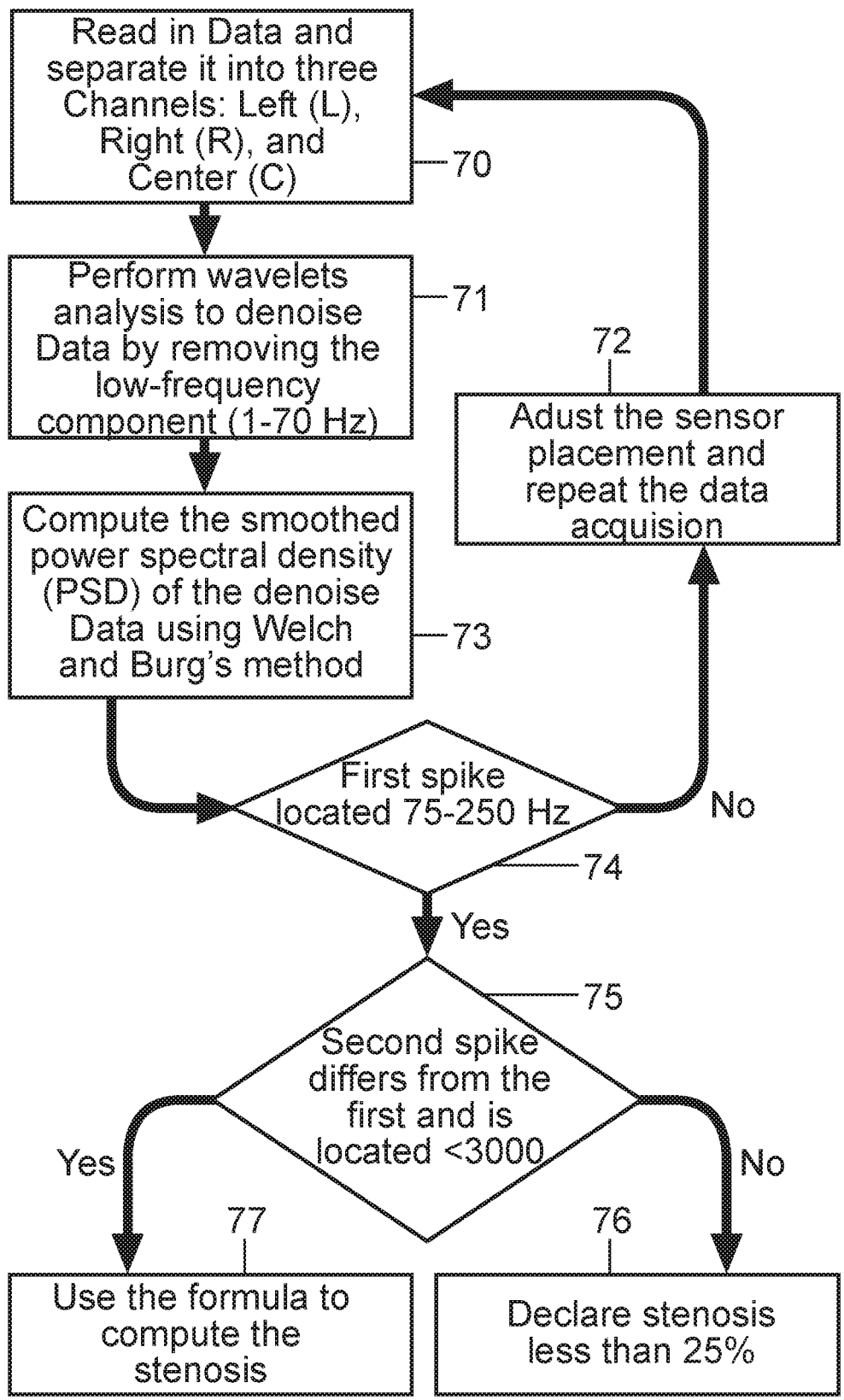

An Example of the Process for Calculation:

FIG. 38 details a flow-chart of the process for de-noising a sample after the passive and active noise cancellation steps. A first step is to read in data and separate it into different channels 70, based upon the number of piezo sensors. A single sensor will have only one channel, two sensors two channels, and three, as in FIG. 38, three channels, etc.

We next perform a wavelet analysis 71, to de-noise the data by removing low-frequency components 1-60 or 1-70 Hz. After the wavelet analysis we generate a Power Spectral Density (PSD) 73 using the denoised data, in combination with Welch and/or Burg's method. From this PSD plot, we detect a first spike, typically between 75-250 Hz, (74) though it can go as low as 60 Hz. Where lower peaks are present, the Wavelet is re-run to remove a lower set of data, so that the first peak is not obfuscated.

If a first spike is present between 75 and 250 Hz, we continue data acquisition (74). In certain embodiments, if there is no spike in this range, the sensor is adjusted (72) and the data acquisition process is re-started. Using this embodiment, we effectively build in a mechanism to ensure proper placement of the sensor, to make sure we have good quality data. However, other sounds may be utilized as a predetermined sound for ensuring proper placement in other embodiments.

Once we have a first spike between 75 and 250 Hz, a second spike is analyzed (75), as different from the first and less than 3000 Hz. (feature 75). If the second spike is not found in this range, we declare stenosis at less than 25%. If the second spike is in this range, then we can calculate stenosis by peak comparison using the formula. We use the formula (1−f1/f2)×1100%, where f1 is the base frequency for the ring vortices in the artery (between 60 and 260 Hz) and f2 is the frequency from the restricted ring vortices (below 3000 Hz). If f1 is not present, the artery is too stenosed to show a base ring vortex and therefore we conclude there is a very high level of stenosis. If f2 is not present then we conclude that there is insufficient stenosis to create a restricted ring vortex and thus we say there is a very low level of stenosis. If neither f1 nor f2 are present, the patient is stenosed to the point where ring vortices can no longer form. This patient has extremely high stenosis and needs to see a specialist as soon as possible.

Example of Data Analysis

Read in data and look for extraordinary features. The step is important for reviewing if the device has followed protocol or not, and whether the subject has complied with the data acquisition procedures.

The function CVRData provides a pop-up menu asking a user to select data, followed with a graph plotting channels, selected from Left—channel 1, Right—channel 2, or center—channel 3. One or all channels can be selected.

Figure 40:
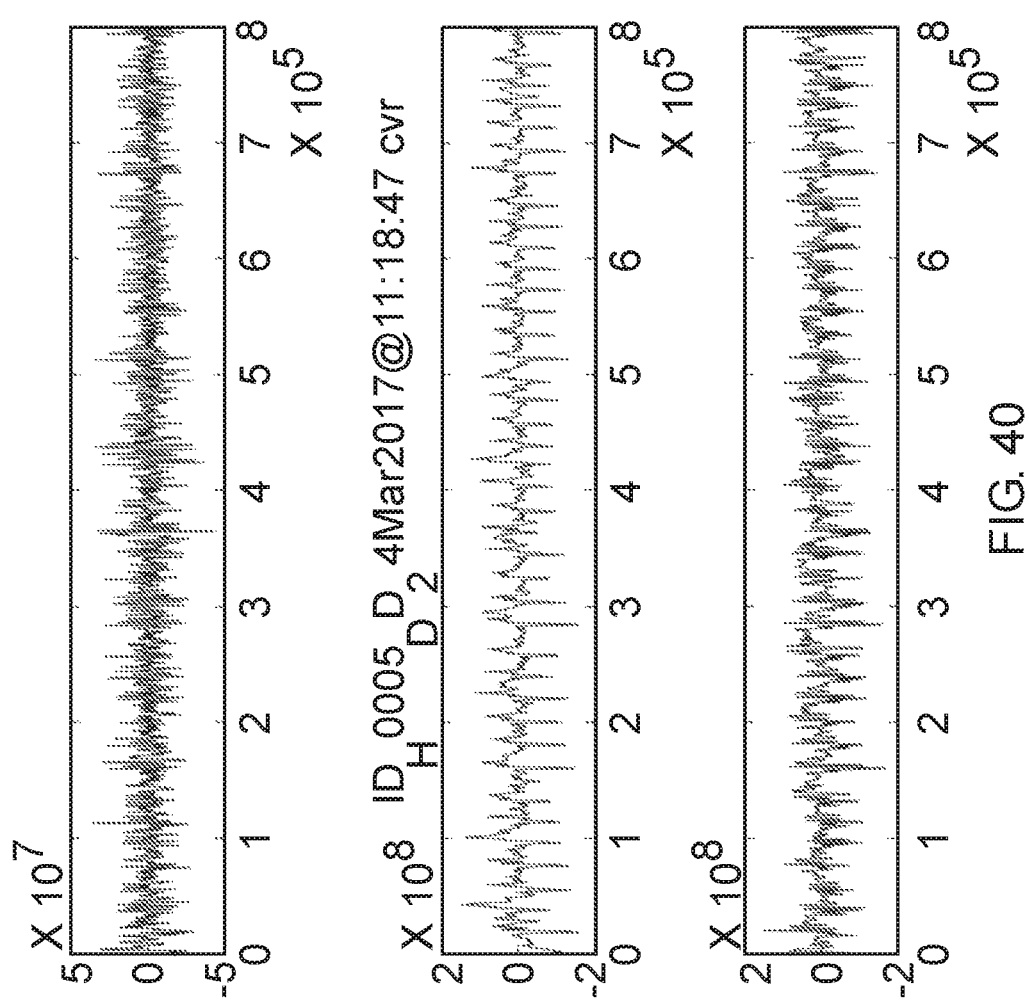
FIG. 40 depicts certain raw data from three channels.

The data of FIG. 40 depicts wherein y=CVRData. The variable y contains all three channels. Additional analysis in selecting channels is provided in a further step. The output of FIG. 10 was constructed from "plot3ch.m". The subject ID appears in the title of the last panel.

To select a channel to analyze, we look at the following aspects:

Ch=1; note that Left or Ch=1, Right or Ch=2, and center or Ch-3.

Setup of basic parameters for data analysis. Variable x is one of the channels in the following formula x=y(ch:3: length(y));

Fs is the sampling rate, wherein Fs=20,000;

One second record: the variable t is used for data visualization by plotting the first Fs or one second record of the channel values. Accordingly we can use the data:

t=(0:Fs)/Fs; subplot(111), plot(x(1:10*Fs)), title ('Ten second channel plot')

Figure 41:
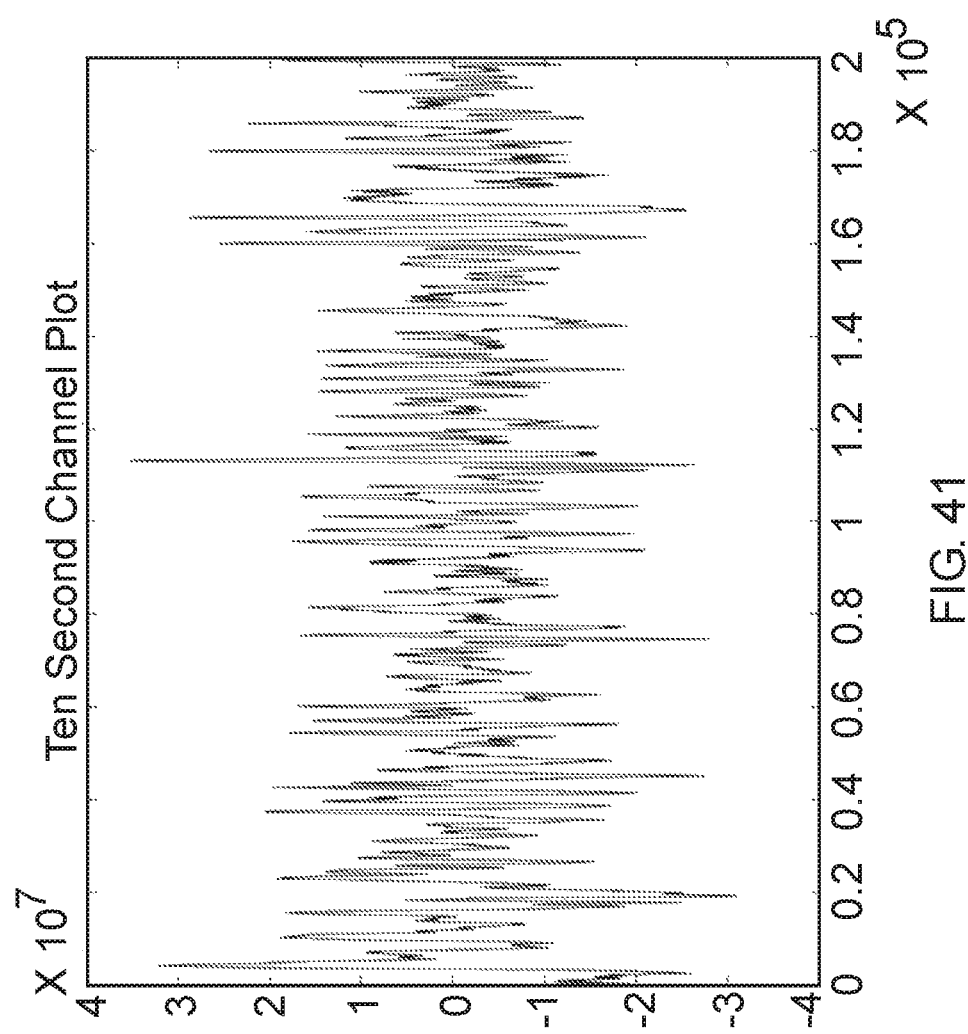
FIG. 41 depicts a ten second channel plot.

The resulting channel plot is depicted in FIG. 41.

A periodogram is generated. In general, one way of estimating the PSD of a process is to simply find the discrete-time Fourier transform of the samples of the process (usually done on a grid with an FFT) and appropriately scale the magnitude squared of the result. This estimate is called the periodogram.

Periodogram(x, hamming(length(x)), length(x), Fs); xlabel('Frequency (Hz)').

Figure 42:
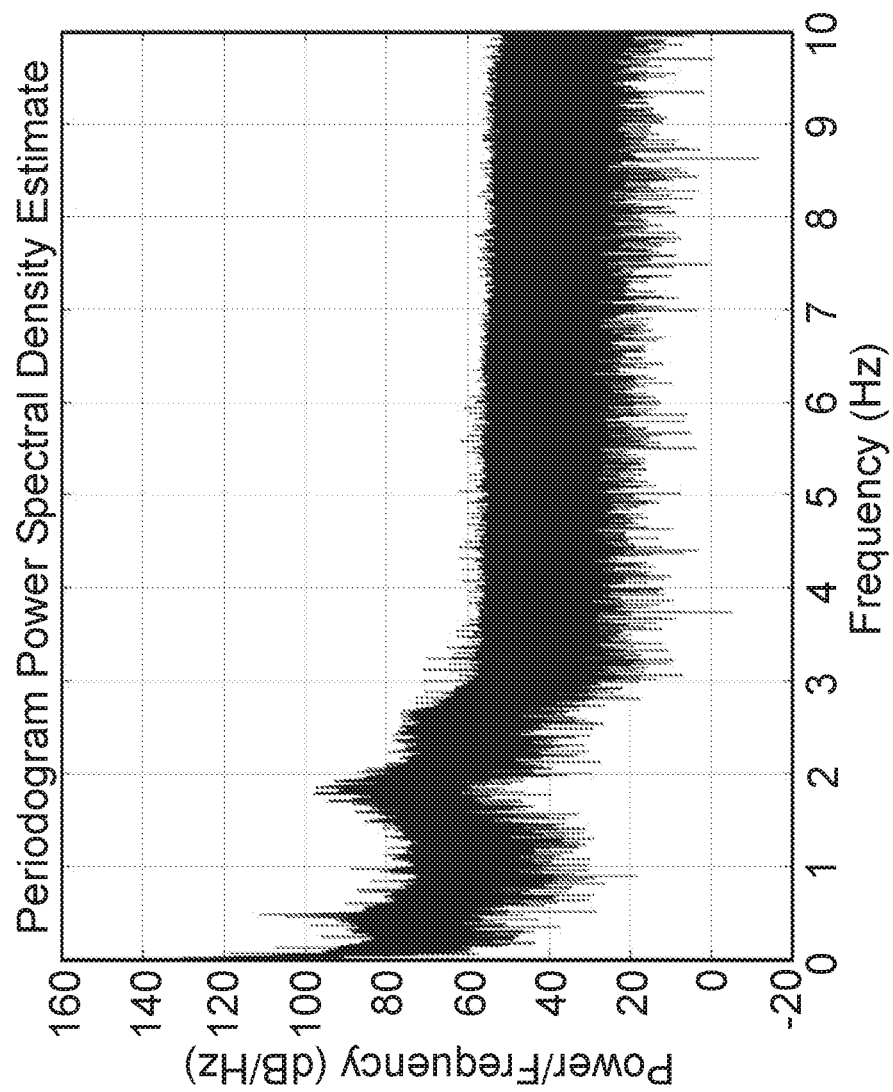
FIG. 42 depicts a PSD periodogram

FIG. 42 depicts the periodogram PSD estimate.

The number of frequencies plotted is 1+half of length (x) and the unit is Hertz (Hz).

Welch's Method can be used as an improved estimator of the PSD. Welch's Method, as known to a person of ordinary skill in the art, consists of dividing the time series data into (possibly overlapping) segments, computing a modified periodogram of each segment, and then averaging the PSD estimates. The result is Welch's PSD estimate.

The averaging of modified periodograms tends to decrease the variance of the estimate relative to a single periodogram estimate of the entire data record. Although overlap between segments introduces redundant information, this effect is diminished by the use of a nonrectangular window, which reduces the importance or weight given to the end samples of segments (the samples that overlap).

Figure 43:
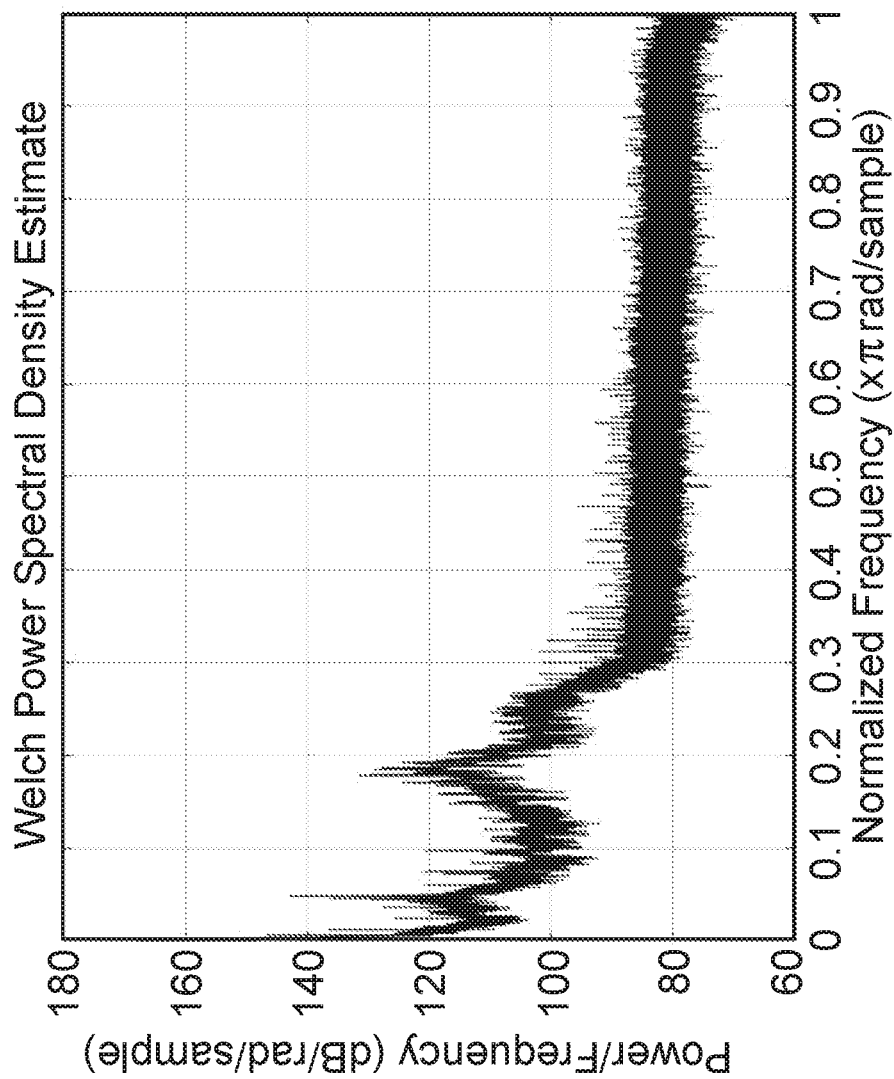
FIG. 43 depicts Welch's Power Spectral Density estimate.

However, as mentioned above, the combined use of short data records and nonrectangular windows results in reduced resolution of the estimator. In summary, there is a tradeoff between variance reduction and resolution. Once can manipulate the parameters in Welch's method to obtain improved estimates relative to the periodogram, especially when the SNR is low. This is illustrated in the following example:

A signal such as x consisting of the left channel data pwelch(x); which is graphically represented in FIG. 43.

The graph of FIG. 43 depicts the normalized frequency.

Parameters to be specified with the Welch's method must be considered. The first parameter is the segment length. Default length is (x)/8. In code we use SGM=100,000. The next parameter is percent of overlaps: novoerpals=50,000.

Through these elections we obtain Welch's overlapped segment averaging PSD estimate of the preceding signal. Use a segment length of 100,000 samples with 50 overlapped samples. Use 1+length(x)/2 DFT points so that 100 Hz falls directly on a DFT bin. Input the sample rate to output a vector of frequencies in Hz. We can plot the result.

Figure 44:
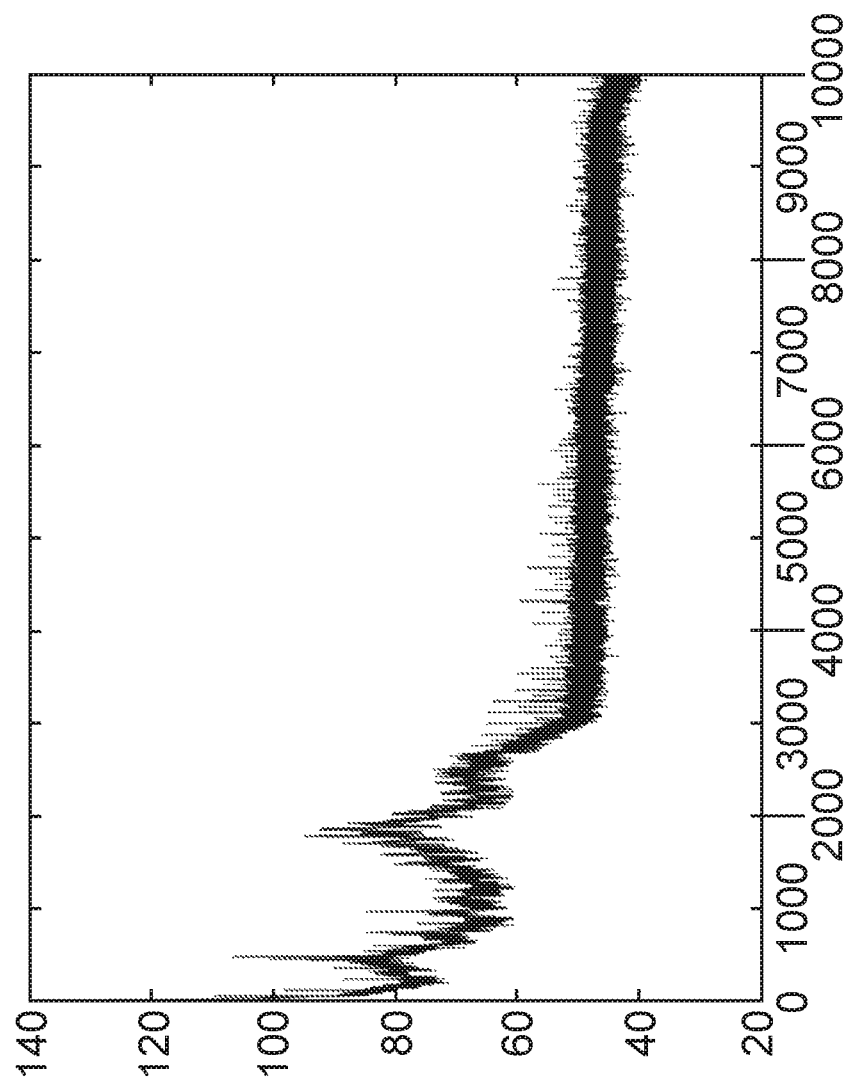
FIG. 44 depicts additional data plot of Welch's method.

Example: [Pxx,F]=pwelch(x, sgm, noverlaps, [ ], Fs); plot (f, 10*log 10(Pxx)). The result is the plot of FIG. 44.

We can further estimate PSD through autoregressive PSD estimate through use of Burg's Method. Burg's Method is a parametric method for estimating PSD. Below returns a frequency vector, F, in cycles per unit time. The sampling frequency, Fs, is the number of sample per unit time. If the unit of time is seconds, then F is in cycles/second (Hz). For real-valued signals, F spans the interval [0,fs/2] when nfft is even and [0,fs/2] when nfft is odd.

The following formula assumes an AR(50) model to the data.

Figure 45:
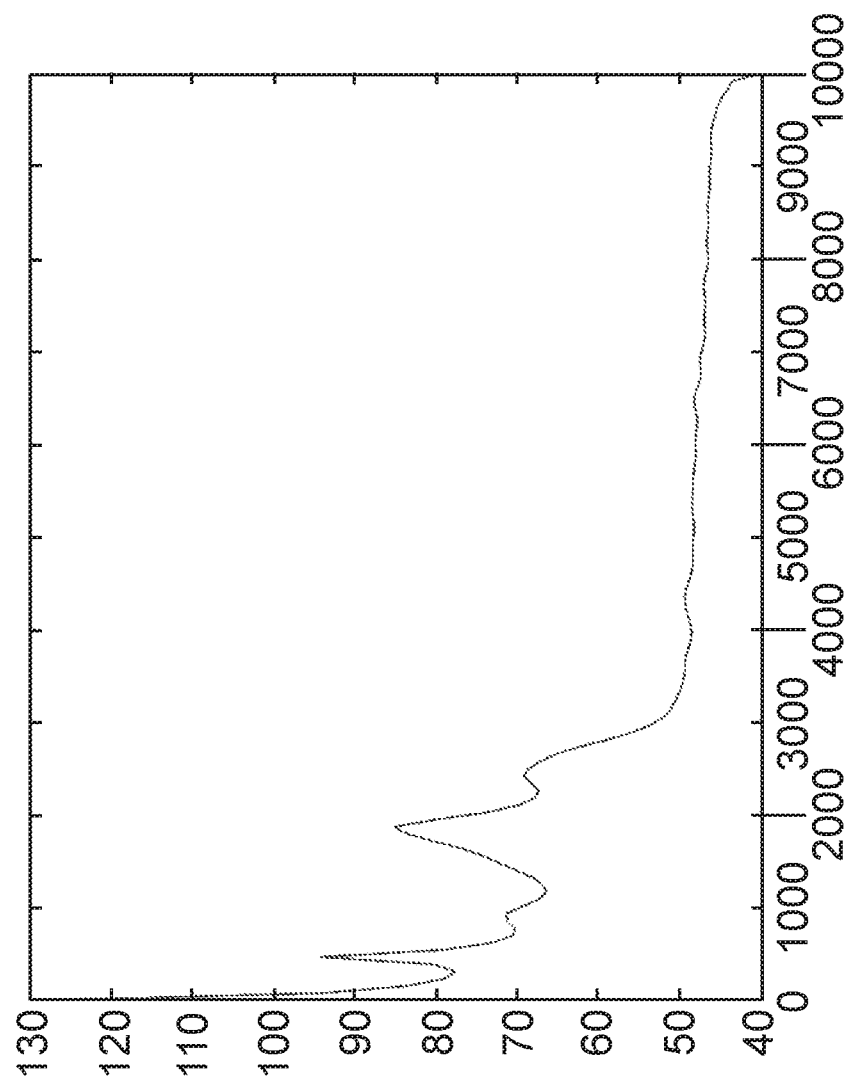
FIG. 45 depicts Burg's method of smoothing.

[Pxx,F]=pburg(x, 50, [ ], Fs); plot(F,10*log 10(Pxx)). The result is plotted in FIG. 45. A comparison between FIGS. 14 and 15 shows a much clearer set of peaks, allowing clearer determination of the stenosis.

We use AR(50) because we tested model orders starting from 5 through 50 and determined that AR(50) provided the cleanest data result.

Reflection Coefficients for Model Order Determination

The reflection coefficients are the partial autocorrelation coefficients scaled by −1. The reflection coefficients indicate the time dependence between y(n) and y(n−k) after subtracting the prediction based on the intervening k−1 time steps.

Use of arburg to determine the reflection coefficients. Use the reflecting coefficients to determine an appropriate AR model order for the process and obtain an estimate of the process PSD. We use the following formula:

$[a,e,k]$=arburg$(x,50)$;

Stem(k, 'filled'); title('Reflection Coeficients'); xlabel ("model Order')

Figure 46:
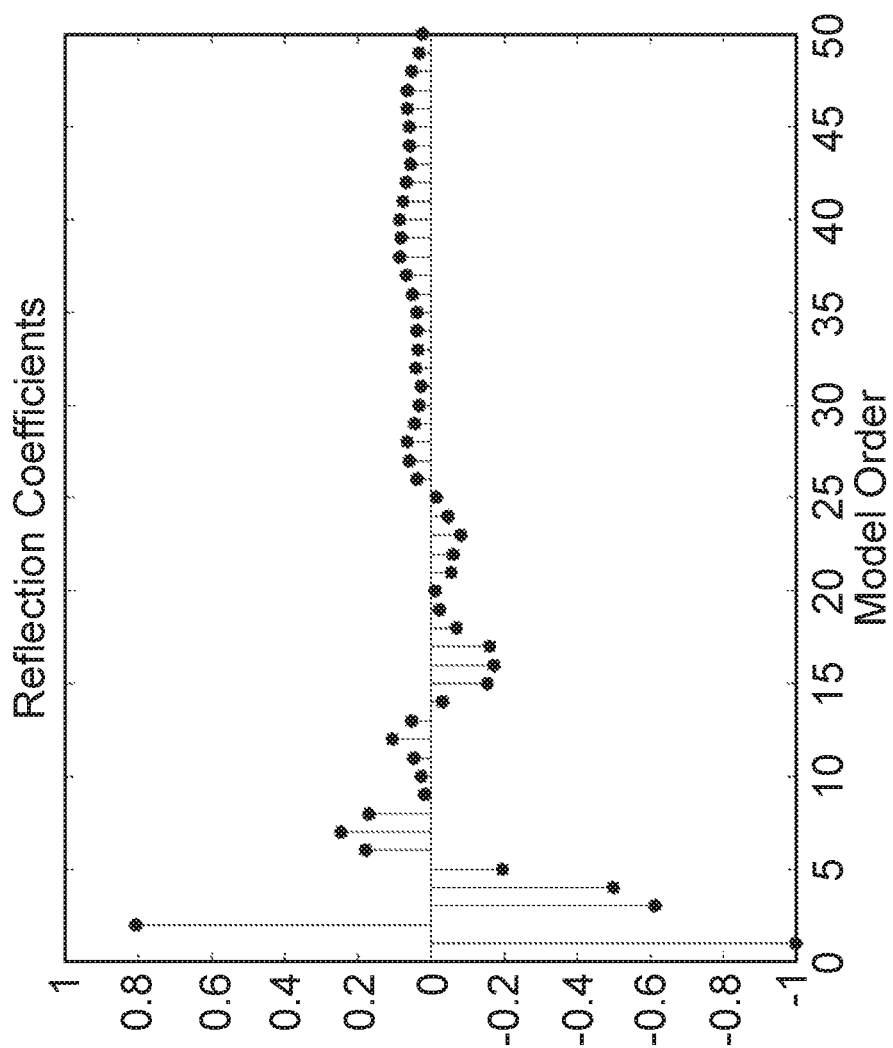
FIG. 46 depicts Reflection Coefficients.

FIG. 46 depicts the resultant Reflection Coefficients.

To find frequencies, we zoom into the data. Bf=0.1000/ 129:3876

Plot(0:1000/129:3876, 10*log 10(Pxx(1:51)))

Figure 47:
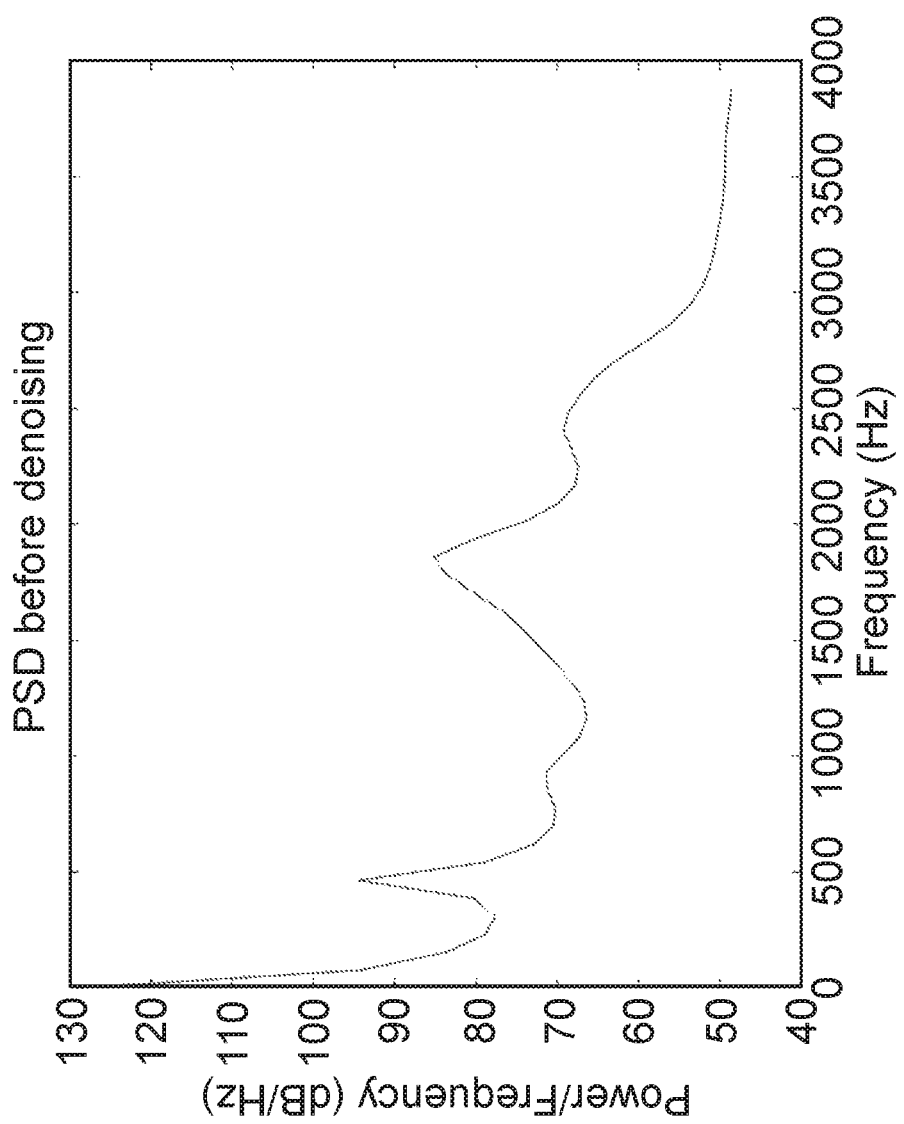
FIG. 47 depicts a PSD before denoising.

Legend ('pburg PSD Estimate'); x label ('Frequency (Hz)'); y label ('Power/frequency (dB/Hz)'); title ('PSD before denoising'). The result is the data of FIG. 47.

Figure 48:
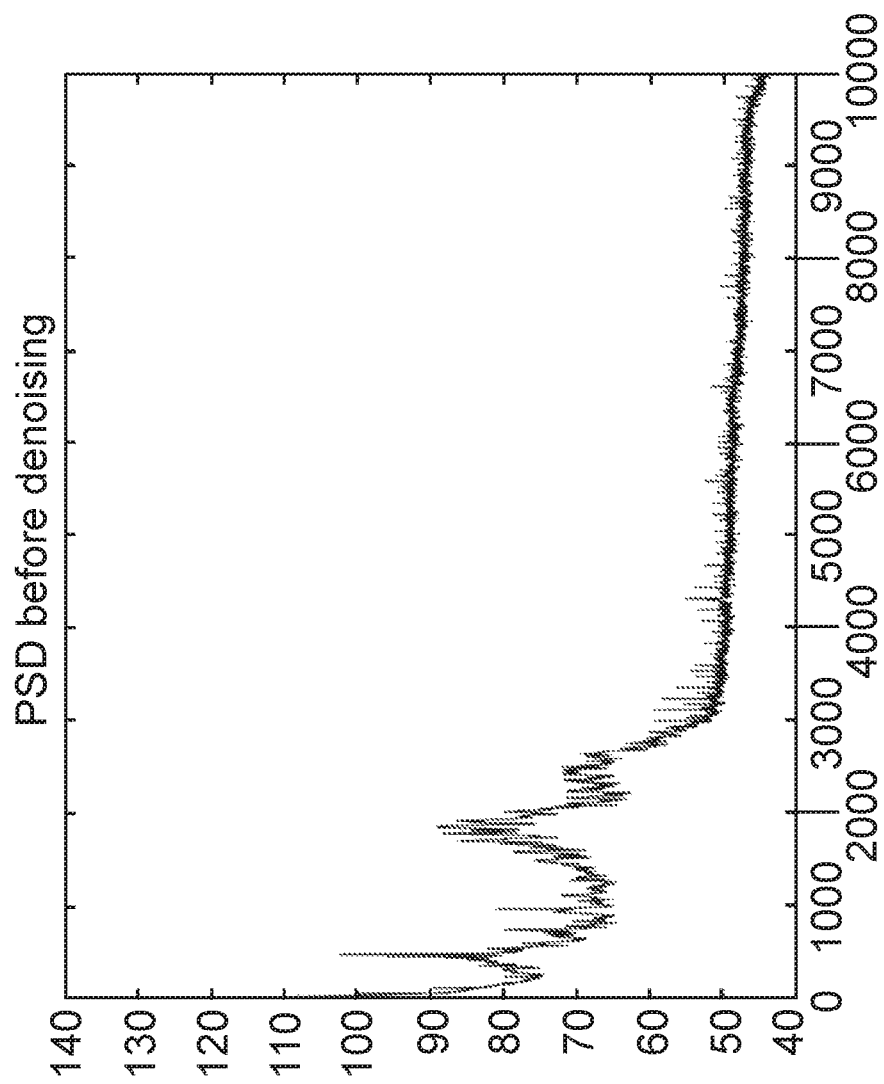
FIG. 48 depicts a PSD before denoising.

We can then experiment with several choices of parameters in the Welch's PSD estimate, for example with 20 percent overlaps. Sgm=10,000; noverlaps=2000; [Pxx,F]= pwelch9x, sgm, noverlaps, [ ], Fs); plot(F, 10*log 10(Pxx)). This results in the plot of FIG. 48.

Figure 49:
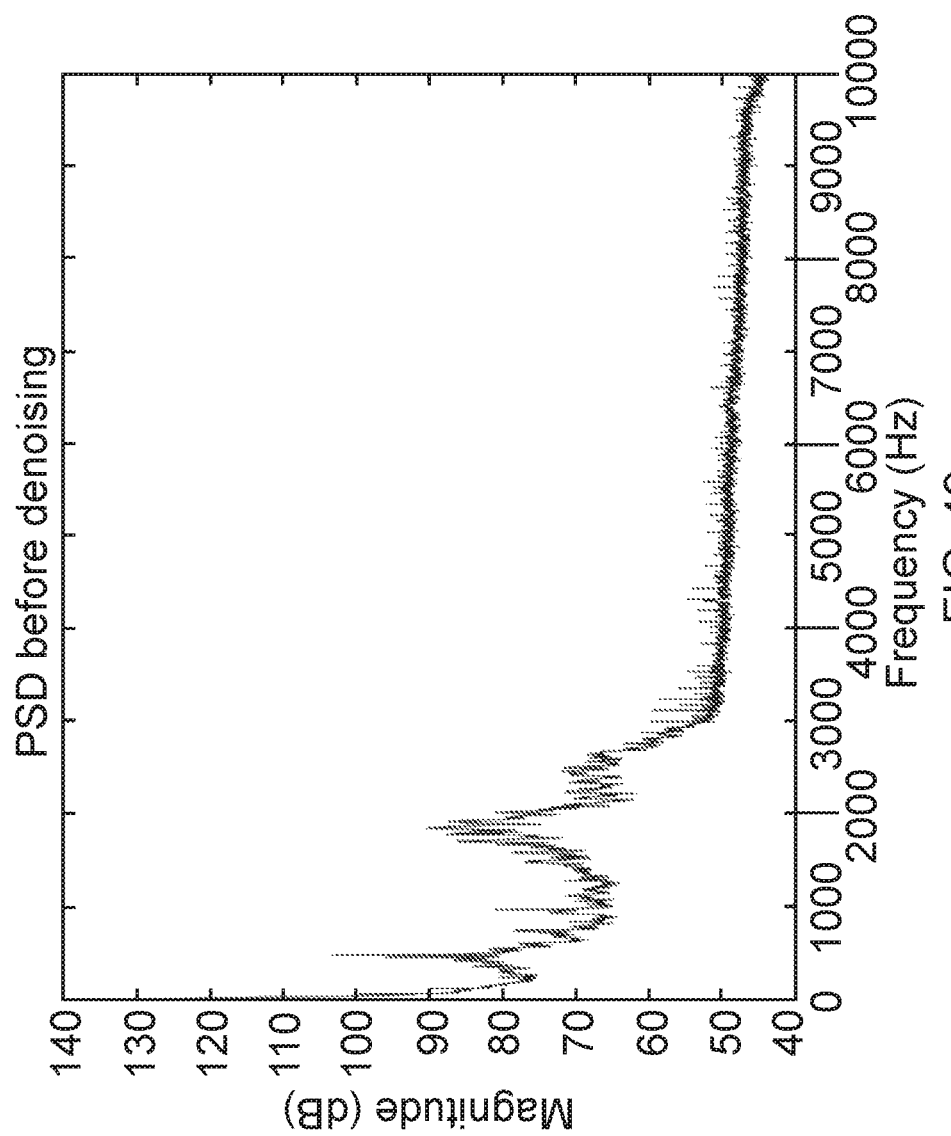
FIG. 49 depicts a PSD before denoising.

We can also test PSD by Welch with no overlaps:

Sgm=10000; noverlaps=0; [Pxx,F]=pwelch(x, sgm, noverlaps, [ ], Fs);

Plot(F,10*log 10(Pxx)); xlabel('Frequency (Hz)'); ylabel ('Magnitude (dB)'); title ('PSD before nenoising'). This results in the plot of FIG. 49.

Figure 50:
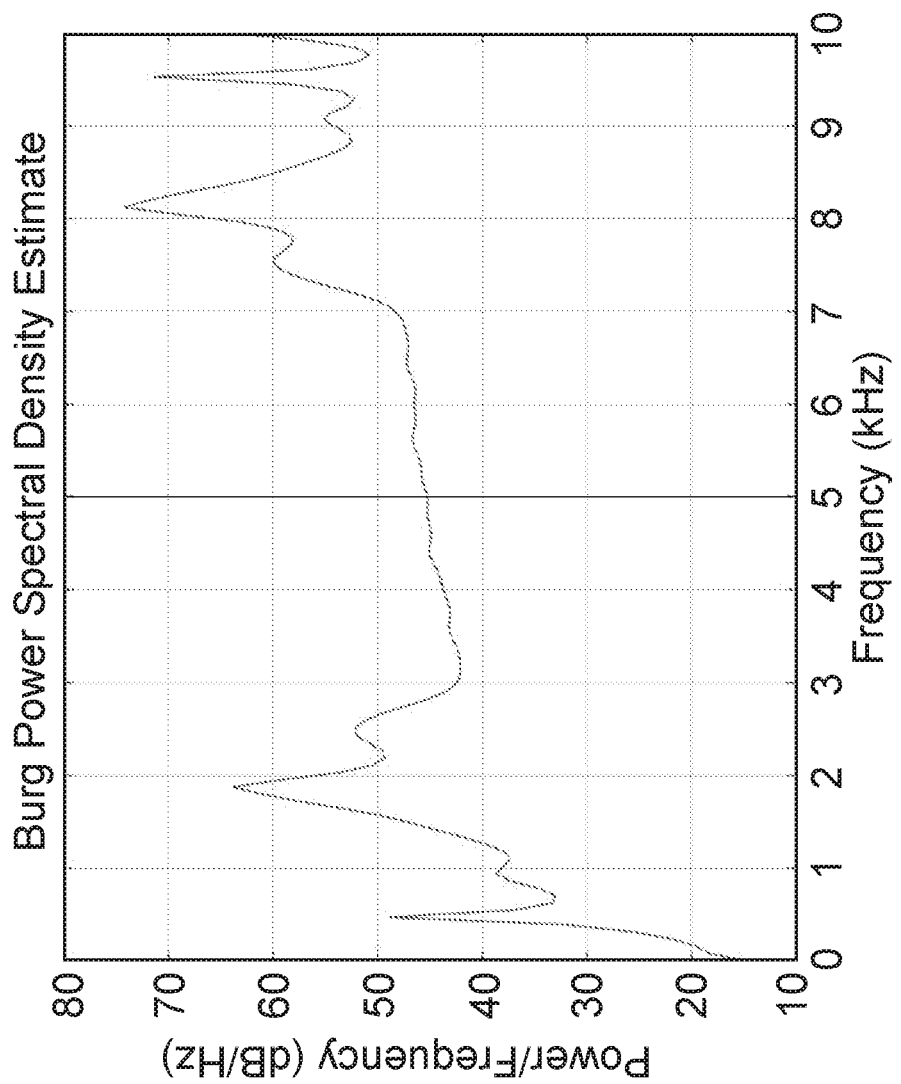
FIG. 50 depicts a Burg's Power Spectral Density Estimate.

If we zoon in the range of 2K Hz, with:

Uf=2000; plot (F1:uf), 10*log 10(Pxx)1:uf))

xlabel('Frequency (Hz)'); ylabel('Magnitude (dB)'); title ('PSD before nenoising'). This results in the plot of FIG. 50.

Finally, we can output with frequencies, for peak analysis with [Pxx, F]=pburg(D1, 50, [ ], Fs0' and zoom to within 2000 Hz (though 3000 would be good as well).

Figure 51:
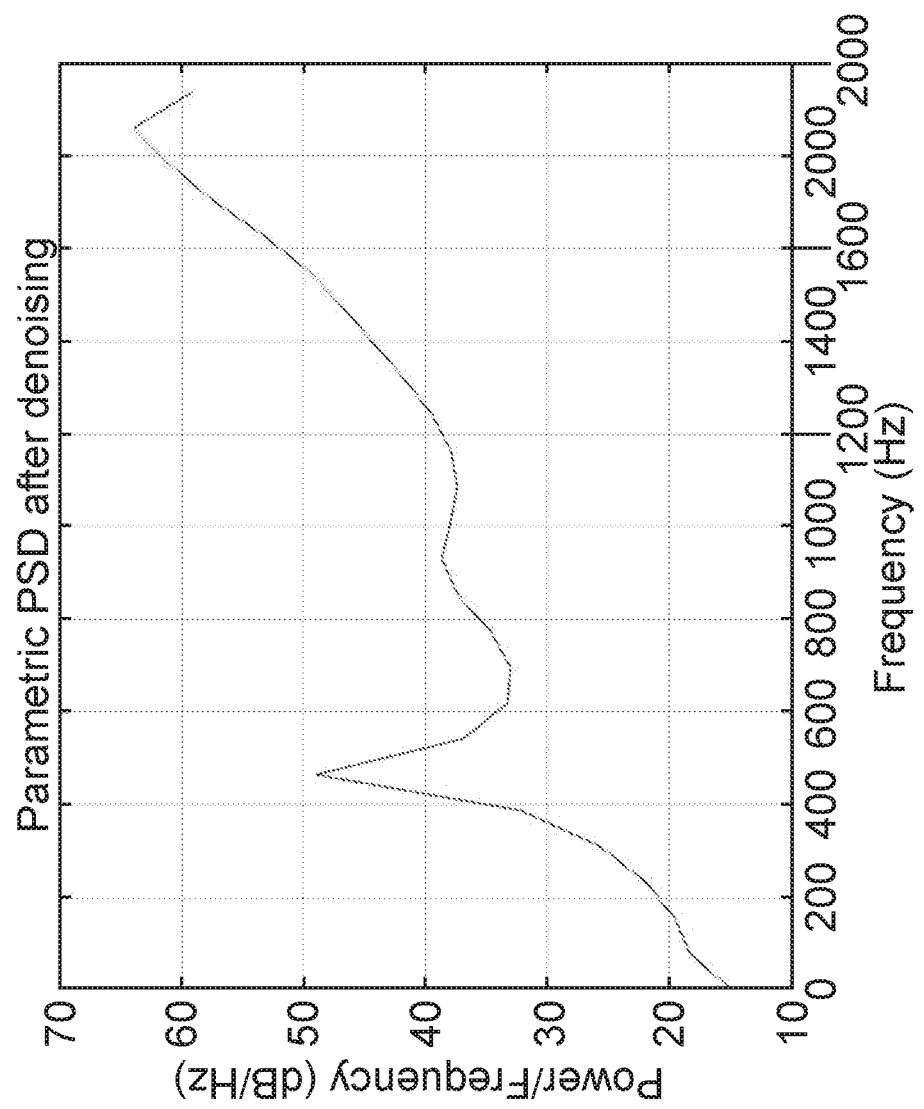
FIG. 51 depicts a Parametric PSD after denoising, depicting peaks.

Plot (0; 1000/129:1938, 10*log 10(Pxx(1:26))) grid on;

Legend ('pburg PSD estimate')

xlabel('Frequency (Hz)'); ylabel('Magnitude (dB/Hz)'); title ('Parametric PSD after denoising). This results in the plot of FIG. 51

We then allow the software to define the peaks. Once identified, the peaks can be used to calculate stenosis by (1−d/D)×100.

Accordingly, we know that ambient noise is present in any data set and we know some of the sounds that are always present. Furthermore, we know the sounds that we are trying to detect and have determined that these sounds are at range 20-3000 Hz. We can remove other sounds introduced through these sensitive machines and concept is to provide a claim that covers the external and internal steps being applied to generate clean data.

In certain embodiments, we determine stenosis based upon a class of stenosis. For example a first class may be less than 25% stenosis. A second class may be less than 50% stenosis, less than 70% stenosis, less than 90% stenosis. Accordingly, a method may be to calculate a binary response of less than or more than 25% stenosis. Another method may be to calculate a binary response of less than or more than 50% stenosis. Another method may be to calculate a binary response of less than 70% or less than 90% stenosis.

Calculation of stenosis in such binary decision charts allows for a broad and quick determination of risk to a patient. Furthermore, certain procedures may be medically recommended at a certain stenosis percentage. Accordingly, for example, when testing the coronary artery, it may be necessary only to determine a binary decision of more or less than 50% stenosis, as procedures are recommended for surgical action once stenosis reaches such threshold.

Utilizing the devices, systems, and methods as described above, the present components can be utilized in a system to identify large ring vortices from a fluid flow vessel. We can then analyze the signal utilizing low frequency (Spectral) methods and assess the range of stenosis, occlusion.

In preparing for a test, the system first goes through a series of calibration steps, ensuring correct receipt of the signals, correlating the signals from the two carotid arteries and the heart, and identifying the systolic time, the period of most rapid fluid flow. Once the signal is recorded, the system prepares the data for processing the digital signal to conduct a spectral analysis. Using the signal features, a statistical analysis is performed against multiple parameters to render a classification of degree of stenosis, occlusion or aneurysm within each fluid flow vessel. For stenosis of the carotid artery, the output renders a report indicating a range of blockage against the defined Nascet categories with a representation of the systolic events.

In accordance with one embodiment, the sensor array one or more sensors, which are positioned proximate the fluid flow vessel to be examined. In some instances the sensors are placed onto an array for determination of stenosis of the carotid artery. An array comprises two branches, which are biased inward and can be bent/flexed outward to the proper position. To accommodate bodies of differing heights, additional modifications can be made to allow for the adjustment of the lower sensor with respect to the upper sensors (e.g., providing a telescoping or otherwise extendable portion or arrangement in the lower branch and/or the upper two branches).

A particular feature of the array is that it is adjustable and can be configured to account for the anatomical differences between individuals, while remaining sufficiently rigid to support the sensing elements. Furthermore, the shape and design of the array is particular important to assist with orienting sensing elements to each portion of the array, wherein sensing elements can easily be positioned adjacent to the neck for appropriate positioning to sense the carotid artery. At the same time, the materials and the angles utilized in the array provide appropriate resistance and a gentle force to compress the sensing element to the side of the neck for sensing. The shape and material thus provide an important feature to gently, but securely assist in positioning of the sensing elements and for testing patients for stenosis of the carotid artery.

The array is adjustably designed to fit a majority of adults and to be held by the patient or a third person when performing a carotid artery test. In a preferred embodiment, the array, when placed on the patient, imparts sufficient pressure on the patient so as to achieve a measurement of sufficient quality to accurately determine stenosis, while limiting the pressure applied to the carotid artery. The goal is for there to be sufficient pressure to assist in positioning the sensing elements, and maintaining their position for about 2-3 minutes during a test, but not such pressure as to significantly impact the shape and size of the carotid artery being assessed. Indeed, as a whole, the array and the sensing elements are designed to be a passive test that is non-emitting, non-invasive, and is configured so that anyone can conduct the test without requiring certification.

In accordance with one embodiment, the sensor elements in collaboration with the software or application running on a PC or main computing unit, takes three readings simultaneously from the right and left carotid arteries in the neck and from the heart just below the sternum, calibrates the sound signature, filters and then digitizes data for analysis. A shielded cable transmits the signals to the main computing unit. In further embodiments, signals and data can be transmitted via other transmission means, including wireless, Bluetooth, or other suitable data transmission mechanisms.

Therefore, a method for determining stenosis of the carotid artery in a human patient consists of a first step of placing a sensing device onto the patient, wherein a first sensing element is placed adjacent to the carotid arteries; the sensing elements then measure sounds from the carotid artery. The sound is measured in analog and modified to digital format and then analyzed before a power spectral density analysis is performed. The power spectral density graph reveals peaks that are then analyzed to provide for a calculation of percent stenosis or occlusion of the carotid artery.

What is claimed is:

1. A method for measuring sound from vortices in the carotid artery comprising:
   a. performing a first quality control procedure on at least two sensing elements, wherein said quality control procedure is performed by playing a predetermined set of tones within a base unit, wherein said at least two sensing elements detect said set of tones and wherein said detected tones are compared to said predetermined set of tones, wherein the sensing elements are replaced if the comparison between said detected tones and said predetermined tones has a variance of more than 10% relative to a frequency;
   b. performing a second quality control procedure on at least two sensing elements, wherein said second quality control procedure is performed by detecting blood flow through the carotid artery and comparing said detected sounds to a predetermined sound signature, wherein the sensing element is repositioned if the detected sounds compared to the predetermined sound signature have a variance of more than 25% relative to the frequency, wherein if the variance in the second quality control procedure is more than 100% relative to the frequency, step (a) is repeated; and
   c. detecting sounds generated by the vortices in the carotid artery for at least 30 seconds.

2. The method of claim 1, wherein the sounds detected from the vortices in the carotid artery are between 40 Hz and 3000 Hz.

3. The method of claim 1, wherein a further step (d) comprises eliminating sounds from the carotid artery that are outside of the range of 40 Hz and 3000 Hz.

4. The method of claim 3, comprising a further step (e) comprising generating a power spectral density graph of the sounds from step (d).

5. The method of claim 1 comprising three sensor pods.

6. A method for measuring vortices produced in the carotid artery due to plaque accumulation in the artery comprising:
   a. performing a first quality control procedure on at least two sensing elements, wherein said quality control procedure is performed by playing a predetermined set of tones within a base unit, wherein said at least two sensing elements detect said predetermined set of tones forming detected tones, and wherein said detected tones are compared to said predetermined set of tones, wherein if said detected tones are within 10% of a frequency, the first quality control procedure is passed, and wherein if said detected tones are not within 10% of the frequency, the first quality control fails, then replace one or more sensing elements;
   b. performing a second quality control procedure on at least two sensing elements, wherein said second quality control procedure is performed by detecting sounds generated by blood flow through the carotid artery; wherein said at least two sensing elements detect said sounds generated by blood flow through the carotid artery, and said detected sounds are compared to a previously recorded sound signature, indicating an appropriate position for the one or more sensing elements if the detected sounds are within 25% of a frequency of the sound signature, or repositioning the one or more sensing elements if the detected sounds are greater than 25% of the frequency of the sound signal and wherein if the variance in the second quality control procedure is more than 100% relative to the frequency, step (a) is repeated; and c. detecting sounds generated by sounds from vortices in the carotid artery for at least 30 seconds.

7. The method of claim 6 comprising three sensor pods, wherein in step (c), detection of sounds generated by sounds from the vortices in the carotid artery are detected simultaneously by the sensor pods.

8. The method of claim 6, wherein the sounds detected in step (c) are between 20 and 3000 Hz.

9. The method of claim 6, further comprising:
e. down sampling the detected sounds from step (b) from analog to digital at a sampling rate of 20 KHz; and
f. removing sounds from the digital outside of the 40 Hz to 3000 Hz range.

10. The method of claim 9 comprising a further step (g) of generating a Power Spectral Density plot and detecting peaks in said plot.

11. The method of claim 10 comprising a further step (h) of determining percent stenosis from the peaks in said plot by calculating $(1-f1/f2) \times 100$.

12. The method of claims 1 or 6 performed by a device for detecting stenosis in the arterial circulatory system comprising a base and at least one sensor pod; said base comprising a processor and a speaker, capable of playing a predetermined sound through said speaker; said sensor pod comprising a circular piezo cap comprising a top and a bottom and an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to and adhered to said flange; a printed circuit board having a ring shape and an outer diameter to fit within the opening and engaged to the bottom of said flange; and on said inner face one-half of an attachment means for securing said disposably piezo assembly to an assembly base.

13. A method for detecting stenosis of the arterial circulatory system comprising: performing a self-diagnosis quality control procedure on a sensor element by playing a predetermined sound signature from a speaker; detecting said predetermined sound signature with said sensor element; comparing said detected sound signature to said predetermined sound signature; proceeding to a second quality control procedure if said detected sound is within 25% of a frequency of the predetermined sound signature or replacing said sensor element if said detected sound is more than 25% from the frequency of the predetermined sound signature; placing said sensor element on an artery of interest; detecting a flow of fluid through said artery of interest wherein the sensing element is repositioned if the detected sounds compared to the predetermined sound signature have a variance of more than 25% relative to the frequency, wherein if the variance in the second quality control procedure is more than 100% relative to the frequency, the self-diagnosis quality control procedure is repeated; detecting a frequency of between 60 and 260 Hz to confirm proper position of said sensing element; moving said sensing element to a different position if a frequency between 60 and 260 Hz is not detected; upon detecting said frequency between 60 and 260 Hz, capturing data from said sensing element; plotting a Power Spectral Density Plot; calculating stenosis based on $(1-f1/f2) \times 100$.

14. The method of claim 13 further comprising performing a wavelet analysis after capturing data from said sensing element.

15. The method of claim 14 further comprising performing Burg's Method after the wavelet analysis.

16. The method of claim 15 further comprising performing Welch's method after performing Burg's Method.

17. The method of claim 13 wherein the calculation of stenosis is a binary calculation of greater than or less than 50%.

* * * * *